(12) United States Patent
Metcalfe et al.

(10) Patent No.: US 10,835,611 B2
(45) Date of Patent: Nov. 17, 2020

(54) NEUROTHERAPEUTIC NANOPARTICLE COMPOSITIONS COMPRISING LEUKEMIA INHIBITORY FACTOR

(71) Applicants: Yale University, New Haven, CT (US); Susan Marie Metcalfe, Cambridge (GB)

(72) Inventors: Susan Marie Metcalfe, Cambridge (GB); Tarek Fahmy, New Haven, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 15/990,259

(22) Filed: May 25, 2018

(65) Prior Publication Data
US 2018/0271985 A1    Sep. 27, 2018

Related U.S. Application Data

(60) Division of application No. 14/628,050, filed on Feb. 20, 2015, now abandoned, which is a continuation of application No. PCT/US2013/056246, filed on Aug. 22, 2013.

(60) Provisional application No. 61/692,519, filed on Aug. 23, 2012, provisional application No. 61/707,723, filed on Sep. 28, 2012.

(51) Int. Cl.
| | |
|---|---|
| *A61K 47/42* | (2017.01) |
| *B82Y 5/00* | (2011.01) |
| *A61K 38/18* | (2006.01) |
| *C07K 16/28* | (2006.01) |
| *A61K 47/69* | (2017.01) |
| *A61K 9/48* | (2006.01) |
| *A61K 38/20* | (2006.01) |

(52) U.S. Cl.
CPC ............ *A61K 47/42* (2013.01); *A61K 9/4866* (2013.01); *A61K 38/185* (2013.01); *A61K 38/1808* (2013.01); *A61K 38/204* (2013.01); *A61K 38/2093* (2013.01); *A61K 47/6907* (2017.08); *B82Y 5/00* (2013.01); *C07K 16/2863* (2013.01)

(58) Field of Classification Search
None
See application file for complete search history.

(56) References Cited

U.S. PATENT DOCUMENTS

| | | | |
|---|---|---|---|
| 9,101,548 B2 | 8/2015 | Metcalfe et al. | |
| 2002/0128179 A1 | 9/2002 | Tacon et al. | |
| 2003/0013674 A1 | 1/2003 | Bednarski et al. | |
| 2005/0100877 A1 | 5/2005 | Xu et al. | |
| 2008/0260650 A1 | 10/2008 | Tawakol et al. | |
| 2010/0055167 A1 | 3/2010 | Zhang et al. | |
| 2010/0151436 A1 | 6/2010 | Fong et al. | |
| 2015/0231266 A1 | 8/2015 | Metcalfe et al. | |
| 2015/0366994 A1 | 12/2015 | Metcalfe et al. | |

FOREIGN PATENT DOCUMENTS

| | | |
|---|---|---|
| EP | 1011712 B1 | 4/1999 |
| EP | 2305253 | 4/2011 |
| WO | WO 1999/27950 A1 | 6/1999 |
| WO | WO 2001/64239 A1 | 9/2001 |
| WO | WO 2002/15877 A2 | 2/2002 |
| WO | WO 2003/008566 A1 | 1/2003 |
| WO | WO 2004/084950 A2 | 10/2004 |
| WO | WO 2005/051305 A2 | 6/2005 |
| WO | WO 2005/074973 A2 | 8/2005 |
| WO | WO 2005/122734 A2 | 12/2005 |
| WO | WO 2006/080951 A2 | 8/2006 |
| WO | WO 2008/052046 A2 | 5/2008 |
| WO | WO 2009/051837 A2 | 4/2009 |
| WO | WO 2009/053718 | 4/2009 |
| WO | WO 2009/129476 A2 | 10/2009 |
| WO | WO 2011/041897 | 4/2011 |
| WO | WO 2014/031883 A1 | 2/2014 |

OTHER PUBLICATIONS

Perez, Author Manuscript of Biol Biomed Rep. 2012; 2(1): 59-69 (Year: 2012).*
Metcalfe et al., Nanobiomedicine, 2015, 2:5; doi: 10.5772/60622 (Year: 2015).*
Metcalfe et al., Current Pharmaceutical Design, 2017, 23; 776-783 (Year: 2017).*

(Continued)

*Primary Examiner* — Christina M Borgeest
(74) *Attorney, Agent, or Firm* — Hamilton, Brook, Smith & Reynolds, P.C.

(57) ABSTRACT

There are provided compositions and methods for treatment of neurodegeneative diseases and CNS injury. The compositions a pharmaceutically acceptable carrier solution; and a plurality of biodegradable nanoparticles, wherein the nanoparticles comprise a targeting moiety that is able to bind selectively to the surface of a neural stem cell and wherein the nanoparticles further comprise factors such as leukaemia inhibitory factor (LIF); XAV939 and/or one or more of: brain-derived neurotrophic factor (BDNF) or an agonist thereof; epidermal growth factor (EGF) or an agonist thereof; glial cell-derived neurotrophic factor (GDNF) or an agonist thereof; retinoic acid and derivatives thereof; ciliary neurotrophic factor (CTNF) or an agonist thereof; and Wnt5A. The biodegradable nanoparticles may deliver via controlled time release.

18 Claims, 33 Drawing Sheets

(56) References Cited

OTHER PUBLICATIONS

Kim and de Vellis, J. Neuroscience Research 87:2183-2200 (2009) (Year: 2009).*
Schweyer et al., Scientific Reports (2019) 9:13359; 10 pages total (Year: 2019).*
Akita S. et al., "Leukemia Inhibitory Factor Gene Improves Skin Allograft Survival in the Mouse Model," Transplantation, 70:7:1026-1031, Oct. 2000.
Akiyama, et al., "In vivo effect of recombinant human LIF in primates," Japanese Journal of Cancer Research, vol. 88, pp. 578-583, Jun. 1997.
Aluvihare V. et al., "The Role of Regulatory T Cells in Alloantigen Tolerance," lmmunol Rev. (Aug. 2006) 212:330-343.
Anderson et al.; "Entrapment of human Leukocyte interferon in the aqueous interstices of liposomes;" Infect. Immun., 31(3):1099-1103, Mar. 1981; abstract only, 2 pages.
Barker, R. A., "Stem Cells and Neurodegenerative Diseases—Where is it all going?," Regen.Med., vol. 7, No. 6s, pp. 26-31, Nov. 2012.
Bauer, S., et al., "Leukemia Inhibitory Factor Promotes Neural Stem Cell Self-Renewal in the Adult Brain," Journal of Neuroscience, vol. 26 No. 46, pp. 12089-12099, Nov. 2006.
Berry M.F. et al. "Targeted Overexpression of Leukemia Inhibitory Factor to Preserve Myocardium in a Rat Model of Postinfarction Heart Failure," J Thorac Cardiovasc Surg. (Dec. 2004)128:866-875.
Blakely, B. D., et al., "Wnt5a Regulates Midbrain Dopaminergic Axon Growth and Guidance," *PLoS One*, vol. 6; Issue 3; e18373; 15 pages (2011).
Butzkueven, H., et al., "LIF receptor signaling limits immune-mediated demyelination by enhancing oligodendrocyte survival," Nat Med, vol. 8, No. 6, pp. 613-619, Jun. 2002.
Chen Z.K. et al., "Amplification of Natural Regulatory Immune Mechanisms for Transplantation Tolerance," Transplantation (Nov. 1996) 62:9:1200-1206.
Cleland et al.; "Stable formulations of recombinant human growth hormone and interferon-gamma for microencapsulation in biodegradable microspheres;" Pharm. Res. 13(10):1464-1475, Oct. 1996; abstract only, 2 pages.
Davies J. et al., "'Camelising' Human Antibody Fragments: NMR Sutides on VH Domains," FEB Letters (Jan. 1994) 339:285-290.
Deverman, B, E., et al., "Exogenous Leukemia Inhibitory Factor Stimulates Oligodendrocyte Progenitor Cell Proliferation and Enhances Hippocampal Remyelination," Journal of Neuroscience, vol. 32, pp. 2100-2109, Feb. 2012.
Dinauer, N., et al., "Selective Targeting of Antibody-Conjugated Nanoparticles to Leukemic Cells and Primary T-Lymphocytes," Biomaterials 26: 5898-5906 (Apr. 2005).
Dumstrei, K., et al., "EGFR signaling is required for the differentiation and maintenance of neural progenitors along the dorsal midline of the *Drosophila* embryonic head," *Development*, vol. 125; 3417-3426 (1998).
Estrada, C. and Villalobo, A., "Epidermal Growth Factor Receptor in the Adult Brain," Ch. 20 of *The Cell Cycle in the Central Nervous System* (Janigro, D. ed.), 265-277 (2006).
Fahmy T. et al., "Nanosystems for Simultaneous Imaging and Drug Delivery to T Cells," AAPS J. (Jun. 2007) 9:2:E171-E180.
Fahmy T. et al., "Surface Modification of Biodegradable Polyesters with Fatty Acid Conjugates for Improved Drug Targeting," Biomaterials (Apr. 2005), 26:5727-5736.
Fahmy T. et al., "Targeted for Drug Delivery," Nanotoday (Aug. 2005) 18-26.
Fancy, S. P. J., et al., "Axin2 as Regulatory and Therapeutic Target in Newborn Brain Injury and Remyelination," Nat Neurosci., vol. 14, No. 8, pp. 1009-1016, Feb. 2012.
Gao W. et al., "Treg versus Th17 Lymphocyte Lineages are Cross-Regulated by LIF versus IL-6," Cell Cycle (May 2009) 8:9:1444-1450.
GB Search Report (Application No. GB0721081.8) (dated Feb. 26, 2008)—4 pages.
Ghahroudi M. A. et al., "Selection and Identification of Single Domain Antibody Fragments from Camel Heavy-Chain Antibodies," FEBS Letters, (Jun. 1997) 414:521-526.
Gillespie, L. N, et al., "LIF is more potent than BDNF in promoting neurite outgrowth of mammalian auditory neurons in vitro," Neuroreport, vol. 12, No. 2, pp. 275-279, Feb. 2001.
Gregoriadis et al., "Fate of Liposomes in Vivo: Control Leading to Targeting," NATO ASI Series, Series A: Life Sciences/NATO ASI Ser., Ser. A: vol. 82, Issue: recept.-mediated targeting drugs, pp. 243-266 (1984).
Haeryfar et al., "Thy-1: More than a Mouse Pant-T Cell Marker," J. Immunol, vol. 173, pp. 3581-3588 (2004).
Hamers-Casterman C. et al., "Naturally Occurring Antibodies Devoid of Light Chains," Nature (Jun. 1993) 363:446-448.
Hilton et al., "Clearance and Fate of Leukemia-Inhibitory Factor (LIF) After Injection Into Mice," J Cell Physiol. (Sep. 1991) 148:3:430-439.
Hombach-Klonisch, et al., "Adult stem cells and their trans-differentiation potential—perspectives and therapeutic applications," J. Mol. Med. (Berl), vol. 86, No. 12, pp. 1301-1314, Dec. 2008.
Hori S. et al., "Control of Regulatory T Cell Development by the Transcription Factor Foxp3," Science (Feb. 2003) 299:5609:1057-1061.
Huang, S.M., et al, "Tankyrase inhibition stabilizes axin and antagonizes Wnt signalling," Nature, vol. 461, No. 7264, pp. 614-620, Oct. 2009.
Inestrosa, N. and Arenas, E., "Emerging roles of Wnts in the adult nervous system," *Nature Reviews Neuroscience*, vol. 11; 77-86 (2010).
Jang, et al., "A selective TrkB agonist with potent neurotrophic activities by 7,8-dihydroxyflavone," PNAS, vol. 107, No. 6, pp. 2687-2692, Feb. 2010.
Jones, K. and Reichardt, L. F., "Molecular cloning of a human gene that is a member of the nerve growth factor family," *Proc. Natl. Acad. Sci.*, vol. 87; 8060-8064 (1990).
Kaur S. et al. "Heparan sulfate modification of the transmembrane receptor CD47 is necessary for inhibition of T cell receptor signalling by thrombospondin-1" J Biol Chem. Apr. 29, 2011;286(17):14991-5002; Epub Feb. 22, 2011.
Li, X., et al., "Manipulating Neural-Stem-Cell Mobilization and Migration in Vitro," Acta Biomaterialia, vol. 8, pp. 2087-2095, Feb. 13, 2012.
Liu, J., et al., "Response of neural precursor cells in the brain of Parkinson's disease mouse model after LIF administration," Neurol. Res., vol. 31, No. 7, pp. 681-686, Sep. 2009.
Linker et al., "Function of Neurotrophic Factors Beyond the Nervous System: Inflammation and Autoimmune Demyelination," Critical Reviews in Immunology, vol. 29, No. 1, pp. 43-68 (2009).
Metcalfe, S. et al., "Leukaemia Inhibitory Factor (LIF) is Functionally Linked to Axotrophin and Both LIF and Axotrophin are Linked to Regulatory Immune Tolerance," FEBS Letters (Dec. 2004) 579:609-614.
Metcalfe S. et al., "Leukemia Inhibitory Factor Is Linked to Regulatory Transplantation Tolerance," Transplantation (Mar. 2005) 79:6:726-30.
Metcalfe, S. M., et al., "Targeted Nanotherapy for Induction of Therapeutic Immune Responses," Trends in Molecular Medicine, vol. 18, No. 2, pp. 72-80, Feb. 2012.
Moore, M. W., et al., "Renal and neuronal abnormalities in mice lacking GDNF," *Nature*, vol. 382; 76-79 (1996).
Moran C.S. et al., "Human Leukemia Inhibitory Factor Inhibits Development of Experimental Atherosclerosis," Arterioscler Thromb Vase. Bioi. (May 1994) 14:1356-1363.
Muthukumarana P. et al., "Regulatory Transplantation Tolerance and 'Sternness': Evidence that FOXP3 May Play a Regulatory Role in SOCS-3 Gene Transcription," Transplantation (Jul. 2007) 84:1S:S6-S11.
Muthukumarana P. et al.. "Evidence for Functional Inter-Relationships Between FOXP3. Leukaemia Inhibitory Factor, and Axotrophin/MARCH-7 in Transplantation Tolerance," Int. Immunopharmacol. (Sep. 2006) 6:1993-2001.

(56) References Cited

OTHER PUBLICATIONS

Niwa, H., et al., "A parallel circuit of LIF signalling pathways maintains pluripotency of mouse ES cells," Nature Jul, vol. 460, No. 7251, pp. 118-122, Jul. 2009.
Park, J. et al., "Modulation of CD4+ T Lymphocyte Lineage Outcomes with Targeted, Nanoparticle-Mediated Cytokine Delivery," Molecular Pharmaceutics, vol. 8, No. 1, pp. 143-152, Feb. 2011.
PCT/ GB2008/003626 Written Opinion and International Search Report dated Aug. 27, 2009, entitled "Immuno-Modulatory Composition," 11 pages.
PCT/GB2008/003626 International Preliminary Report on Patentability dated Apr. 27, 2010 entitled "Immuno-Modulatory Composition," 8 pages.
PCT/US2013/056246 Notification Concerning Transmittal of International Preliminary Report on Patentability dated Mar. 5, 2015 entitled "Neurotherapeutic Nanoparticle Compositions and Devices".
PCT/US2013/056246 Written Opinion and International Search Report dated Jan. 10, 2014, entitled "Neurotherapeutic Nanoparticle Compositions and Devices," 11 pages.
Pcñuclas, et al., "TGF-β Increases Glioma-Initiating Cell Self-Renewal Through the Induction of LIF in Human Glioblastoma," Cancer Cell, vol. 15, No. 4, pp. 315-327, Apr. 7, 2009.
Phillips N.C., Tsoukas C. "Immunoliposome targeting to CD4+ cells in human blood." Cancer Detect Prev. 1990;14(3):383-90.
Piccinni M.P. et al "Production of IL-4 and leukemia inhibitory factor by T cells of the cumulus oophorus: a favorable microenvironment for pre-implantation embryo development." Eur J Immunol. Aug. 2001;31(8):2431-7.
Pitman, M., et al., "LIF receptor signaling modulates neural stem cell renewal," Mol Cell Neurosci, vol. 27, No. 3, pp. 255-266, Nov. 2004.
Prima, V., et al, "Differential Modulation of Energy Balance by Leptin, Ciliary Neurotrophic Factor, and Leukemia Inhibitory Factor Gene Delivery: Microarray Deoxyribonucleic Acid-Chip Analysis of Gene Expression," Endocrinology, vol. 145, No. 4, pp. 2035-2045, Apr. 2004.
Reif, A. E., and Allen, J. M., "The AKR Thymic Antigen and Its Distribution in Leukaemias and Nervous Tissues," J Exp Med., vol. 120, pp. 413-433, Sep. 1964.
Reynolds, A. D., et al., "Regulatory T cells attenuate Th17 cell-mediated nigrostriatal dopaminergic neurodegeneration in a model of Parkinson's disease," J Immunology, vol. 184, pp. 2261-2271, Mar. 2010.
Schwartz, C.M., et al., "NTera2: A Model System to Study Dopaminergic Differentiation of Human Embryonic Stem Cells," Stem Cells and Development, vol. 14, No. 5, pp. 517-534, Oct. 2005.
Stöckli, K. A., et al., "Regional Distribution, Developmental Changes, and Cellular Localization of CNTF-mRNA and Protein in the Rat Brain," *The Journal of Cell Biology*, vol. 115; No. 2; 447-459 (1991).
Sundberg, et al., "CD Marker Expression Profiles of Human Embryonic Stem Cells and Their Neural Derivatives, Determined Using Flow-Cytometric Analysis, Reveal a Novel CD Marker for Exclusion of Pluripotent Stem Cells," Stem Cell Research, vol. 2, No. 2, pp. 113-124, Mar. 2009, Epub Sep. 16, 2008.
Supplementary European Search Report for Application No. EP 13831430, dated Feb. 18, 2016.
Takahashi, J., et al., "Retinoic Acid and Neurotrophins Collaborate to Regulate Neurogenesis in Adult-Derived Neural Stem Cell Cultures," *J. Neurobiol.*, vol. 38; 65-81 (1999).
Transeuro, Innovative Approach for the Treatment of Parkinson's Disease, Nov. 2014, retrieved from the Internet URL: http://www.transeuro.org.uk.
United States Patent Office Action for U.S. Appl. No. 12/739,357 dated Jul. 10, 2012 (18 pages).
United States Patent Office Action for U.S. Appl. No. 12/739,357 dated Oct. 16, 2014 (20 pages).
United States Patent Office Final Rejection for U.S. Appl. No. 12/739,357 dated Jan. 7, 2013 (16 pages).
United States Patent Office Notice of Allowance for U.S. Appl. No. 12/739,357 dated Apr. 8, 2015 (12 pages).
Velge-Roussel, F., et al., "Immunochemical Characterization of Antibody-Coated Nanoparticles," Experientia, 52(8):803-806, Aug. 1996.
Vourc'h, P., et al., "Isolation and characterization of cells with neurogenic potential from adult skeletal muscle," Biochemical and Biophysical Research Communications., vol. 317, No. 3, pp. 893-901, Jan. 2004.
World C.J. et al., "Regulation of LIF Receptor Expression in Vascular Smooth Muscle," Annals of the New York Academy of Sciences (Dec. 2001) 947:323-328.
Zhao, J.-W., et al., "Modelling of a targeted nanotherapeutic 'stroma' to deliver the cytokine LIF, or XAV939, a potent inhibitor of Wnt-β-catenin signalling, for use in human fetal dopaminergic grafts in Parkinson's disease," Disease Models & Mechanisms, vol. 7, pp. 1193-1203, Feb. 2014.
Kim et al., "Stem Cell-Based Cell Therapy in Neurological Diseases: A Review," Journal of Neuroscience Research 87:2181-2200 (2009).

\* cited by examiner

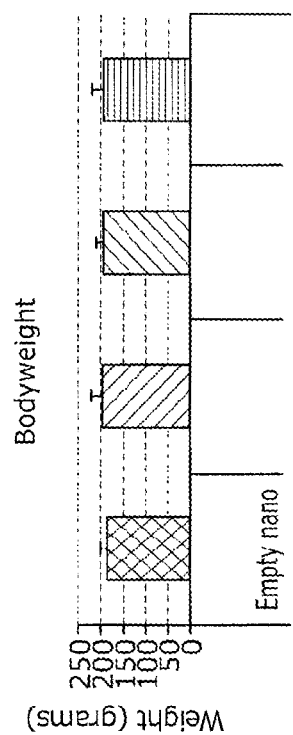
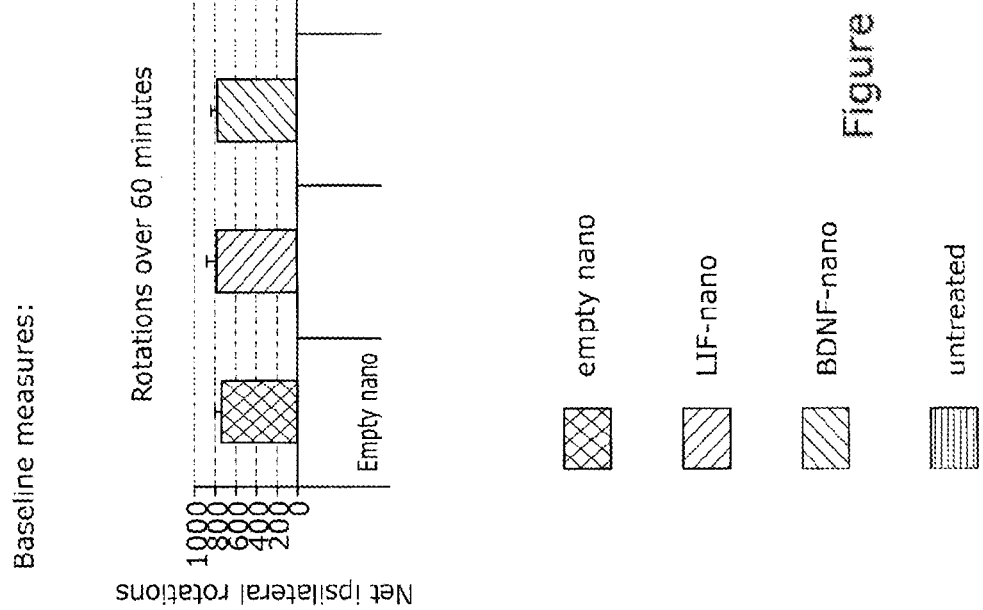
Figure 13A
Figure 13B

Post-surgery measures

NEUROTHERAPEUTIC NANOPARTICLE COMPOSITIONS COMPRISING LEUKEMIA INHIBITORY FACTOR

RELATED APPLICATION(S)

This application is a divisional of U.S. application Ser. No. 14/628,050, filed Feb. 20, 2015, which is a continuation of International Application No. PCT/US2013/056246, which designated the United States and was filed on Aug. 22, 2013, published in English, which claims the benefit of U.S. Provisional Application No. 61/692,519, filed on Aug. 23, 2012 and U.S. Provisional Application No. 61/707,723, filed on Sep. 28, 2012. The entire teachings of the above applications are incorporated herein by reference.

BACKGROUND

The invention is in the field of compositions for neuroprotection, particularly compositions that promote and protect neural cells in the central nervous system of a mammal such as a human. Also described are methods for repairing tissues of the central nervous system of a mammal such as a human. Neurodegenerative diseases represent the largest area of unmet clinical need in the Western world. They are characterised by a progressive loss of the structure or function of neurons in the nervous system (neurodegeneration) and include Alzheimer's Disease (AD), Parkinson's Disease (PD) and a host of other rarer conditions such as Huntington's Disease (HD), Frontotemporal dementia (FTD) and Amyotrophic Lateral Sclerosis (ALS). The process of neurodegeneration is not well understood and so the diseases that stem from it have no effective cures, nor is it possible to slow down their progression, as yet.

Chronic neurodegenerative disorders (NDD) of the central nervous system, which target the aging brain, are set to increase as the population ages and finding ways to better understand and treat these conditions is a major challenge given the personal and economic costs of these conditions. These disorders are defined by the loss of specific populations of neurons with a characteristic pathological pattern of protein aggregation—for example in the case of PD the loss of the nigrostriatal dopaminergic pathway and the presence of alpha synuclein-containing Lewy bodies.

While this is a useful starting point by which to define these diseases, it is though important to realise that these chronic neurodegenerative disorders:
(i) have a much greater extent of pathological burden than was once recognised and as such these diseases target a whole range of different neuronal populations, rather than just one neuronal network;
(ii) have pathology that is not confined to the neurons but involves glial cells and an inflammatory element;
(iii) often display mixed profiles of pathology typically with a significant vascular disease burden in the brain of some of those conditions that affect the more elderly;
are heterogeneous with a complex aetiology. Taking Parkinson's Disease (PD) as an example, this is a degenerative disorder of the central nervous system (CNS) that currently affects approximately 1% of people over 65 years of age and is likely to become more common as the population ages and lives longer. It is characterised clinically by the development of bradykinesia, rigidity and a resting tremor, which has been attributed in part to the progressive degeneration of the dopaminergic input from the substantia nigra to the striatum of the brain. It is increasingly being understood that PD is a disorder which has widespread pathology from its onset and that, therefore, the nigral pathology is only part of a much more diffuse pathological process. However, the core loss of the dopaminergic nigrostriatal pathway is not disputed.

The progressive loss of dopamine can be treated with a range of symptomatic dopaminergic drug therapies, particularly in the early stages of the disease. However, as symptoms progress with time and coupled to the long-term use of dopaminergic drug therapies, a range of problems arise including the development of drug-induced motor complications such as "on-off" fluctuations and levodopa-induced dyskinesias (LID). At this stage of the disease, drug therapies become increasingly disappointing in terms of a reliable therapeutic benefit. Therefore, other therapeutic approaches are used including more invasive ways of delivering more continuous dopaminergic therapy, such as apomorphine pumps and DuoDopa® (constant delivery of L-Dopa into the small bowel), as well as neurosurgical interventions such as deep brain stimulation, especially of the subthalamic nucleus.

These latter therapies can be effective, but only ever treat the symptoms without any attempt to repair the underlying and progressive disease. Thus, these treatments also start to fail, in part because of this progressive nature of the non-nigral, non-motor aspects of Parkinson's Disease and in part because of the continued loss of nigral dopaminergic neurones. Therefore, whilst a better understanding of disease pathogenesis may enable better treatment of all aspects of PD, more restorative approaches to repairing the dopaminergic nigrostriatal tract, including cell replacement, neurotrophic support and pharmacological and gene therapies, may also prove very useful.

Thus, NDD are characterised by a slow insidious progression with increasing misery for the patient and their family, and increasing burden on healthcare systems worldwide. Alzheimer's Disease (AD) afflicts some 8 million in the Western World; PD around 120,000 in the UK; 1 million in the USA; and 4 million worldwide. Huntington's Disease cases number some 6,000 in the UK, and 30,000 in the USA. Development of strategies to improve treatment of NDD is a pressing priority. Currently patients with NDD are managed in general neurology/medical or specialist clinics, and offered some symptomatic drugs which, whilst helpful in some of these conditions, are often only useful in the early stages of disease. Early management is more in the community, but over time there are increasing co-morbidities that in turn greatly escalate costs in their management.

Stopping or slowing down the disease process at the early stages of NDD conditions would represent a very major therapeutic advance with far reaching benefits to those afflicted, and within the health care organisations worldwide.

At the cellular level attempts to slow down or reverse the neurodegenerative disease process have produced variable results. One of the most effective reparative therapies in patients to date has been with allotransplants of dopamine neuroblasts obtained from foetal ventral mesencephalic (VM) tissue. Some grafted patients have responded well and come off anti-PD medication for years, whilst others have shown no or only modest clinical improvements. Moreover, a subset of patients also developed severe, off-state graft-induced dyskinesias, which in a few cases have required additional neurosurgical intervention. The reasons behind this heterogeneity of outcomes and the emergence of graft-induced dyskinesias, in particular, are unknown. There is, therefore, an urgent need for an optimised and more standardised procedure that will translate into more consistently efficacious transplants with minimal side-effects. Current cell harvest procedures typically incur an 80% cell death rate of an already scare cell resource; therefore, there is a need to reduce the cell death rate and reduce the amount of tissue required for allo- or autografting by optimising procedures for cellular therapy. Thus, in cell therapy for PD, problems arise from the scarcity and ex vivo fragility of fetal dopaminergic cells.

The newly developed capacity to re-programme adult somatic cells from patients with neurodegenerative diseases has opened up new possibilities in this area. The technology of inducible stem cells has been used to better understand these diseases and in addition provide a potential future resource for cell transplantation.

Other experimental treatments aim to repair the core pathology, for example by delivering soluble growth factors to rescue the diseased cells from dying, or by immunising against the protein that lies at the core of the pathology (e.g. amyloid in Alzheimer's disease). However, such approachs have so-far failed to deliver substantial clinical benefits. One exception exists where L-DOPA-synthesising enzymes were delivered via lentivirus to the substantia nigra. Whilst this exception proves that repair at the level of neuro-biochemistry is possible, viral-mediated delivery involves risk of unwanted side-effects due to viral components in addition to generating an immune response within the patient against the therapeutic protein itself. Use of soluble growth factors alone is not simple, and may incur substantial off-target side-effects including the risk of carcinogenesis. Even targeted delivery of growth factor using gene therapy into the CNS, including leukaemia inhibitory factor (LIF) gene therapy, revealed the issue of increased endogenous inflammatory gene expression profiles and severe cachexia due to long term high level of LIF exposure (Prima et al, 2004, Endocrinology). Thus there is an outstanding need for a means of controlled, transient, paracrine-type delivery of growth factor to the CNS at physiological doses where the aim is to stimulate endogenous repair within the CNS. This need is combined with the need to protect the therapeutic growth factor from degradation by circulating proteases in the blood, plus the need to avoid troughs and peaks of exposure to the growth factor that are associated with bolus delivery.

In addition to chronic neurodegenerative disorders, damage to cells within the CNS may arise following traumatic injury, hypoxic injury as may occur in newborns, and axonal damage occuring as a result of demeylinating disorders.

In summary, the need to improve the treatment of NDDs, injuries of the CNS, hypoxic injury in newborns and trauma arising from demeylinating disorders by repairing or replacing damaged CNS neural tissue requires an approach that is simple, transient, non-invasive and non-inflammatory, with the aim of harnessing endogenous repair and slowing down, stopping or even reversing disease progression.

Nanomedicine is now recognised worldwide as representing new opportunities in clinical medicine. Currently untreatable illnesses including NDD present key future targets for nano-therapeutic intervention. Within the CNS endogenous neural stem and precursor cells (NSC and NPC) constitute up to 10% of the brain, providing a potential resource of healthy cells can be exploited to replace diseased neural tissue by stimulation with neural growth factors.

Accordingly, the present invention seeks to overcome or at least reduce the problems that exist in the treatment of tissue damage within the CNS including that caused by neurodegenerative diseases by providing a nanotherapeutic composition for targeted delivery of factors to expand, and/or to protect and/or to differentiate neural stem cells, and/or neural progenitor cells and/or induced pluripotent stem cells. This includes recruiting the endogenous stem cells that exist in the adult brain and which are able to replace damaged cells and so maintain good brain function. The invention enables (i) expansion and protection of healthy brain cells; (ii) improved cell therapy for NDD; and (iii) development of neuronal models of clinical disease to identify new therapies including nanotherapeutics to abrogate the clinical disease process. By delivering critical neural growth factors direct to neural progenitor cells either ex vivo, or direct to endogenous cells within the brain, the invention will stop or even reverse disease progression.

SUMMARY OF THE INVENTION

A first aspect of the invention provides a composition for the treatment of neurodegenerative disease comprising:
 a) a pharmaceutically acceptable carrier solution; and
 b) a plurality of biodegradable nanoparticles, wherein the nanoparticles comprise a targeting moiety that is able to bind selectively to the surface of a neural stem cell and wherein the nanoparticles further comprise leukaemia inhibitory factor (LIF).

In a specific embodiment of the invention the targeting moiety is further able to bind selectively to the surface of one or more of the group consisting of: a pluripotent stem cell; a totipotent stem cell; an embryonic stem cell (ESC); an induced pluripotent stem cell (iPSC); a T lymphocyte; an ectodermal cell; a precursor cell having commitment to a neurectodermal lineage; a neural cell; a neuroglial cell, and a neuronal cell.

In an embodiment of the invention the nanoparticles comprise a biodegradable polymer layer that encapsulates the LIF. Optionally, the polymer comprises poly(lactic)-co-glycolic acid (PLGA) and/or PLA. In an alternative embodiment of the invention the nanoparticles comprise a lipid layer that encapsulates the LIF so as to form a liposome nanoparticle, optionally the lipid layer may comprise a phospholipid bilayer.

According to a specific embodiment of the invention the targeting moiety is selected from a monoclonal antibody; a polyclonal antibody; an antigen-binding antibody fragment; a ligand; an aptamer and a small molecule. In one embodiment of the invention the targeting moiety binds specifically to a Thy-1 antigen present on the surface of the neural stem cell and/or the neural progenitor cell and/or the induced pluripotent stem cell.

In a particular embodiment of the invention the nanoparticles further comprise one or more of the following therapeutic (compounds) biologics: brain-derived neurotrophic factor (BDNF) or an agonist thereof; epidermal growth factor (EGF) or an agonist thereof; glial cell-derived neurotrophic factor (GDNF) or an agonist thereof; retinoic acid and derivatives thereof; ciliary neurotrophic factor (CTNF) or an agonist thereof; Wnt5A.

According to an embodiment of the invention the nanoparticles suitably have a diameter of at least about 50 nm and at most about 300 nm; optionally at least about 100 nm and at most about 200 nm. Suitably the nanoparticles are capable of degrading of a period of time in order to effect timed release of the encapsulated LIF. Optionally the period of time may be selected from the group consisting of: 1, 2, 3, 4, 5, 6, 7, 8, 9, 10, 12 days; 1, 2, 3, 4, 5 or 6 weeks; and up to six months.

A second aspect of the invention provides a method for expanding a population of stem cells having the capacity to act as a neural precursor cell comprising exposing the cells to a plurality of biodegradable nanoparticles, wherein the nanoparticles comprise a targeting moiety that is able to bind selectively to the surface of the stem cells and wherein the nanoparticles further comprise leukaemia inhibitory factor (LIF).

In an embodiment of the invention, the stem cells having the capacity to act as a neural precursor cell are selected from one or more of the group consisting of: neural stem cells; neural progenitor cells; pluripotent stem cells; totipotent stem cells; embryonic stem cells (ESCs); induced pluripotent stem cell (iPSCs); induced neural cells (iN); induced dopaminergic cells (iDA); induced oligodendrocytes (iOD); ectodermal cells; precursor cells having commitment to a neurectodermal lineage; neural cells; and neuronal cells.

In an embodiment of the invention the nanoparticles comprise a biodegradable polymer layer that encapsulates the LIF. Suitably the polymer comprises poly(lactic)-coglycolic acid (PLGA) and/or PLA or a suitable biocompatible equivalent. In an alternative embodiment of the invention the nanoparticles comprise a lipid layer that encapsulates the LIF so as to form a liposome nanoparticle, suitably a phospholipid bilayer.

In a particular embodiment of the invention the nanoparticles comprise a targeting moiety that is selected from a monoclonal antibody; a polyclonal antibody; an antigen-binding antibody fragment; a ligand; and a small molecule. Suitably the targeting moiety may bind specifically to a Thy-1 antigen present on the surface of the stem cell.

According to a specific embodiment of the invention the nanoparticles further comprise one or more of the compounds selected from: brain-derived neurotrophic factor (BDNF) or an agonist thereof; epidermal growth factor (EGF) or an agonist thereof; glial cell-derived neurotrophic factor (GDNF) or an agonist thereof; retinoic acid and derivatives thereof; ciliary neurotrophic factor (CTNF) or an agonist thereof; Wnt5A.

In embodiments of the invention the method is carried out in vitro, ex vivo or in vivo.

A third aspect of the invention provides a method for treating a subject suffering from a neurodegenerative disease (NDD) or CNS damage comprising administering to the subject a pharmaceutical composition comprising a plurality of biodegradable nanoparticles, wherein the nanoparticles comprise a targeting moiety that is able to bind selectively to the surface of a neural precursor cell and wherein the nanoparticles further comprise leukaemia inhibitory factor (LIF). Suitably, the neural precursor cell comprises a neural stem cell and/or a neural progenitor cell. In an embodiment of the invention the targeting moiety is further able to bind selectively to the surface of one or more of the group consisting of: a pluripotent stem cell; a totipotent stem cell; an embryonic stem cell (ESC); an induced pluripotent stem cell (iPSC); induced neural cells (iN); induced dopaminergic cells (iDA); induced oligodendrocytes (iOD); a T lymphocyte; an ectodermal cell; a precursor cell having commitment to a neurectodermal lineage; a neural cell; and a neuronal cell.

According to a specific embodiment of the invention the subject is an animal, suitably a mammal, optionally selected from the group consisting of: sheep; cattle; rodents; rabbits; pigs; cats; dogs; and primates. Where the mammal is a primate the primate may be a human.

A fourth aspect of the invention provides for a nanoparticle device comprising:

a biodegradable carrier material, a therapeutic compound, and a targeting moiety;

wherein the carrier material is configured so as to encapsulate the therapeutic compound and wherein the carrier material further defines a surface, upon and within which surface is located the targeting moiety, the nanoparticle device further characterised in that the therapeutic compound comprises LIF and the surface located targeting moiety comprises an antibody, or an antigen binding fragment of an antibody, that specifically binds to an antigen present on the cell surface of a stem cell having the capacity to act as a neural precursor cell.

In a particular embodiment of the invention the biodegradable carrier material degrades at a rate that allows for controlled release of the LIF over a pre-determined period of time. Suitably, the targeting moiety binds specifically to a Thy-1 antigen present on the surface of the stem cell. In a further embodiment the moiety binds specifically to a NCAM antigen present on the surface of the cell. In yet a further embodiment the moiety binds specifically to a GDNF receptor α1 (GDNFR-α1) located on the surface of the cell.

In an embodiment of the invention the nanoparticle device further comprises one or more of the following therapeutic compounds: brain-derived neurotrophic factor (BDNF) or an agonist thereof; epidermal growth factor (EGF) or an agonist thereof; glial cell-derived neurotrophic factor (GDNF) or an agonist thereof; retinoic acid and derivatives thereof; ciliary neurotrophic factor (CTNF) or an agonist thereof; Wnt5A.

In a particular embodiment of the invention the nanoparticle device has a diameter of at least about 50 nm and at most about 300 nm; optionally at least about 100 nm and at most about 200 nm.

A fifth aspect of the invention provides for a compositions or nanoparticle devices as described above for use in the treatment of NDD and CNS damage. According to a specific embodiment of the invention the compositions or nanoparticle devices are suitable for use in the treatment of one or more diseases selected from the group consisting of: Alzheimer's Disease (AD), Parkinson's Disease (PD); Huntington's Disease (HD); Frontotemporal dementia (FTD); and Amyotrophic Lateral Sclerosis (ALS).

A sixth aspect of the invention provides a composition for the treatment of NDD and CNS repair comprising:

a) a pharmaceutically acceptable carrier solution; and b) a plurality of biodegradable nanoparticles, wherein the nanoparticles comprise a targeting moiety that is able to bind selectively to the surface of a neural stem cell and/or a neural progenitor cell and wherein the nanoparticles further comprise XAV939.

A seventh aspect of the invention provides for a combinatorial composition for the treatment of NDD comprising:

a) a pharmaceutically acceptable carrier solution;

b) a first population of biodegradable nanoparticles, wherein the first nanoparticles comprise a targeting moiety that is able to bind selectively to the surface of a neural stem cell and/or a neural progenitor cell and wherein the first nanoparticles further comprise leukaemia inhibitory factor (LIF); and c) a second population of biodegradable nanoparticles, wherein the second population of nanoparticles comprise a targeting moiety that is able to bind selectively to the surface of a neural stem cell and/or a neural progenitor cell and wherein the second nanoparticles further comprise one or more of the compounds selected from: brain-derived neurotrophic factor (BDNF) or an agonist thereof; epidermal growth factor (EGF) or an agonist thereof; glial cell-derived neurotrophic factor (GDNF) or an agonist thereof; retinoic acid and derivatives thereof; ciliary neurotrophic factor (CTNF) or an agonist thereof; Wnt5A; and XAV939.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 3A shows a graph of results demonstrating that supplementing the medium with 0.1 ng/ml LIF significantly increased the number of dopaminergic neurons at 3 and 5 days in vitro. FIG. 3B shows exemplary immunocytochemistry images of E14 VM cultures after 5 days in vitro demonstrates the increased number of tyrosine hydroxylase positive neurons (highlighted) in cultures grown with 0.1 ng/ml LIF. The scale bar represents 100 μm.

FIGS. 13A-D show graphs indicating the response of lesioned recipient Lewis rats following transplantation of isogenic foetal VM cells treated with either empty nanoparticles, LIF nanoparticles or BDNF nanoparticles, or untreated cells.

DETAILED DESCRIPTION OF THE INVENTION

Figure 1A:
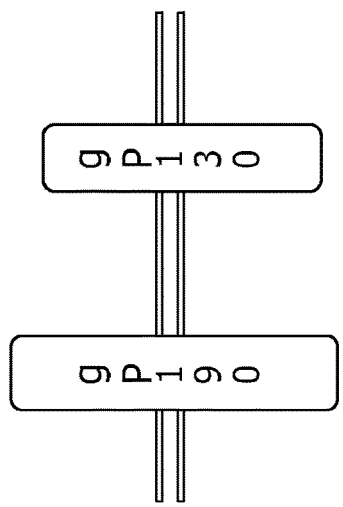
FIG. 1A shows a diagram of the LIF receptor consisting of two proteins: gp130 and gp190.

A description of example embodiments of the invention follows. A number of definitions are provided that will assist in the understanding of the invention. All references cited herein are incorporated by reference in their entirety. Unless otherwise defined, all technical and scientific terms used herein have the same meaning as commonly understood by one of ordinary skill in the art to which this invention belongs.

As used herein, the term "comprising" means any of the recited elements are necessarily included and other elements may optionally be included as well. "Consisting essentially of" means any recited elements are necessarily included, elements that would materially affect the basic and novel characteristics of the listed elements are excluded, and other elements may optionally be included. "Consisting of" means that all elements other than those listed are excluded. Embodiments defined by each of these terms are within the scope of this invention.

The term "antibody" as used herein denotes a protein that is produced in response to an antigen that is able to combine with and bind to the antigen, preferably at a specific site on the antigen, known as an epitope. The term as used herein includes antibodies of polyclonal and monoclonal origin, unless stated otherwise. Also included within the term are antigen binding fragments of naturally or non-naturally occurring antibodies, for example, the "Fab fragment", "Fab' fragment" (a Fab with a heavy chain hinge region) and "F(ab')2 fragment" (a dimer of Fab' fragments joined by a heavy chain hinge region).

The term "growth factor" as used herein denotes a naturally occurring substance capable of stimulating cellular growth, proliferation and differentiation. Growth factors are important for regulating a variety of cellular processes and typically act as signaling molecules between cells. Certain combinations of growth factors create gradients able to guide cell differentiation in a temporal and spatial manner.

The term "induced pluripotent stem cells" (IPS cells) as used herein denotes a type of pluripotent stem cell artificially derived from a non-pluripotent cell by inducing the forced expression of specific genes. Typically, the non-pluripotent cell is an adult somatic cell. IPS cells can be used to generate immuno-compatible cell types for cell based therapy, thereby avoiding the use of immune suppressive treatment.

The compositions and methods of the invention can be utilised with any stem cells that exhibit the capacity to act as a neural precursor cell or to differentiate into a neural stem cell. Such stem cells may be selected from one or more of the group consisting of: neural stem cells; neural progenitor cells; pluripotent stem cells; totipotent stem cells; embryonic stem cells (ESCs); induced pluripotent stem cell (iPSCs); ectodermal cells; precursor cells having commitment to a neurectodermal lineage; neural cells; and neuronal cells. In certain embodiments of the invention where the stem cells are ESCs, the ESCs may be derived from sources other than a human embryo.

The term "neural stem cells" (NSCs) as used herein denotes self-renewing multipotent cells that are capable of generating the main phenotypes of the nervous system, including neurons, astrocytes and oligodendrocytes.

The term "neural progenitor cells" (NPCs) as used herein denotes oligopotent cells that are at a further stage of differentiation compared to NSCs and are destined to differentiate into specific target cells.

The terms "induced neuron" (iN) and "induced dopaminergic cell" (iDA) and "induced oligodendrocyte" (iOD) are used to denote cells derived by transdifferentiation from differentiated somatic cell types usually fibroblastic in origin.

The invention provides nanoparticle-mediated delivery of compounds, such as growth factors, signalling proteins, cytokines and small molecules in novel combinations, as a novel means to repair damaged tissue in the CNS of an animal, such as a human. The clinical benefit is considerable for patients with neurodegenerative diseases or other tissue damage within the CNS including demyelinating injury. Compounds may be delivered individually or in combinatorial compositions, thereby allowing for synergistic therapeutic activity to be localised to the point of need in the recipient.

LIF is a member of the IL-6 family of cytokines, which are growth factors. LIF is a secreted signalling factor that binds to and signals via heterodimers of the LIF-specific receptor subunit, "gp190" and the signal-transducing receptor subunit "gp130". Downstream, intracellular signal propagation following LIF/LIF-R engagement occurs via both (i) the JAK/STAT pathway especially via the transcription factor STAT-3, and (ii) the MAPKinase pathway. Within the immune system there is an exquisite ability to discriminate between "self" and "non-self" that is orchestrated by antigen-specific T lymphocytes. Genomic plasticity enables differentiation of naive CD4+ T lymphocytes into either regulatory cells (Treg) that express the transcription factor Foxp3 and actively prevent auto-immune self-destruction, or effector cells (Teff) that attack and destroy their cognate target. Importantly, LIF supports Treg maturation in contrast to IL-6 which drives development of the pathogenic Th17 effector phenotype (Gao et al 2009 Cell Cycle). The inventors have previously demonstrated that nanoparticle-mediated targeted delivery of LIF can be used to guide tolerogenesis in a patient (see International (PCT) Publication No. WO 2009/053718, which is incorporated herein by reference).

Working in the CNS, the inventors made the unexpected discovery that nanoparticle-mediated targeted delivery of LIF to neural precursor has a profound protective effect that is markedly superior to that of soluble LIF. The cells were of the CNS where there is commitment to a neural cell fate, such as for neural stem cells, neural, neuronal oligodendrocyte and glial progenitor cells. This enables these nano-LIF-treated cell populations to be used therapeutically with unexpectedly high efficacy, such as in the treatment of NDD and other CNS conditions, In the CNS, LIF is thought to act predominantly as an injury factor, optimising the pool of neural precursors available for repopulation during repair (Pitman et al 2004, Mol Cell Neuroscience). LIF promotes neural stem cell self-renewal in the adult brain, regulating the emergence of more differentiated cell types, which ultimately leads to an expansion of the neural stem cell pool (Bauer, S. et al., 2006). LIF also stimulates the proliferation of parenchymal glial progenitors, in particular oligodendrocyte progenitor cells, through the activation of gp130 receptor signaling within these cells. This effect of LIF can be used to enhance the generation of oligodendrocytes and suggests that LIF has both reparative and protective activities that makes it a suitable candidate for the treatment of CNS demyelinating disorders and injuries (Deverman, B. E. et al., 2012). Furthermore, LIF has been shown to directly prevent oligodendrocyte death in animal models of multiple sclerosis, which is a disabling inflammatory demyelinating disease of the CNS, and this effect complements endogenous LIF receptor signalling, which already serves to limit oligodendrocyte loss during immune attack (Butzkueven, H. et al., 2002). LIF has also been shown to up-regulate the re-expression of NPCs in the brain of a Parkinson's Disease mouse model (Liu, J. et al., 2009).

However, when considering LIF as a potential therapeutic, it is important to note that LIF is tightly regulated in vivo under physiological conditions and that recombinant LIF (rLIF) administered systemically in high bolus doses is toxic. Low doses of rLIF are ineffective due to rapid degradation by serum proteases—part of the physiological control imposed on endogenous LIF in vivo.

In order to harness the immense therapeutic potential of LIF as a therapeutic within the CNS, the inventors have created a device that permits (i) specific targeting to sites of need within the CNS and (ii) provides low dose paracrine-type delivery of cargo sustained over several days or weeks, followed by complete degradation and elimination of the degradation products device including via CSF transit flow. Unexpectedly, by bringing the LIF-loaded nanoparticles into direct contact with cells surface receptors via the targeting moiety, the continuous low dose paracrine-type delivery of LIF achieves profound efficacy in promoting and protecting the CNS-derived cells as is shown in the Examples described herein.

In an embodiment of the invention, LIF-containing nanoparticles are provided that are capable of being targeted at neural stem cells and/or neural progenitor cells, in particular at specific markers located on the surface of these cells. The nanoparticles can be targeted to stem cells committed to or capable of following a neural lineage, including neural stem cells and neural progenitor cells in vitro (for example to test the nanoparticle efficacy and cytokine release rate, etc.), ex vivo (for later transplantation of LIF expanded neural cell populations into a patient) and/or in vivo (i.e. direct administration of nanoparticles into a patient requiring treatment for a neurodegenerative disorder).

The nanoparticle—also referred to as the nanoparticle device—suitably comprises a biodegradable non-toxic polymer that encapsulates LIF polypeptide (multiple cytokine polypeptides are typically encapsulated) either alone or in combination with one or more other factors. In this way the LIF represents a cargo load that is delivered by the nanoparticle. Suitably, the polymer comprises the copolymer poly(lactic)-co-glycolic acid (PLGA), which is an FDA approved biodegradable and biocompatible copolymer that allows for the slow release of LIF into the micro-environment of the target cell(s). PLGA undergoes hydrolysis (biodegrades) in the body to produce the original monomers, lactic acid and glycolic acid. It is possible to adjust the polymer degradation time by altering the ratio of these monomers in the PLGA copolymer. Hydrolysis of the polymeric matrix releases entrapped bioactive LIF in a sustained manner. Nanoparticulate devices and compositions are described in US-2010/0151436, which is incorparated herein by reference.

Alternatively, the nanoparticle polymer may comprise a combination of PLGA and poly(lactic acid) (otherwise known as polylactide—PLA). PLA is biodegradable thermoplastic aliphatic polyester derived from renewable resources. The ratios of PLGA and PLA can be varied to provide optimal delivery of LIF to neural stem cells and/or neural progenitor cells. The ratios can also be varied depending on whether the nanoparticles are to be delivered in vitro, ex vivo or in vivo.

The above-described polymers have several features that make them ideal materials for use in the nanoparticles of the present invention: 1) control over the size range of the nanoparticles, an important feature for ensuring that the nanoparticles can pass through biological barriers (such as the blood brain barrier) when used in active therapy (i.e. in vivo delivery of nanoparticles to CNS and brain tissue); 2) reproducible biodegradability without the necessary addition of enzymes or cofactors; 3) capability for temporal and special control of sustained release of encapsulated, protected neurally active factors (such as LIF) that may be tuned in the range of days to months by varying factors such as the PLGA to PLA copolymer ratios; 4) well-understood fabrication methodologies that offer flexibility over the range of parameters that can be used for fabrication, including choices over the polymer material, solvent, stabiliser, and scale of production; 5) control over surface properties facilitating the introduction of modular functionalities into the surface; and 6) the polymers are impermeable to serum proteases.

The nanoparticles of the invention are typically sized at least 50 nm (nanometres), suitably at least approximately 100 nm and typically at most 200 nm, although suitably up to 300 nm in diameter. In one embodiment of the invention the nanoparticle device has a diameter of approximately 100 nm. This is so that they are below the threshold for reticuloendothelial system (mononuclear phagocyte system) clearance, i.e. the particle is small enough not to be destroyed by phagocytic cells as part of the body's defence mechanism.

The nanoparticle device of the invention may suitably deliver the encapsulated cargo over a period of time that may be controlled by the particular choice or formulation of the encapsulating biodegradable non-toxic polymer or biocompatible material. One exemplary temporal release profile comprises a pulse of LIF release—characterized by release of up to 50% by weight of the amount of the cargo—associated with the nanoparticulate device in 1-5 days following the introduction into a subject. Following the pulse, the residual amount is slowly released over an extended period of time (e.g., 1, 2, 3, 4, 5, 6, 7, 8, 9, 10, 12 days or 2, 3, 4, 5 or more weeks) following the pulse period. In another embodiment of the invention the initial pulse may be reduced to less than 50% of the amount of the cargo, less than 30% or even less than 10% by weight of the total cargo. Likewise, the device may be configured so as to only deliver the cargo over a sustained period of time of 1, 2, 3, 4, 5, 6, 7, 8, 9, 10, 12 days, 2, 3, 4, 5 or more weeks, or up to six months. It will be appreciated that the release profile will be best optimised to suit the clinical needs of the patient and the particular NDD that is being treated.

Targeting of the nanoparticles to a specified cell surface marker on the cell of choice, for example a neural stem cell and/or a neural precursor cell, is typically achieved by locating a targeting moiety, such as an antibody, on the surface of the nanoparticle. The targeting moiety is able to bind selectively to the cell of choice via affinity-targeted ligand interactions, Cell-specific targeting is achieved by the choice of surface-bound antibody. Thus, the nanoparticles of the invention further comprise a surface exposed antibody that specifically binds to the cell of choice. Suitable targeting moieties include monoclonal antibodies, polyclonal antibodies, antigen binding antibody fragments, ligands, and small molecules. Suitable antibody fragments or derivatives from a variety of sources may include: $F_{ab}$, $scF_v$, Bis-$scF_v$, $V_H$, $V_L$, V-NAR, VhH or any other antigen-binding single domain antibody fragment. The specific binding activity may also be localised within another antibody-like affinity binding protein including lactoferrins, cathelicidins, ficolins, collagenous lectins and defensins.

The nanoparticle polymer can suitably be decorated with functional avidin or streptavidin groups on the nanoparticle surface to enable modification of the surface through the robust attachment of biotinylated ligands such as specific cell-targeting antibodies.

The Thy-1 antigen (Reif and Allen, 1964) has been identified as one suitable target to localise nanoparticles of the invention to the surface of neural stem cells and neural progenitor cells. It may be beneficial to target the nanoparticles to the Thy-1 antigen rather than a cell surface receptor so as to avoid any potential interference of receptor function of the target cell. Thy-1 (also known as CD90—Cluster of Differentiation 90) is a 25-37 kDa heavily N-glycosylated, glycophosphatidylinositol anchored conserved cell surface protein with a single V-like immunoglobulin domain. It can be used as a marker for a variety of stem cells, including neural stem cells, and for the axonal processes of mature neurons. T lymphocytes also express Thy-1 on their cell surface. The co-targeting of the nanoparticles of the invention to neural committed stem cells, neural progenitor cells and additionally T lymphocytes is of great benefit when using the nanoparticles to expand and protect a population of neural stem cells and/or neural progenitor cells ex vivo for transplantation into a subject. T lymphocytes mature towards $T_{reg}$ under the influence of LIF so that, when the time comes for cell transplantation, a population of the transplanted cells treated with nanoparticles of the invention will be surrounded by an artificial stroma comprising, for example, LIF-containing nanoparticles that promote both cell survival and repress adverse immune reactions to enhance engraftment of transplanted cells in the CNS. Thus, in one embodiment of the invention, LIF's neurogenic and tolerogenic dual characteristics make it an ideal choice of factor for endogenous support of brain repair and suppression of inappropriate immune activity and a profound synergistic effect is provided by the LIF encapsulated nanoparticles.

The link between IL6, a potent inducer of pathogenic inflammatory TH17 lymphocytes and neurodegenerative disease progression is of further relevance, since the inventors have found that LIF directly suppresses both IL6 activity and TH17 cell development and instead promotes tolerogenic $T_{reg}$ cells (Gao et al 2009; Park et al 2011). This correlates with the recent finding that $T_{reg}$ opposes TH17-driven dopaminergic neurodegeneration in a mouse model of Parkinson's Disease (Reynolds et al 2010); and that LIF opposes pathogenic TH17 cells in an experimental allergic encephalitis (EAE) model of multiple sclerosis, a demyelinating disease of the CNS (Cao et al 2011).

It will be appreciated by the skilled person that other alternative cell surface markers may be used for targeting nanoparticle devices of the invention to neural stem cells and neural progenitor cells, or other pluripotent cells having the capacity to differentiate into neural cells. By way of non-limiting example, one alternative target is the glial cell line derived neurotrophic factor receptor α1 (GDNF-R α1). Hence, in specific embodiments of the invention if Thy-1 is the target cell surface marker the nanoparticle may comprise an anti-Thy-1 antibody in its surface. Likewise, if GDNF-R α1 is the target cell surface marker the nanoparticle may comprise an anti-GDNF-R α1 antibody on its surface.

The nanoparticles of the invention enable the sustained delivery of factors, such as multiple LIF molecules, to ensure a relatively high concentration of factor precisely within the microenvironment of the targeted cells to expand and protect the cells, whilst avoiding toxic systemic exposure of the recipient subject to the therapeutic cytokine.

In an embodiment of the invention, the nanoparticles are suspended in a biocompatible solution to form a composition that can be targeted to a location on a cell, within a tissue or within the body of a patient or animal (e.g. the composition can be used in vitro, ex vivo or in vivo). Suitably, the biocompatible solution may be phosphate buffered saline or any other pharmaceutically acceptable carrier solution. One or more additional pharmaceutically acceptable carriers (such as diluents, adjuvants, excipients or vehicles) may be combined with the nanoparticles of the invention in a pharmaceutical composition. Suitable pharmaceutical carriers are described in "Remington's Pharmaceutical Sciences" by E. W. Martin. Pharmaceutical formulations and compositions of the invention are formulated to conform to regulatory standards and can be administered orally, intravenously, topically, or via other standard routes. Administration can be systemic or local or intranasal or intrathecal.

In further embodiments of the invention, other growth factors, signalling proteins and small molecules may be encapsulated within the nanoparticles either in addition to or instead of LIF to expand, protect and/or differentiate neural stem cells, neural progenitor cells or other pluripotent cells having the capacity to differentiate into neural cells. The provision of other factors and/or molecules in addition to LIF may augment the efficacy of LIF or the tolerogenic effect of the composition when used in vivo.

Other potential neurogenic and/or neuroprotective agents for encapsulation in nanoparticles include growth factors such as brain-derived neurotrophic factor (BDNF), the BDNF-agonist 7,8 dihydroxy flavone (7,8-DHF) epidermal growth factor (EGF), glial cell-derived neurotrophic factor (GDNF), ciliary neurotrophic factor (CTNF), amongst others, retinoic acid (RA) and derivatives thereof, and the signalling protein Wnt5A. Derivatives of retinoic acid may include, but are not limited to, 9-cis RA, 13-cis RA, N-(4-hydroxyphenyl) retinamide (4-HPR), and all-trans retinoic acid (ATRA). Agonists of neural growth factors can also be encapsulated in the nanoparticles. By way of example, the BDNF agonist 7,8 dihydroxyflavone (7,8,DHF) is shown in the present Examples to increase the yield of TH+ neuronal cells in primary rat E14 VM tissue treated with nanoparticles that encapsulate the agonist. Optional additional factors, such as anti-oxidants, or transforming growth factor beta (TGF-β) that promotes responsiveness to GDNF, or retinoic acid that plays an important role in multipotency, may also be included in the nanoparticles. Single or multiple agents may be combined with LIF in the same nanoparticle, or may be used individually in one nanoparticle, for nanoparticle delivery to target cells.

Taking EGF as an example, this growth factor has a unique role as a mediator of dopamine-induced precursor cell proliferation in the sub-ventricular zone of the brain. EGF receptors are reduced in Parkinson's Disease, therefore targeted paracrine delivery of nanoparticles containing EGF can increase dopamine-induced precursor cell proliferation due to the increase in EGF potency.

Wnt5a (Wingless-type MMTV integration site family member 5A) is a signaling protein that in humans is encoded by the WNT5A gene. Members of the Wnt5a class of proteins activate non-canonical Wnt pathways, which involve different kinases such as protein kinase C, calmodulin-dependent protein kinase II and c-Jun N-terminal kinase, as well as phosphatases and GTPases. Non-canonical Wnt pathways inhibit the canonical Wnt-β-catenin pathway. Human frizzled-5 (hFz5) is a receptor for the human Wnt5A protein. Wnt5A has been implicated as a tumour suppressor gene. Importantly, Wnt5A has been identified for use in the treatment of primary midbrain precursor cells to induce their differentiation into dopaminergic (DA) neurons. Therefore, sustained nanoparticle delivery of Wnt5a (either with or without LIF) to dopaminergic precursor cell populations will support DA cell differentiation in addition to increasing dopaminergic precursor cell recovery ex vivo and also their survival following subsequent transplantation into patients suffering from Parkinson's Disease.

In an embodiment of the invention the nanoparticles may also comprise as the cargo—in addition to or instead of LIF—the small molecule XAV939 (structure shown below).

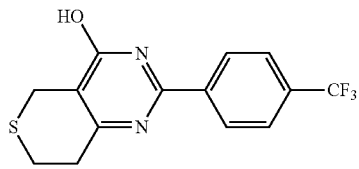 [SMILES: Oc1nc(-c2ccc(C(F)(F)F)cc2)nc2c1CSCC2]

XAV939 is a known inhibitor of the Wnt/β-catenin signalling pathway that mediates β-catenin degradation by inhibiting the poly-ADP-ribosylating enzymes tankyrase 1 and tankyrase 2, which in turn stabilises axin. Both tankyrase isoforms interact with a highly conserved domain of axin and stimulate its degradation through the ubiquitin-proteasome pathway (Huang et al., 2009). Importantly, XAV939 promotes remyelination of demyelinated nerve axons by stabilising Axin2. Axin2 itself is regulatory and provides a therapeutic target in new born brain injury and for remyelination. Axin2 is expressed in immature oligodendrocyte precursor cells (OPC), including those residing in active MS lesions. Axin2 plays a role in feedback regulation of the wnt signalling pathway: since wnt signalling can act to inhibit OPC differentiation in both adult remyelination models and developmental myelination, manipulation of Axin2 levels in OPC can repress wnt signalling and promote accelerated differentiation of OPC to oligodendrocytes (OD) capable of remyelinating nerve axons within the CNS. By inhibiting tankyrase, involved in Axin2 degradation, XAV939 promotes remyelination (Fancy et al. 2011). Direct injection of XAV939 direct into spinal cord lesions promotes markedly accelerated OD differentiation after demyelinating injury. Hence, the nano-XAV939 device of the present invention targeted to the surface of, for example, demyelinated axons provides a non-invasive focussed means of simarly promoting remyelination.

The nanoparticles and compositions of the invention can be delivered to target cells in vitro, for example to test their efficacy, and also ex vivo for the transplantation of LIF expanded and/or protected target cells into the adult brain of patients suffering from neurodegenerative disease. Cell therapy promotes brain repair by maintaining or replacing populations of vulnerable neurons and/or expanding the endogenous neural stem cells and progenitor cells that populate the brain, providing an enriched source of healthy precursor cells with the potential to mediate repair. Cell therapy can provide precursor cells as autografts (for example, derived from patient skin fibroblasts by trans-differentiation to a required phenotypic precursor cell—IPS cell) or allografts (for example, from foetal precursor cells). In an embodiment of the invention the transplanted cells may be dopaminergic cells.

The nanoparticles and compositions of the invention can also be delivered to target cells in vivo. In vivo use requires that the nanoparticles of the invention are able to cross the blood brain barrier so that they can access the target cells within the brain of the patient. Self-administered intra-nasal delivery of the nanoparticles and compositions of the invention is one way in which the nanoparticles can reach the target cells to promote endogenous repair and replacement of damaged brain tissues, and to protect healthy brain structure from toxic damage associated with disease states.

The nanoparticles and compositions of the invention can be used in the treatment of various neurodegenerative diseases, including Alzheimer's Disease, Parkinson's Disease, Amyotrophic lateral sclerosis and Huntington's Disease, amongst others, and will provide huge socio-economic benefit to patients suffering from neurodegenerative diseases and their families. By way of example, dopaminergic cell replacement therapy is the focus for the treatment of Parkinson's Disease.

IPS cells are an alternative source of cells for therapy and the nanoparticles and compositions of the invention can be targeted to IPS cells to expand, protect and/or differentiate these cells for use in cellular therapy in the treatment of NDD and CNS trauma. Likewise the nanoparticle devices of the invention may be used to expand or admix with stem cell preparations ex-vivo prior to introduction into a subject. In such an embodiment of the invention the stem cells may be adult derived, foetal-derived, derived from IPS cells, or from any other allogenic The invention further provides for combinatorial compositions that comprise mixtures of populations of nanoparticles that comprise more than one therapeutic agent per nanoparticle, or different nanparticles each comprising a different therapeutic agent, for the treatment of neurodegenerative disease. Such combinatorial compositions may suitably comprise a pharmaceutically acceptable carrier solution; at least a first population of biodegradable nanoparticles, wherein the first nanoparticles comprise a targeting moiety that is able to bind selectively to the surface of a neural stem cell and/or a neural progenitor cell and wherein the first nanoparticles further comprise leukaemia inhibitory factor (LIF); and at least second population of biodegradable nanoparticles, wherein the second population of nanoparticles comprise a targeting moiety that is able to bind selectively to the surface of a neural stem cell and/or a neural progenitor cell and wherein the second nanoparticles further comprise one or more other than LIF. Suitably, the second nanoparticles may comprise compounds selected from: brain-derived neurotrophic factor (BDNF); epidermal growth factor (EGF); glial cell-derived neurotrophic factor (GDNF); ciliary neurotrophic factor (CTNF); retinoic acid, and derivatives thereof; Wnt5A; and XAV939.

The invention is further exemplified in the following non-limiting examples.

EXAMPLE 1

Figure 1B:
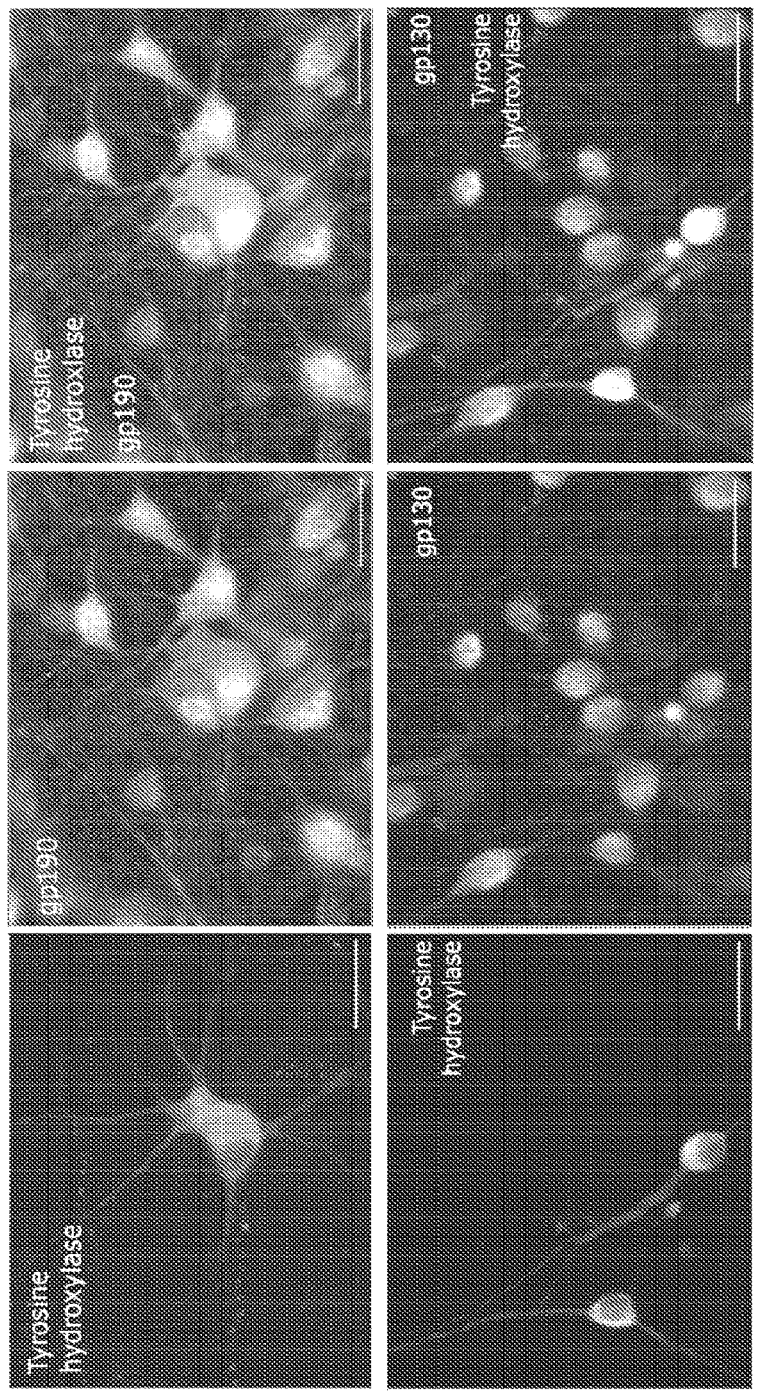
FIG. 1B shows Immunocytochemistry of 5 day old E14 VM cultures with antibodies against tyrosine hydroxylase and gp130 or gp190 demonstrating that dopaminergic neurons express gp130 and gp190.

1.1 Dopaminergic Neurons Derived from E14 Ventral Mesencephalon (VM) from Rat Foetuses Express the Components of the LIF Receptor Complex The expression of gp130 and gp190, the two components of the LIF receptor complex (FIG. 1A), on dopaminergic neurons of embryonic day 14 ('E14') VM was analysed via immunocytochemistry of E14 VM cultures after 3 days in vitro ('DIV') (FIG. 1B). FIG. 1B shows that both components of the LIF receptor complex are expressed by dopaminergic neurons in E14 ventral mesencephalon (VM) cultures. FIG. 1A: The LIF receptor is a heterodimer consisting of two proteins: gp130 and gp190. FIG. 1B: Immunocytochemistry of 5 day old E14 VM cultures with antibodies against tyrosine hydroxylase and gp130 or gp190 demonstrated that dopaminergic neurons express gp130 and gp190. Dopaminergic neurons were demonstrated to express both gp130 and gp190, suggesting a potential for responsiveness to LIF treatment.

Figure 2:
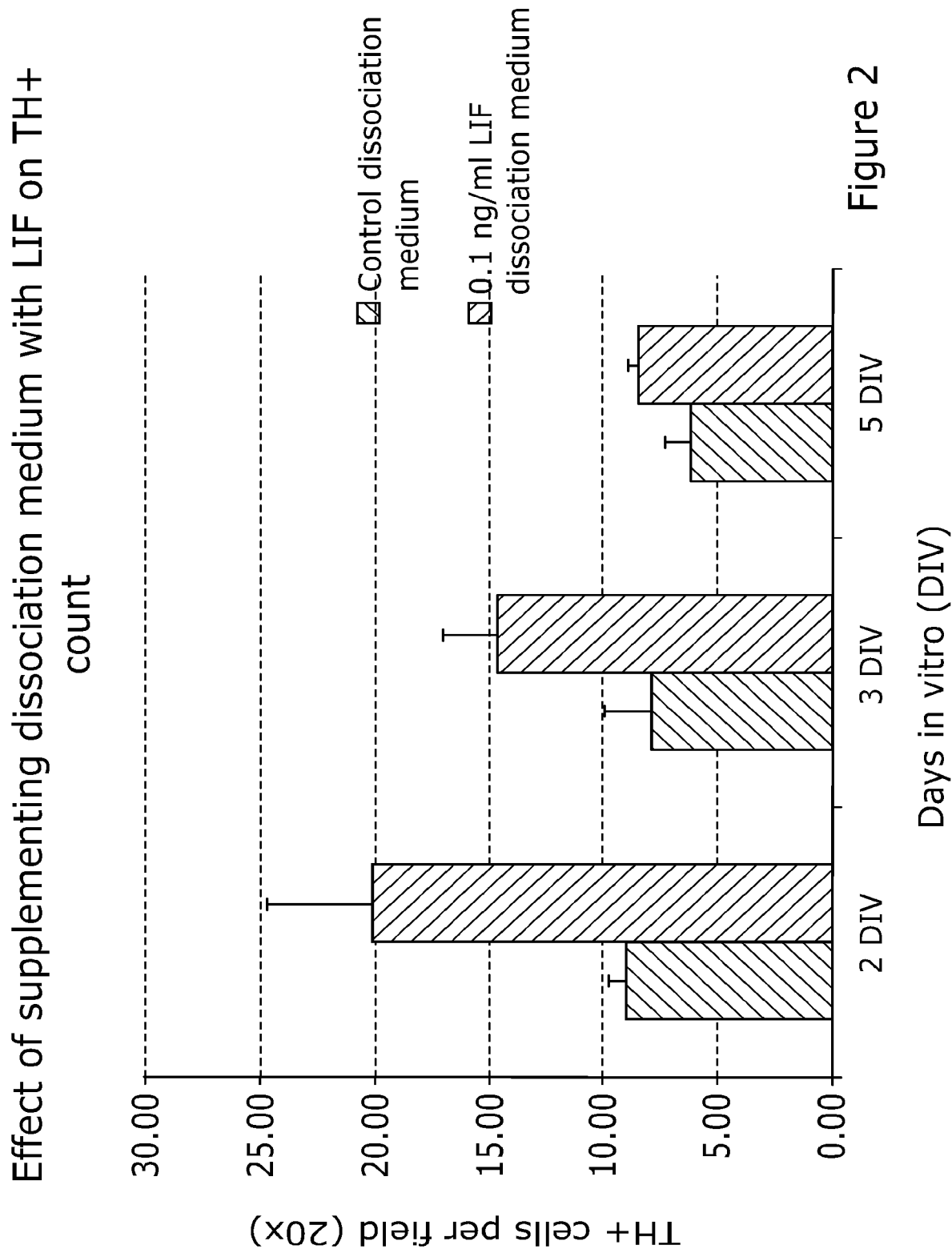
FIG. 2 shows a graph indicating that dissociation of E14 VM tissue in LIF supplemented medium increases the number of dopaminergic neurons in subsequent monolayer culture. Isolated ventral midbrain tissue from E14 rat foetuses was dissociated in growth medium alone or medium supplemented with 0.1 ng/ml LIF.

1.2 LIF Treatment During Tissue Dissociation Increases the Subsequent Number of Dopaminergic Neurons The VM of E14 rat foetuses was dissected and dissociated in medium with or without 0.1 ng/ml soluble LIF. The tissue was then plated in monolayer culture and grown for 2, 3 or 5 days prior to fixing. Dissociated cells were seeded in monolayer cultures and fixed after 2, 3 or 5 days in vitro (DIV). Culture derived from cells dissociated in LIF supplemented medium were found via immunocytochemical analysis to contain significantly more tyrosine hydroxylase positive neurons after 2 days in vitro but not later time points. Subsequent immunocytochemistry of fixed culture demonstrated that cultures derived from tissue dissociated in the presence of 0.1 ng/ml LIF had significantly more TH+ neurons after 2 days in vitro; this effect was lost at 3 and 5 days in vitro (FIG. 2).

Figure 3A:
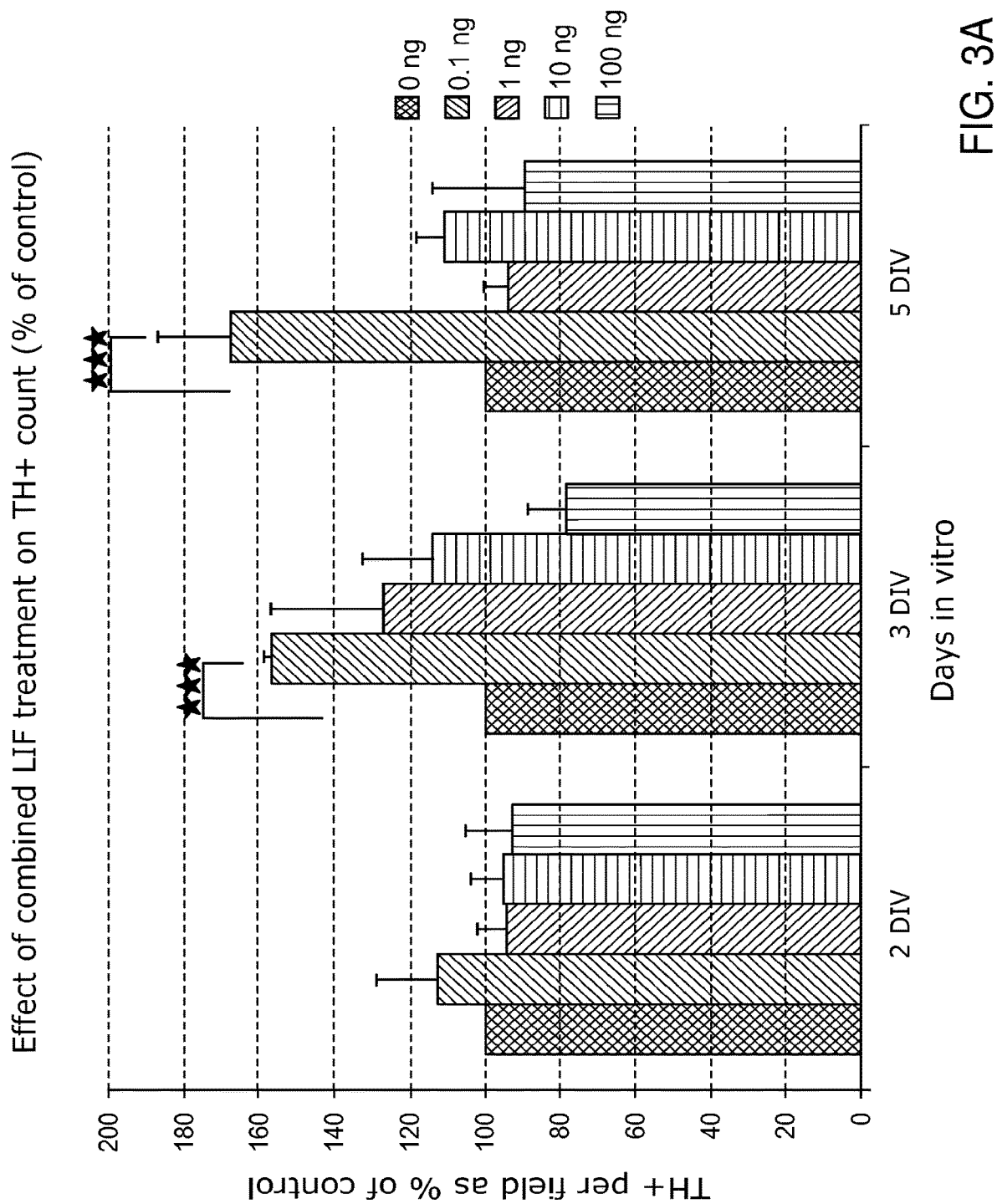
FIG. 3A and FIG. 3B show that supplementing growth medium with 0.1 ng/ml LIF increases the dopaminergic cell count at 3 and 5 days in vitro.
Figure 3B:
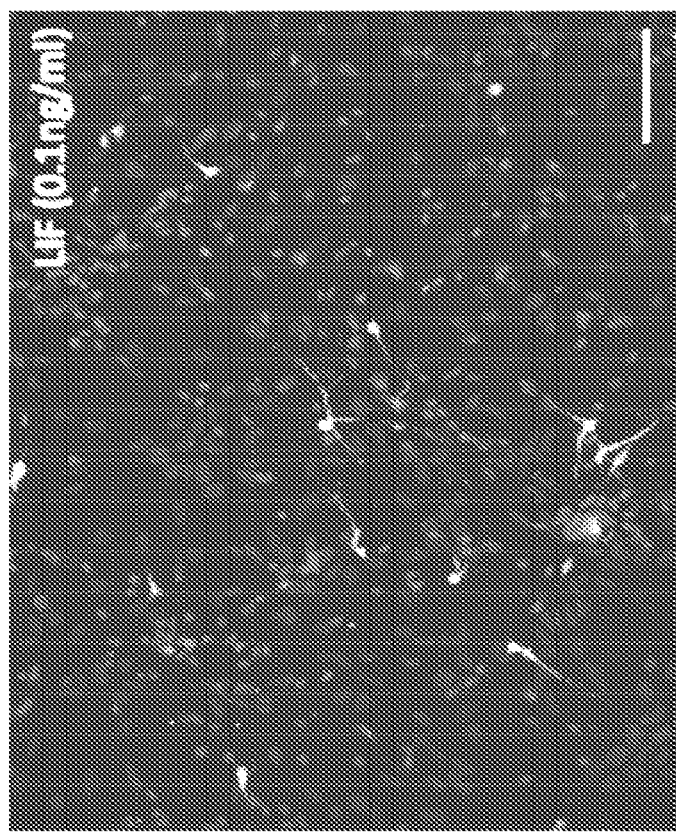
Figure 3B:
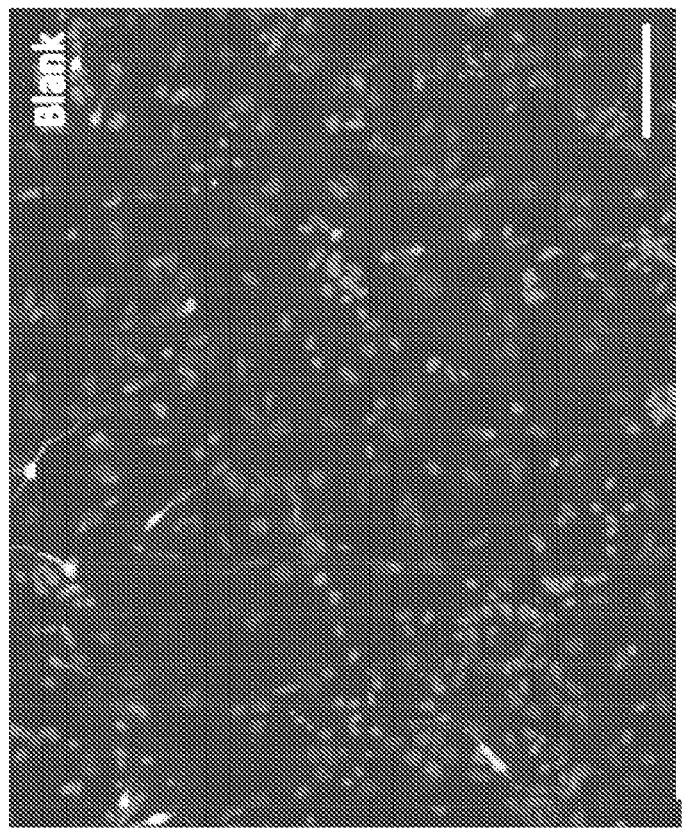

1.3 Dopaminergic Cell Count in E14 VM Cultures can be Increased by Supplementing Growth Medium with 0.1 ng/ml Soluble LIF The VM of E14 rat foetuses was dissected and dissociated in standard conditions. Primary E14 VM tissue was dissociated and grown as monolayer cultures. After plating cells were chronically treated with soluble LIF in their growth medium ranging from 0.1 ng/ml to 100 ng/ml. Subsequent immunocytochemistry demonstrated that supplementation of growth medium with 0.1 ng/ml LIF was able to significantly increase the number of tyrosine hydroxylase positive neurons after 3 and 5 days in vitro (FIG. 3A and FIG. 3B). Treatment of E14 VM cultures with all LIF dosages above 0.1 ng/ml had no significant effect on the number of TH positive neurons.

1.4 Dopaminergic Neurons Express the Glial Cell Line Derived Neurotrophic Factor Receptor α1

Figure 4:
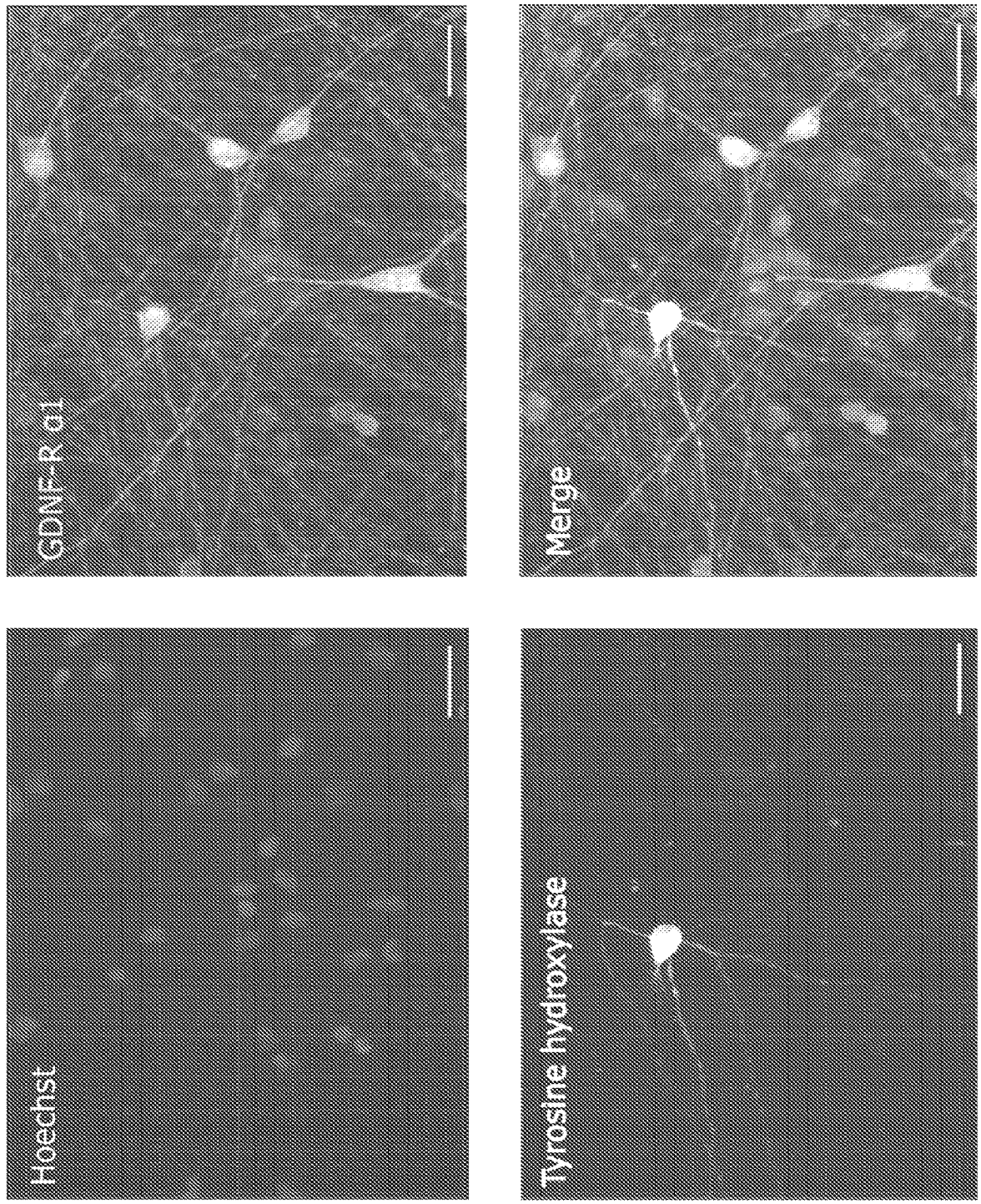
FIG. 4 shows micrographs indicating that dopaminergic neurons in E14 VM cultures express the GDNF receptor α1. The scale bar represents 25 μm.

Before the effect of nanoparticle treatment on E14 VM cultures could be investigated it was necessary to identify a cell surface protein that could be used as a target for antibodies on the nanoparticle surface. Given the known neurotrophic effect of glial cell line derived neurotrophic factor ('GDNF') on dopaminergic neurons the expression of the GDNF receptor α1 ('GDNF-R α1') in E14 VM cultures was analysed via immunocytochemistry with the aim of potentially using this protein as a nanoparticle target. The monolayer culture was fixed after 5 days in vitro and analysed for expression of GDNFR-α1 through immunocytochemistry. Dual staining with tyrosine hydroxylase demonstrated that individual neurons express both TH and GDNFR-α1. Hence, as expected, dopaminergic neurons were found to express this protein (FIG. 4).

Figure 5A:
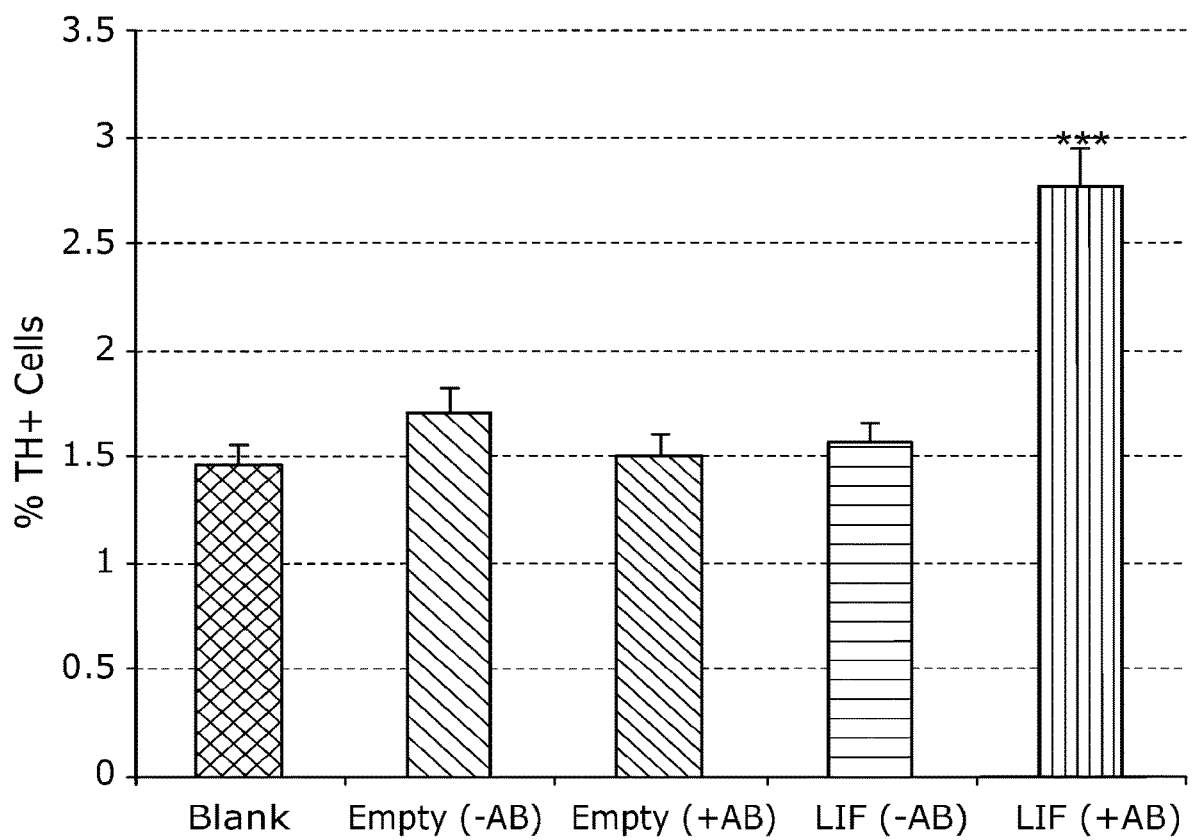
FIG. 5A shows a graph and FIG. 5B shows immunocytochemistry indicating that treatment of E14 VM cultures with nanoparticles targeted to the GDNF receptor α1 increases the dopaminergic cell count at 3 days in vitro.
Figure 5B:
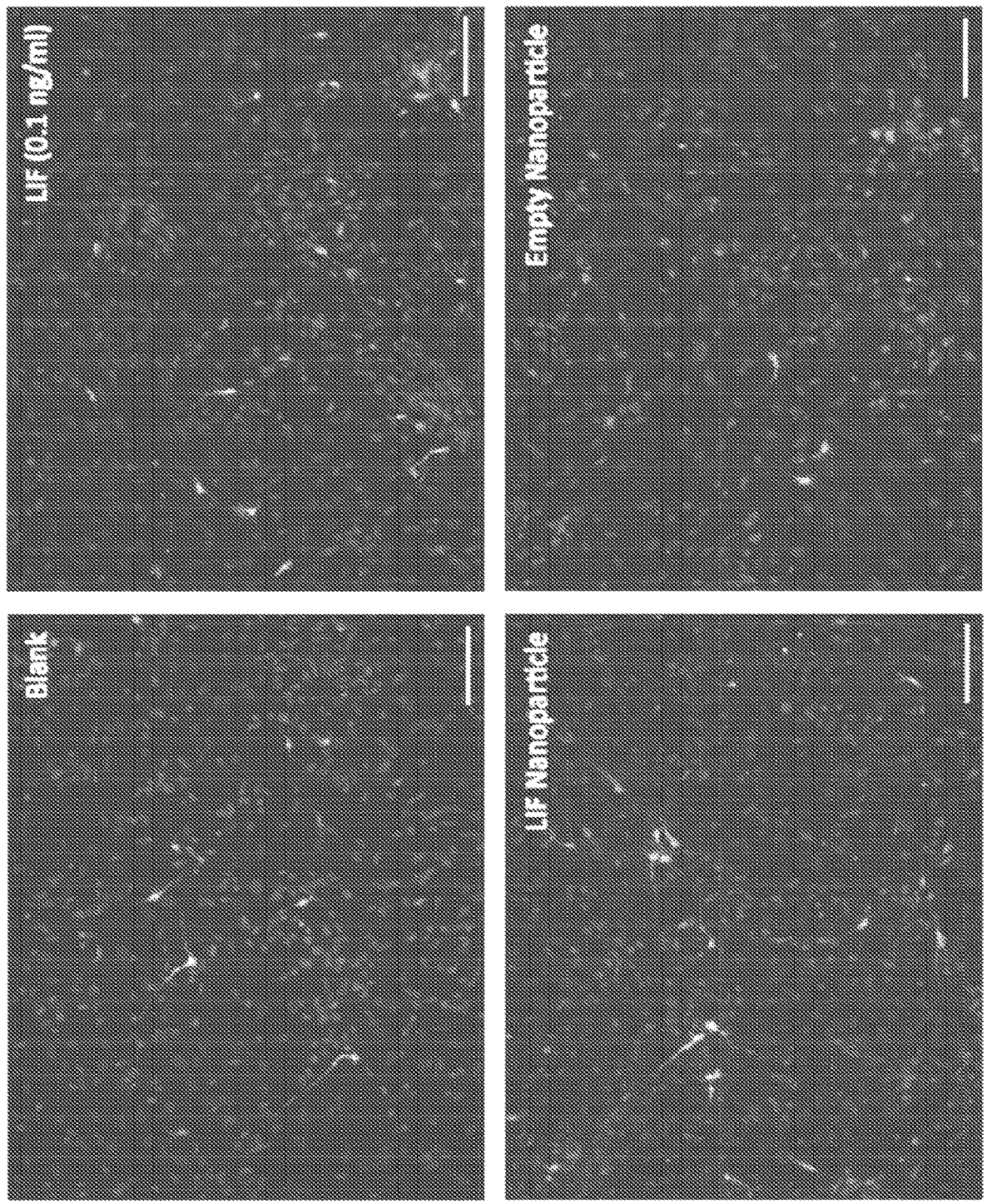

1.5 LIF Nanoparticles Targeted via Antibodies Against GDNF-R α1 Increase the Tyrosine Hydroxylase Positive Cell Count in E14 VM Cultures To investigate the effect of LIF nanoparticle treatment on tyrosine hydroxylase positive cell counts, primary E14 VM was mixed with LIF nanoparticles (targeted or non-targeted) or empty nanoparticles (targeted or non-targeted) immediately prior to plating in monolayer culture. E14 VM tissue was mixed with 100 μl of a 1 mg/ml nanoparticle solution immediately prior to plating. Nanoparticles were either empty nanoparticles (with or without surface bound anti-GDNFR-α1 antibodies) or LIF nanoparticles (with or without anti-GDNFR-α1 antibodies). Immunocytochemical analysis of these cultures after 3 days in vitro revealed a significant increase in the number of tyrosine hydroxylase positive neurons in the cultures treated with targeted LIF nanoparticles. Cultures were fixed after 3 days in vitro and analysed via immunocytochemistry for tyrosine hydroxylase. Plating cells with targeted LIF nanoparticles significantly increased the TH positive cell count at 3 days in vitro Non-targeted LIF nanoparticles and empty nanoparticles had no effect on the TH+ cell count (FIG. 5A and FIG. 5B).

Figure 6A:
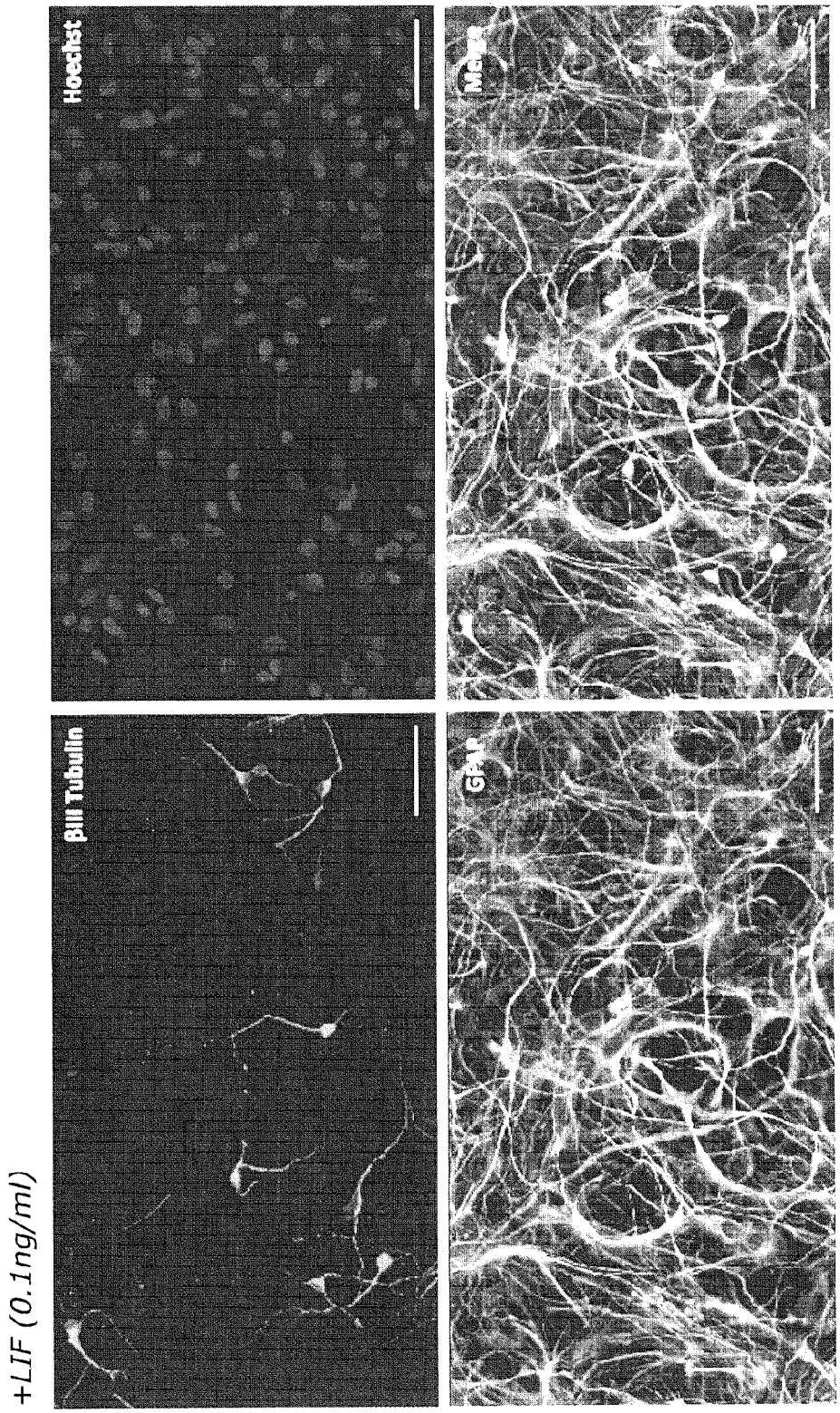
FIGS. 6A and 6B show micrographs indicating that for monolayer cultures derived from E14 VM cells previously expanded as neurospheres immunocytochemical analysis revealed presence of immature neurons (βIII tubulin) and astrocytes (GFAP). The scale bars represent 50 μm.
Figure 6B:
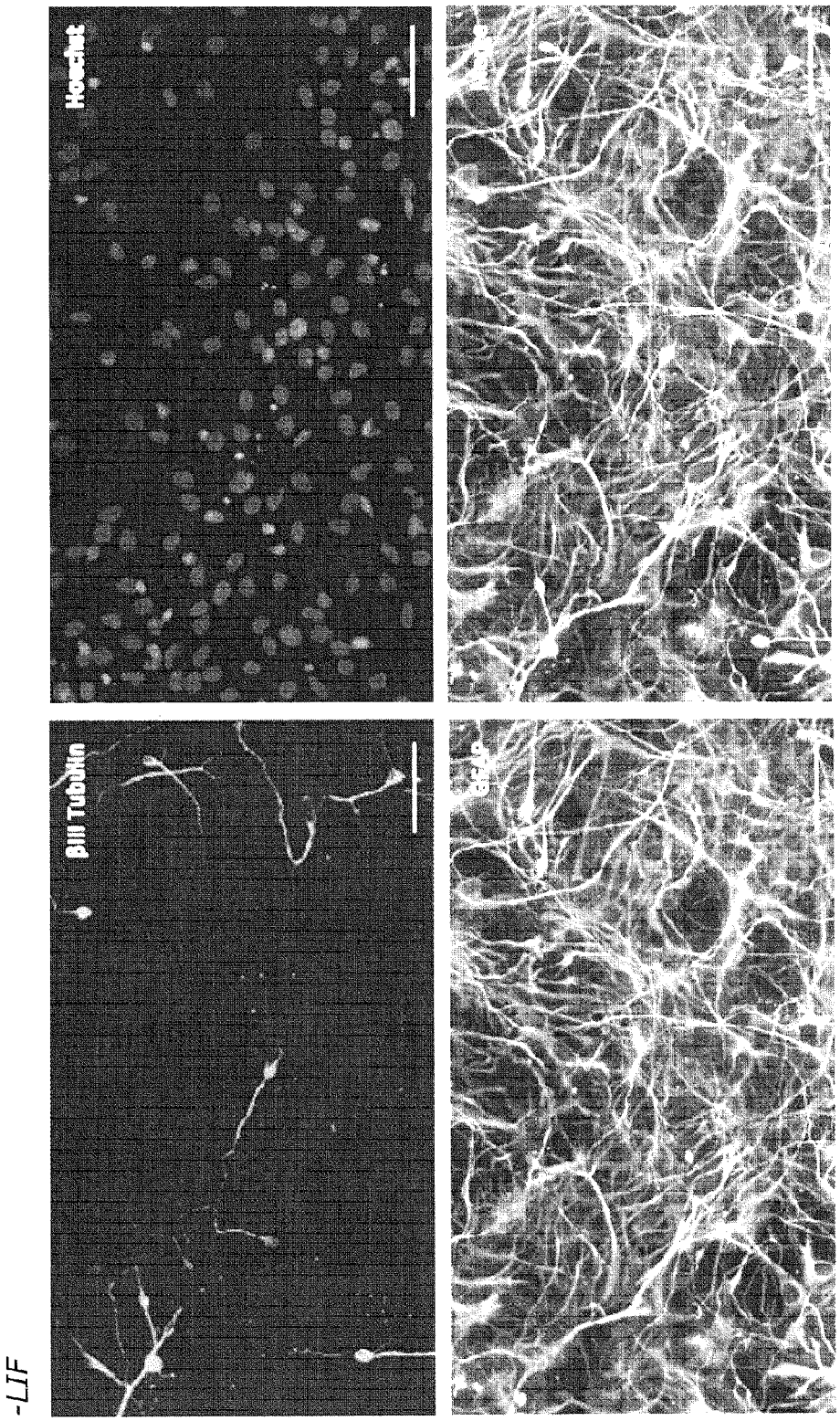
Figure 7:
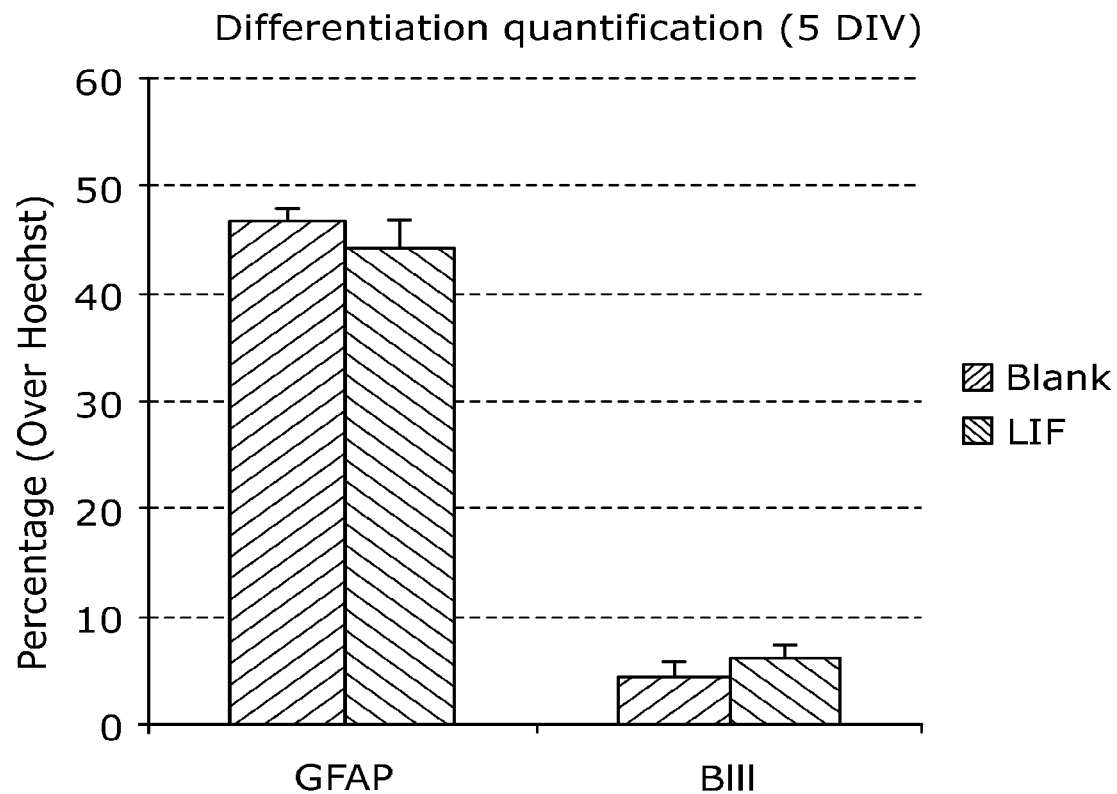
FIG. 7 shows graphs that indicate that expansion of E14 VM neural progenitor cells with 0.1 ng/ml LIF has no impact on subsequent differentiation. Expansion of E14 VM as neurospheres in medium supplemented with 0.1 ng/ml LIF had no significant effect on subsequent levels of neural or astroglial differentiation in monolayer cultures produced from dissociated neurospheres.
Figure 7:
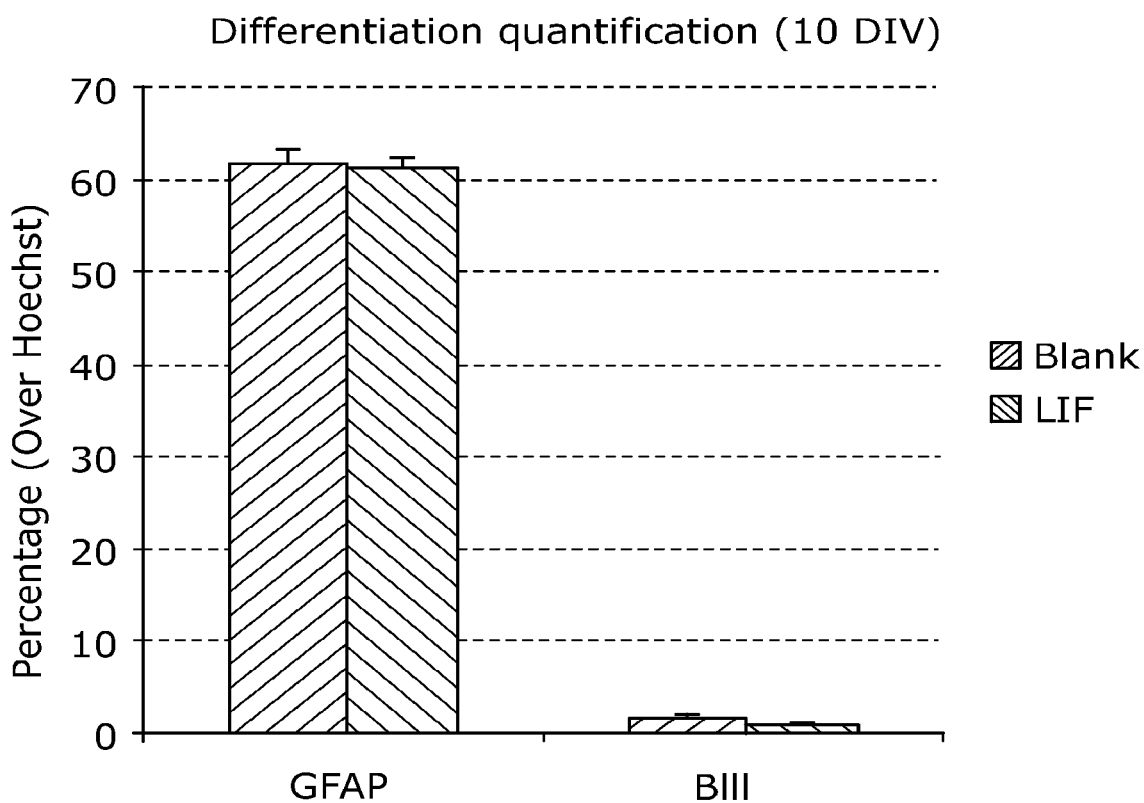

1.6 Treatment of E14 VM Derived Neurospheres with 0.1 ng/ml Soluble LIF has No Effect on Subsequent Differentiation in Monolayer Culture To investigate the effect of LIF treatment on the differentiation of E14 VM, tissue was grown as neurospheres in expansion medium with or without 0.1 ng/ml soluble LIF. Primary ventral midbrain tissue was expanded in medium containing the mitogens EGF and FGF-2 for 5 days. These neurospheres were then dissociated into single cells and plated in monolayer culture in the absence of LIF. After 5 days of growth these cultures were analysed via immunocytochemistry for neural and astroglial differentiation (FIGS. 6A and 6B, showing morphology + or − LIF). The presence of LIF during the expansion of E14 VM had no effect on subsequent differentiation (FIG. 7 showing results after 5 and 10 days).

Figure 8A:
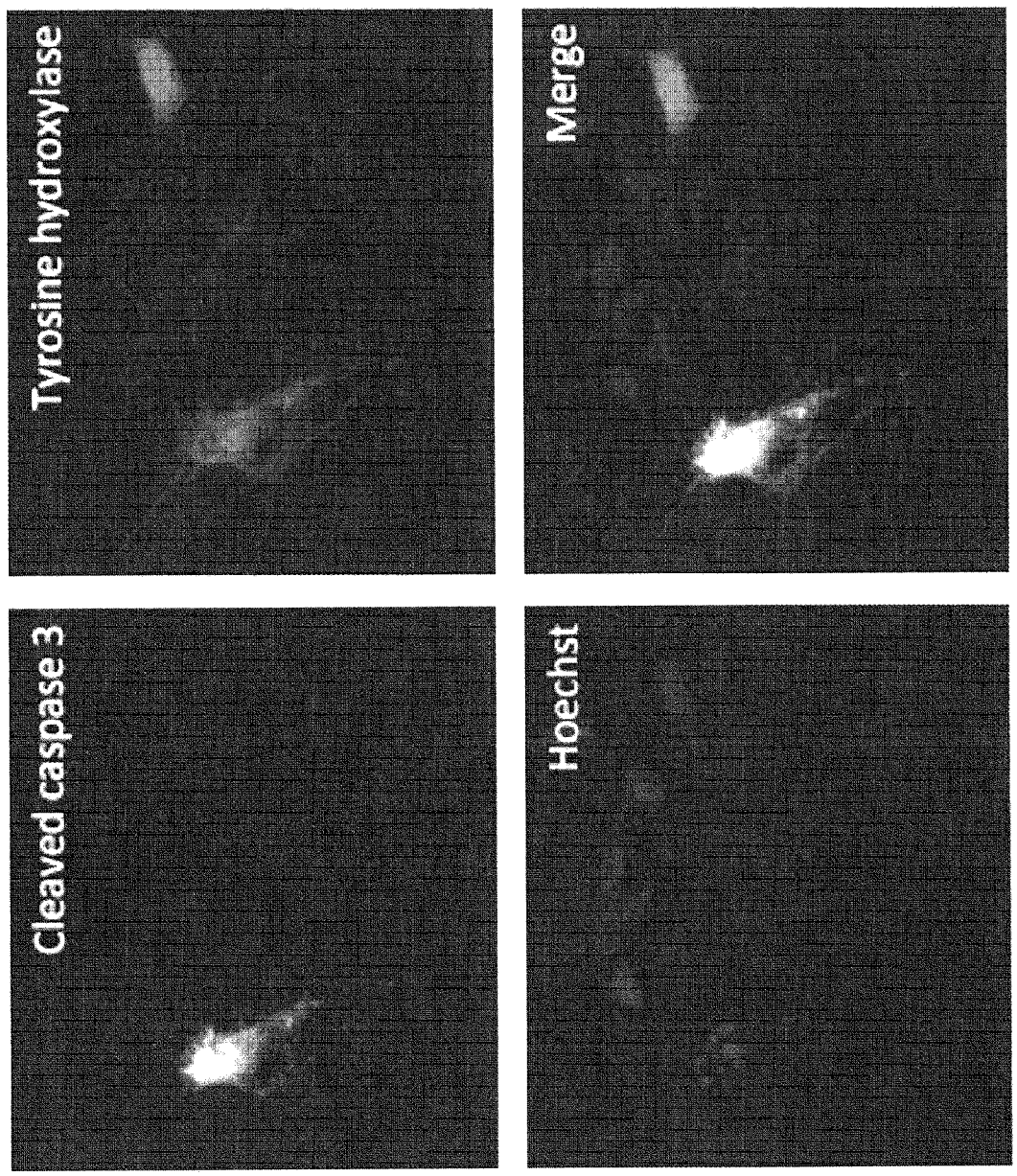
FIGS. 8A and 8B show micrographs indicating that a proportion of dopaminergic neurons in E14 VM cultures undergo apoptosis. E14 VM cultures were fixed after 2 days in vitro and analysed via immunocytochemistry.
Figure 8B:
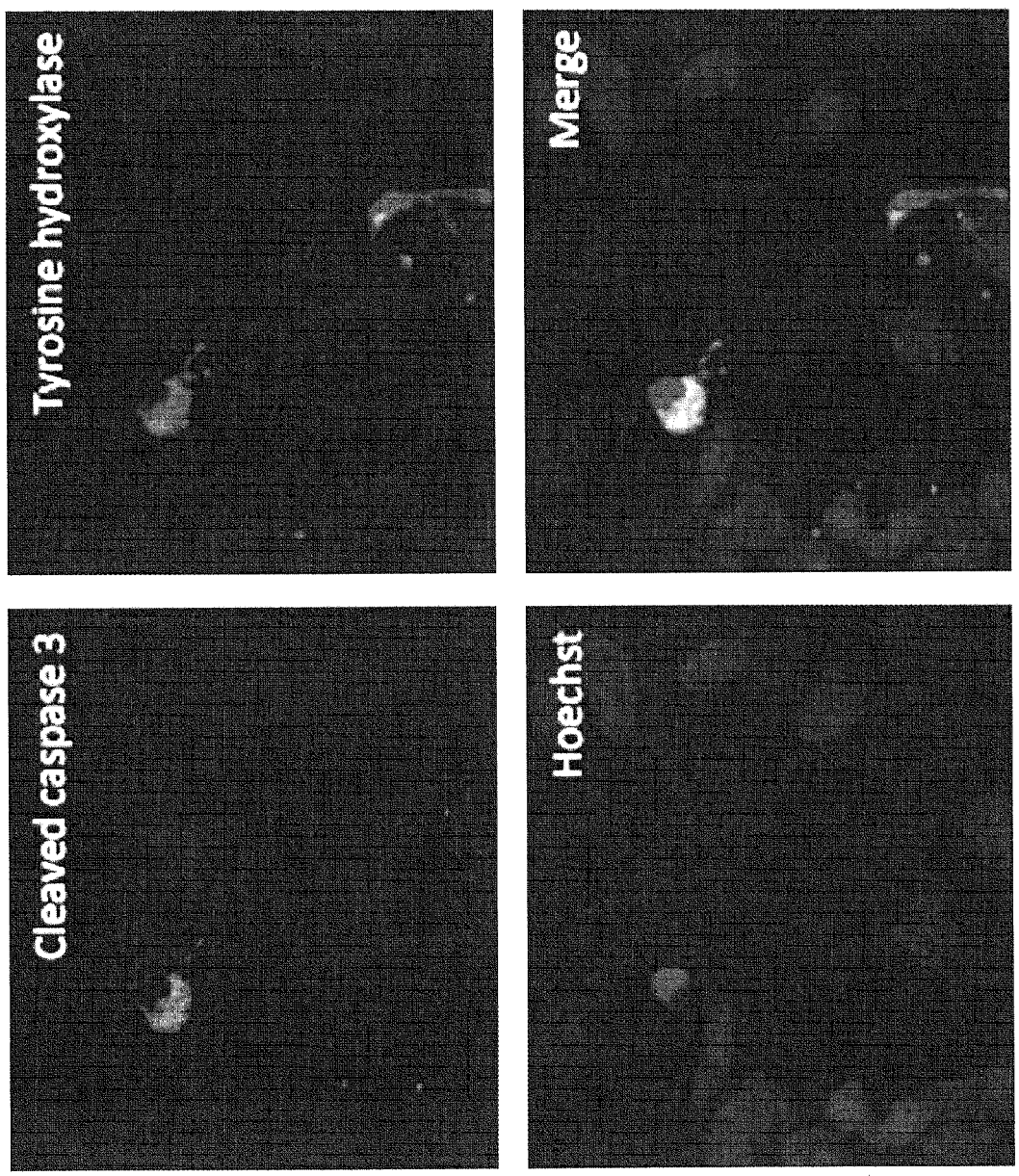

1.7 Treatment of E14 VM Monolayer Cultures with Soluble LIF or Targeted LIF Nanoparticles Reduces Levels of Dopaminergic Apoptosis A subset of tyrosine hydroxylase neurons co-localised with cleaved caspase-3 and a condensed nucleus, both markers of apoptotic cells. This indicates that a proportion of dopaminergic neurons in E14 VM cultures undergo apoptosis during culture (FIGS. 8A and 8B), contributing to the decrease in the number of these neurons as culture time progresses. Immunocytochemical analysis was performed to determine whether LIF treatment (soluble or targeted nanoparticles) decreased the number of apoptotic dopaminergic neurons in these cultures.

Figure 9A:
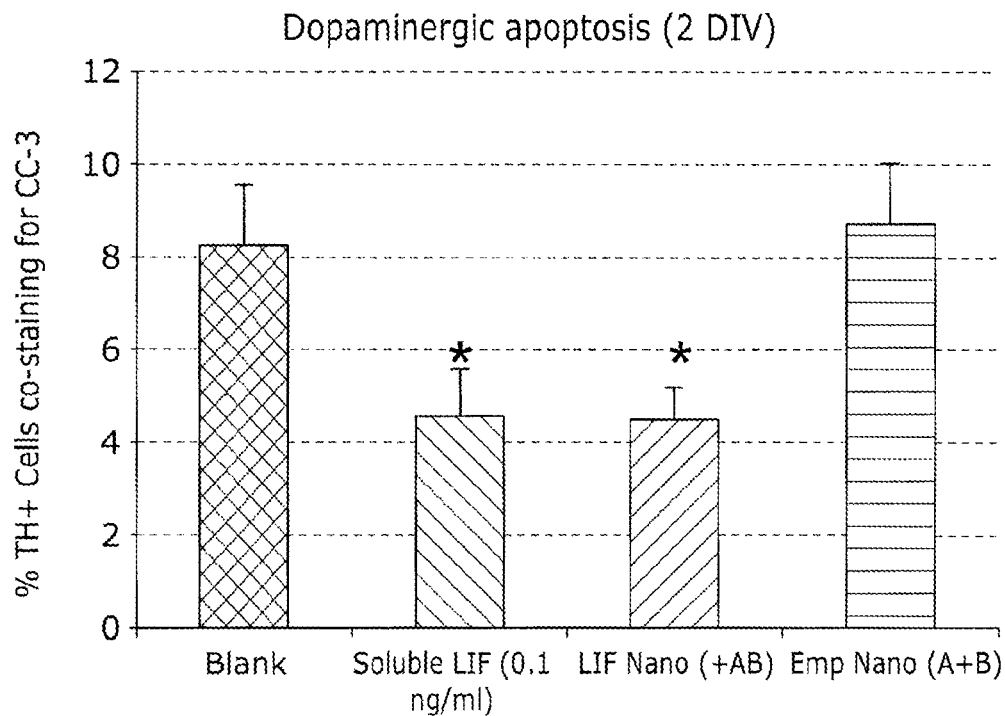
FIGS. 9A, 9B, and 9C show graphs of the results of treatment of E14 VM cultures with 0.1 ng/ml LIF or targeted LIF nanoparticles after 2, 3 and 5 days, demonstrating a significant reduction in the level of dopaminergic apoptosis at 2 days in vitro.
Figure 9B:
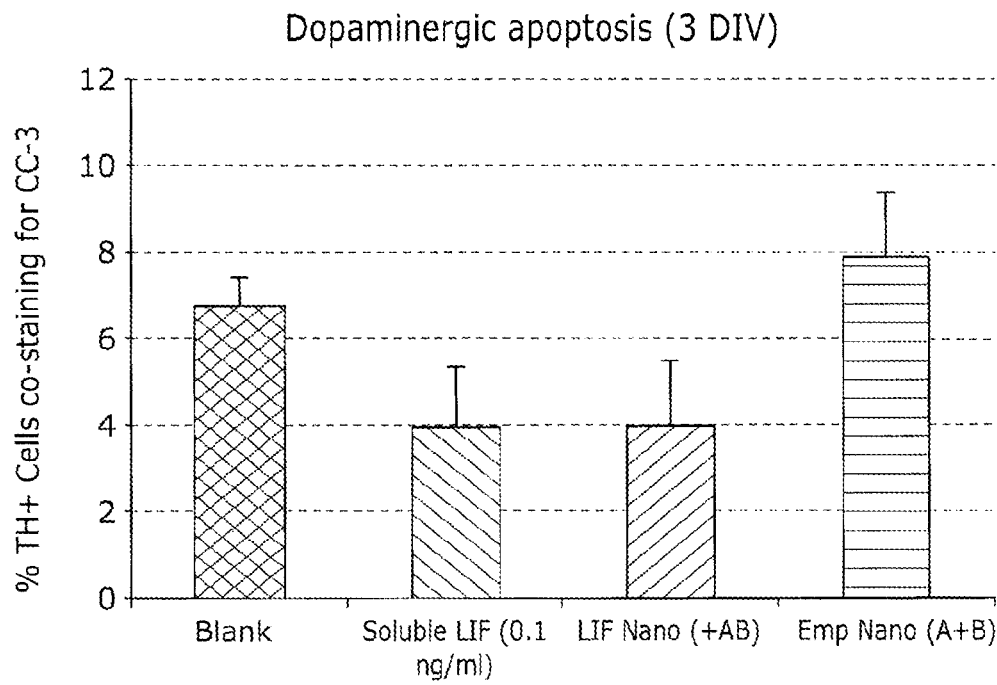
Figure 9:
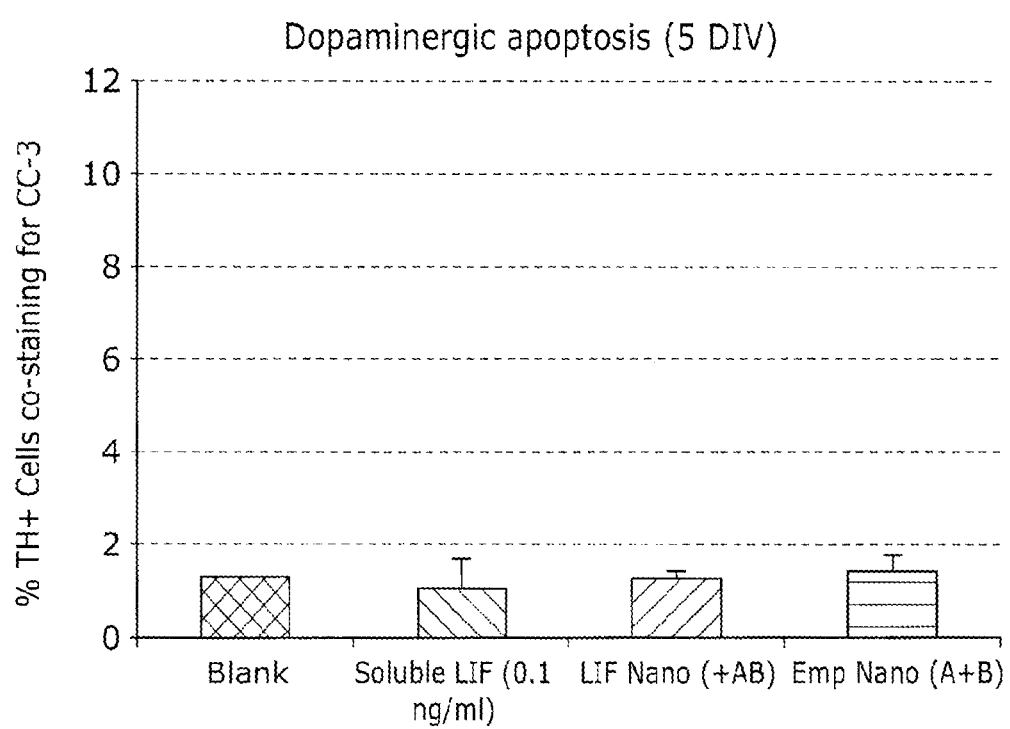

E14 VM monolayer cultures, treated with soluble LIF or LIF/empty nanoparticles were fixed after 2, 3 or 5 days. Immunocytochemical analysis for cells positive for tyrosine hydroxylase, cleaved caspase-3 (CC-3) and a condensed nucleus demonstrated a significant reduction in dopaminergic apoptosis. It was found that LIF treatment resulted in reduced numbers of apoptotic dopaminergic neurons after 2 days in vitro (FIGS. 9A-C). A trend towards reduced apoptosis in the presence of LIF remained after 3 days in vitro but did not reach statistical significance. Together with the finding that LIF does not bias E14 VM towards neural differentiation, this result suggests the increase in TH+ cells seen with chronic LIF treatment is an effect of increased dopaminergic cell survival.

1.8 Serotonin Neurons in E14 VM Cultures Express GDNFR-α1

Figure 10:
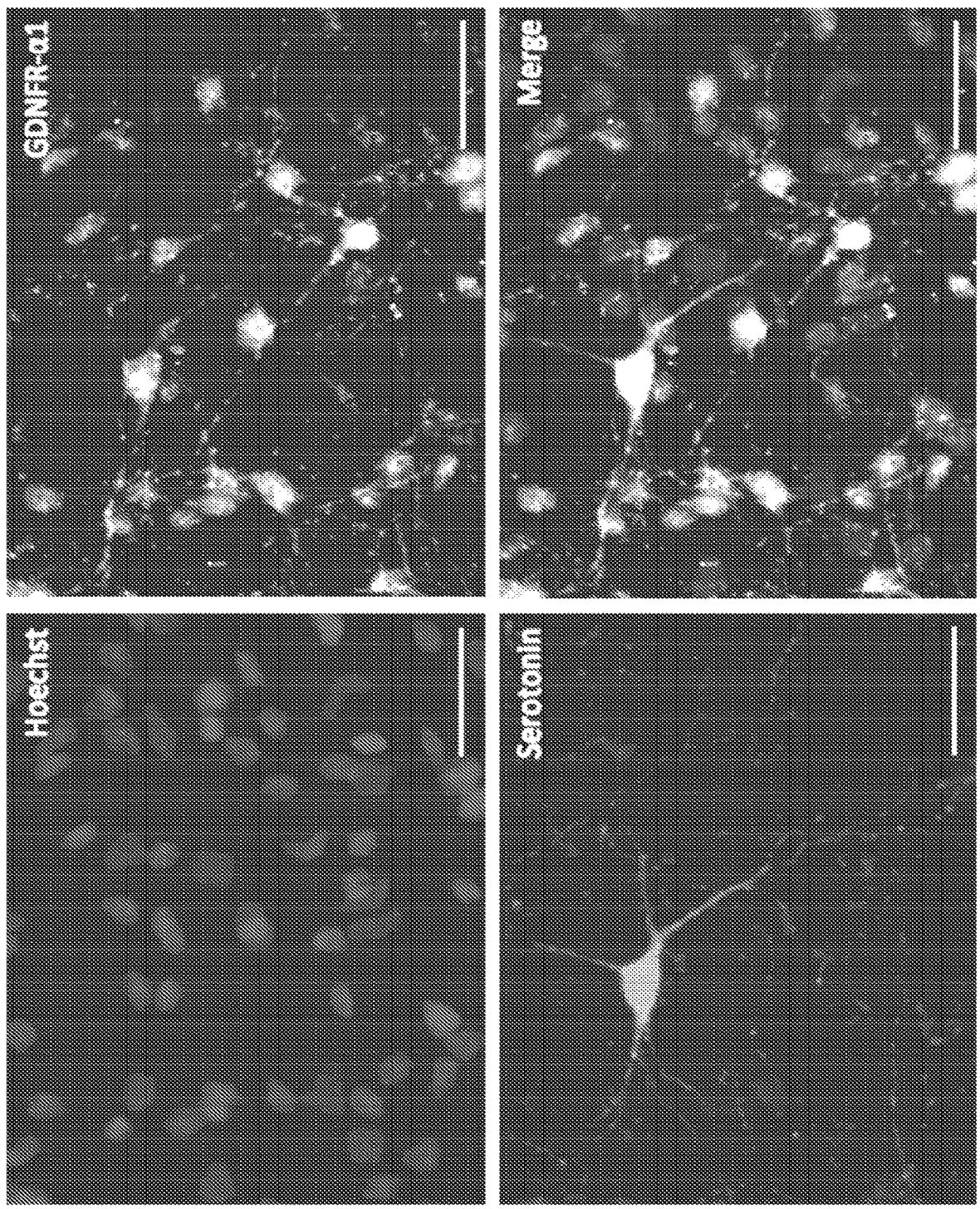
FIG. 10 shows micrographs indicating that serotonin neurons express GDNF receptor α1 (GDNFR-α1). Analysis of the stained culture demonstrated that serotonin neurons from E14 VM express GDNFR-α1 both on their soma and neurites. The scale bar represents 50 μm.

Contaminating serotonin neurons in foetal grafts have been linked to the development of graft-induced dyskinesias ('GIDs') in Parkinson's Disease patients. It was therefore of interest to determine whether LIF treatment had any effect on the number of serotonin neurons in E14 VM cultures. An E14 VM culture was fixed after 5 days in vitro and stained with antibodies against GDNFR-α1 and serotonin. As a first step, immunocytochemistry was performed to reveal whether serotonin neurons in these cultures express GDNFR-α1, the protein being used to target LIF nanoparticles. Dual staining for serotonin and GDNFR-α1 demonstrated that serotonin neurons express GDNFR-α1 (FIG. 10).

Figure 11B:
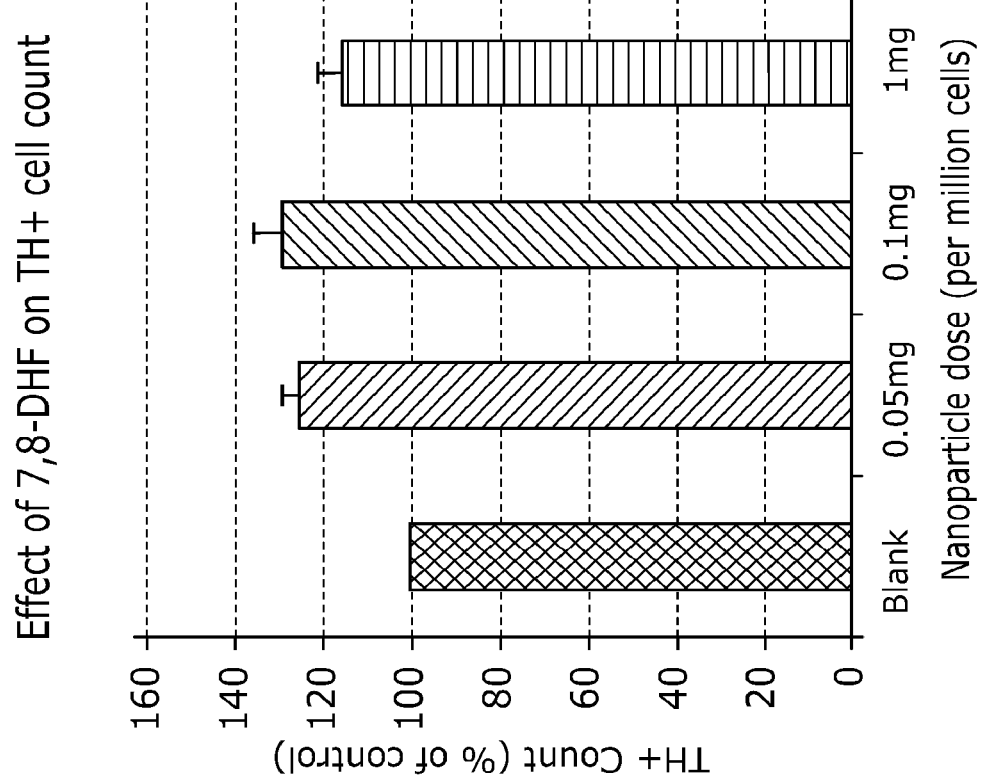
FIGS. 11A-11H show graphs of results indicating that rat E14 VM cultures respond to Thy-1 targeted nanoparticles. The nanoparticles were directed to Thy-1 using biotinylated anti-Thy-1 in the NP surface: they carried a cargo of 7,8 dihydroxyflavone (7,8 DHF), a BDNF agonist that binds TrkB, the BDNF receptor.
Figure 11A:
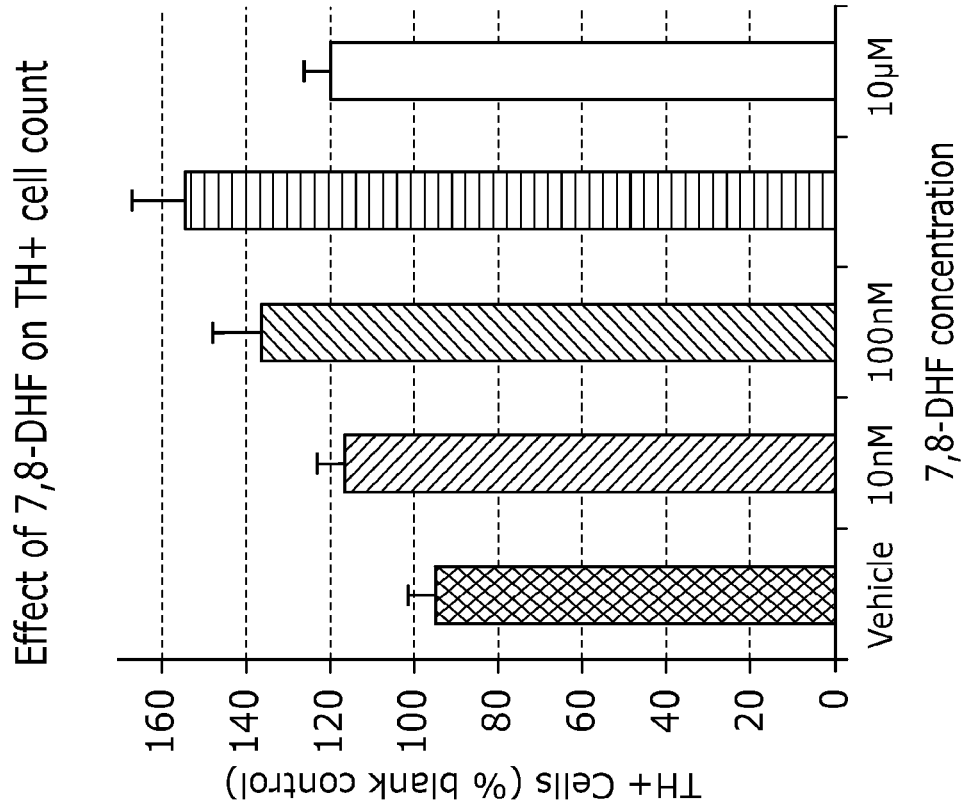

1.9 Anti-Thy-1 Directed Nanotherapy: Either Nanoparticle-delivered BDNF, or Nanoparticle-delivered 7,8 dihydroxyflavone (7,8-DHF) Improves Yield of TH+ Cells and this is Comparable to Treatment with Soluble BDNF, or Soluble 7,8-DHF To compare the effect of brain-derived neurotrophic factor (BDNF), or the BDNF agonist 7,8-dihydroxy flavone (7,8-DHF), when in a nano-particulate formulation targeted to Thy-1, versus free, primary rat E14 VM tissue was mixed with 100 μl of nanoparticle solution (0.05 mg; 0.1 mg; 1.0 mg nanoparticles/ml), or with free growth factor (10 nM; 100 nM; 1 μM; 10 μM) immediately prior to plating. After first confirming presence of Thy-1 antigen on the surface of TH+ neurons (data not shown), anti-Thy-1 decorated nanoparticles were prepared as either empty; or BDNF-nanoparticles; or 7,8 DHF-nanoparticles. Cultures were fixed after 7 days in vitro and analysed via immunocytochemistry for tyrosine hydroxylase positive cells. Plating cells with targeted BDNF-, or 7,8 DHF-nanoparticles significantly increased the TH positive cell count to levels comparable with the effect of free BDNF or 7,8-DHF. Analysis of cells demonstrated a response to BDNF, and to the BDNF-agonist 7,8-dihydroxy flavone (7,8-DHF), delivered in nano-formulation targeted to Thy-1. This is shown for 7,8 DHF-nanoparticles in FIG. 11A and FIG. 11B where the dose-response curve is similar to that reported by Jang et al (Jang et al, Proc. Natl. Acad. Sci. USA, 2010), with the exception of the high dose (10 μM) decline observed here.

Figures 11C, 11D:
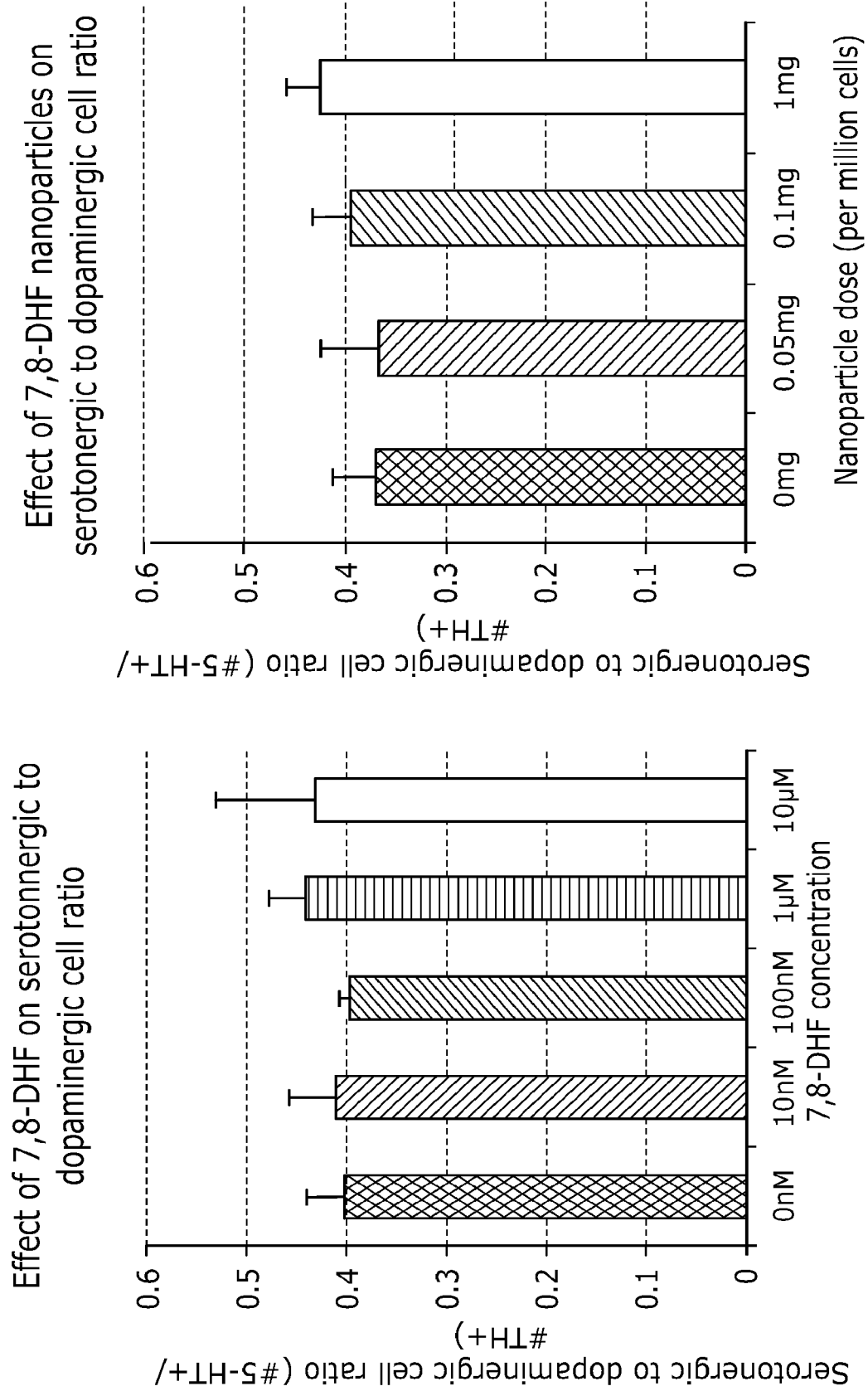
Figure 11F:
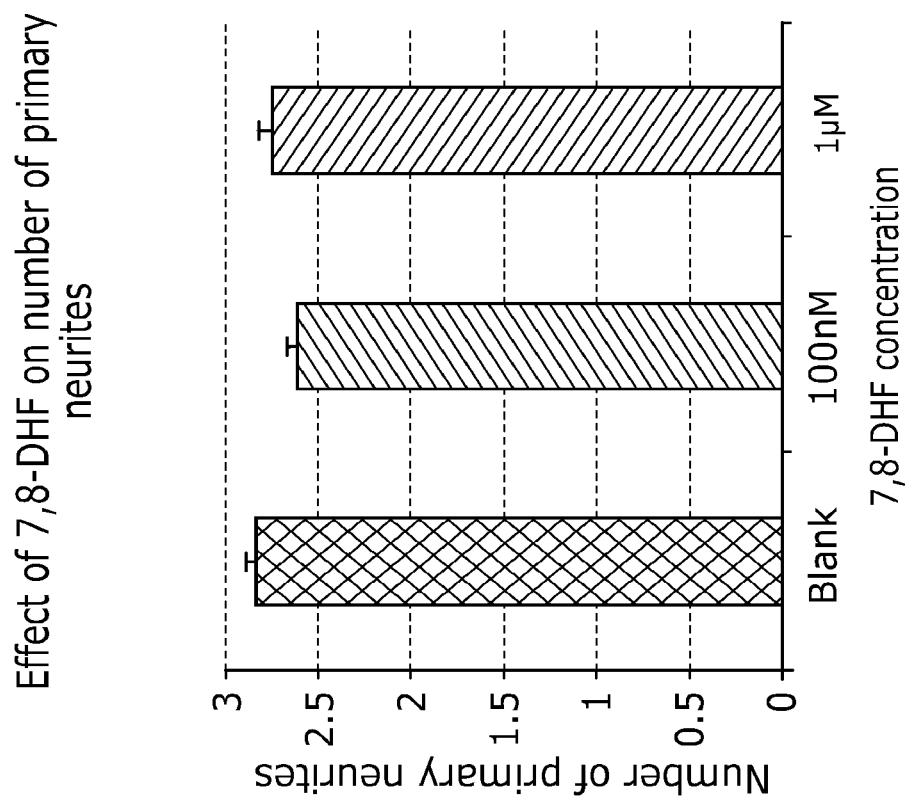
Figure 11E:
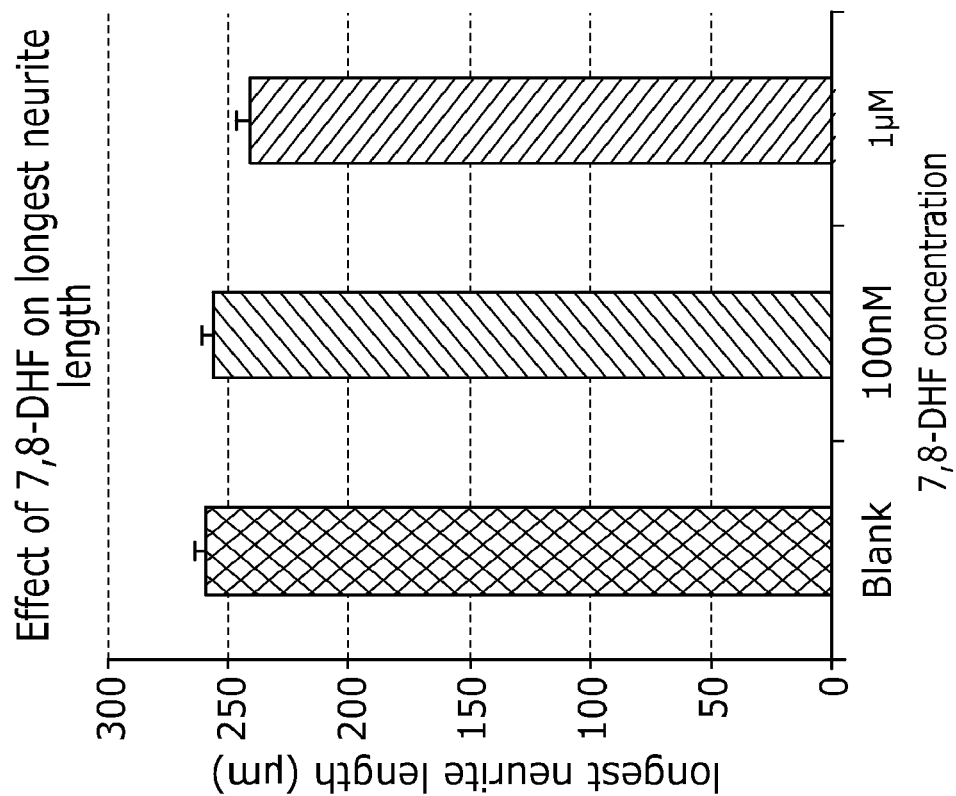
Figures 11G, 11H:
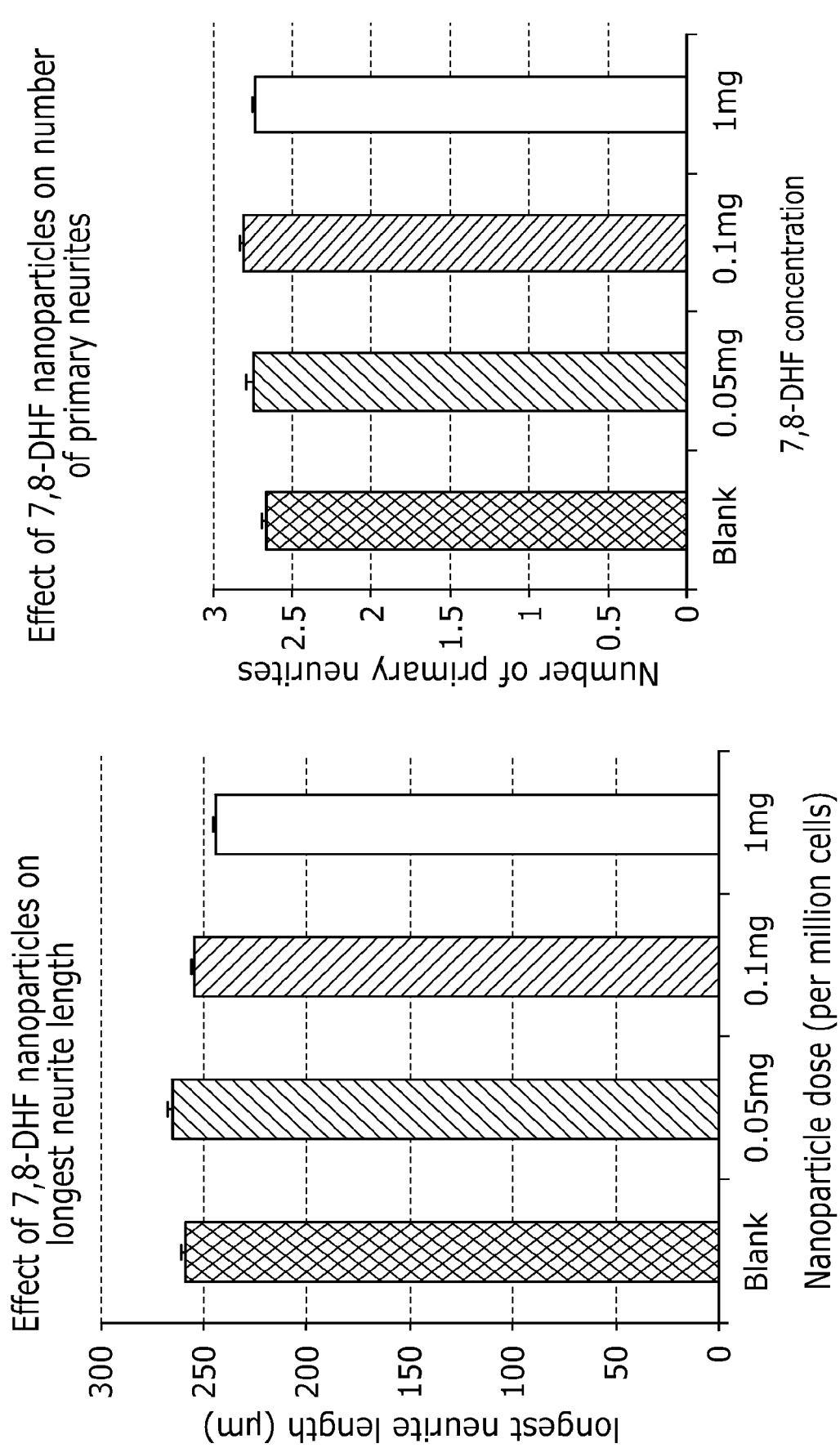

The experiment also tested for the effect of BDNF and 7,8-DHF on serotonergic cells versus dopaminergic cells where a constant ratio was found (FIG. 11C and FIG. 11D). Measurement of both longest neurite length and number of primary neurites revealed a significant increase for both parameters following treatment with BDNF or BDNF-nano (data not shown): unexpectedly, neither soluble 7,8-DHF nor 7,8-DHF-nano altered neurite length or number (FIG. 11E-FIG. 11H).

1.10 Rat Fetal VM Grafts Treated Ex Vivo with LIF or BDNF Nanoparticles Prior to Grafting into the Striatum of Lesioned Syngeneic Recipients show no Evidence of Adverse Effects though do not Significantly Alter the Response to Amphetamine.

Figure 13C:
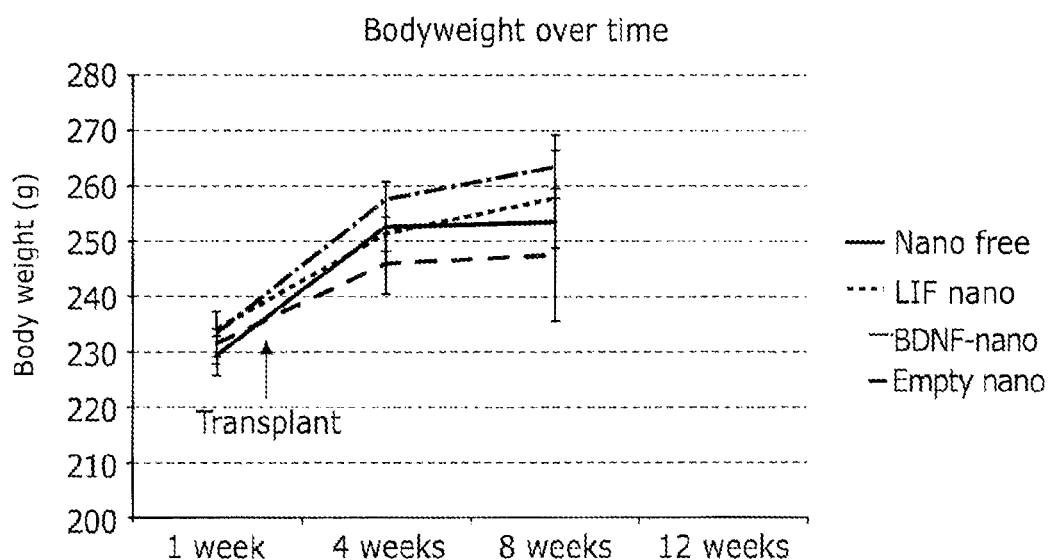

Following transplantation surgery rats in all groups continued to gain weight. Post-transplantation weight gain was not affected by nanoparticle supplementation of grafted tissue. Two way repeated measures ANOVA: significant effect of time $F_{1.74, 41.75}=99.30$, $p<0.001$, no effect of group $F_{3,24}=1.3$, $p=0.311$, no time x group interaction $F_{9,24}=0.74$, $p>0.05$. FIG. 13C.

Figure 13D:
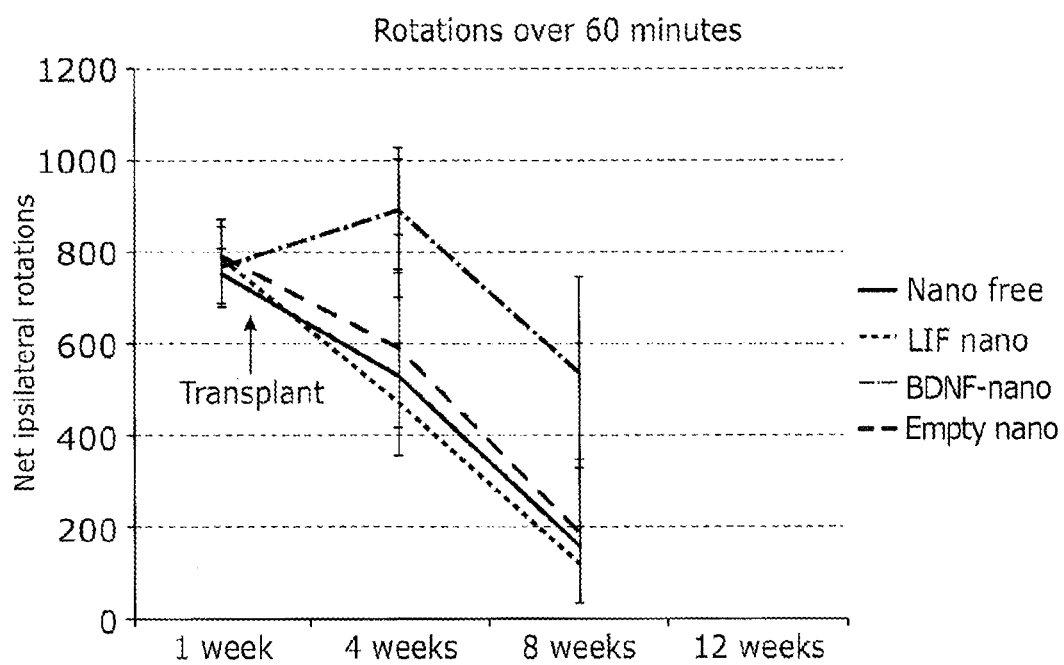

In the amphetamine-induced rotation assay, there was a significant reduction in net ipsilateral rotation across all groups. There was no significant effect of nanoparticle supplementation on recovery rate in the reduction of amphetamine induced rotation post-transplant. Two way repeated measures ANOVA: significant effect of time $F_{1.7, 41.1}=18.41$, $p<0.001$, no effect of group $F_{3,24}=1.89$, $p=0.158$, no time x group interaction $F_{9,24}=1.21$, $p>0.05$. FIG. 13D.

EXAMPLE 2

Figure 12:
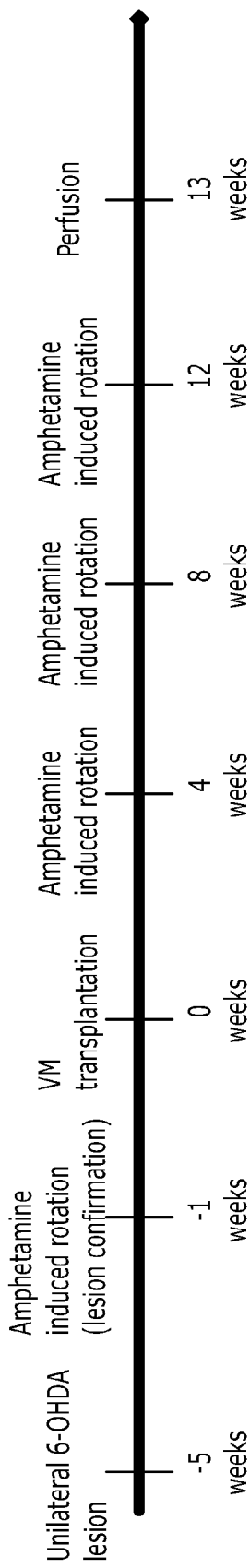
FIG. 12 shows the experimental protocol for transplanting primary isolates of rat VM cells into the striatum of isogenic Lewis rats.

2.1 Human: Monolayer and Neurosphere Cultures—Expansion of Cell Numbers to Provide Sufficient Cells for Testing Therapeutic LIF Nanoparticles 6-8 week old human foetal midbrain was dissected and cultured as neurospheres in proliferation medium before being sectioned and stained. Upon passage, parallel cultures as monolayer were grown in differentiation medium. Dopaminergic cells are positive for tyrosine hydroxylase (TH). Total cell numbers are stained with nuclear antigen (Hoechst). See FIG. 12, where: Primary=primary cultures; Passage 0=first subculture; Passage 1=second subculture.

Results show (i) maturation of TH+ neurons within the neurosphere microenvironment; (ii) differentiation of TH+ neurons grown in monolayer. Passage 2 also contains dopaminergic (DA) cells. These amplified cells were used to test LIF-nano effects on DA cell maturation and overall cell survival.

Figure 14:
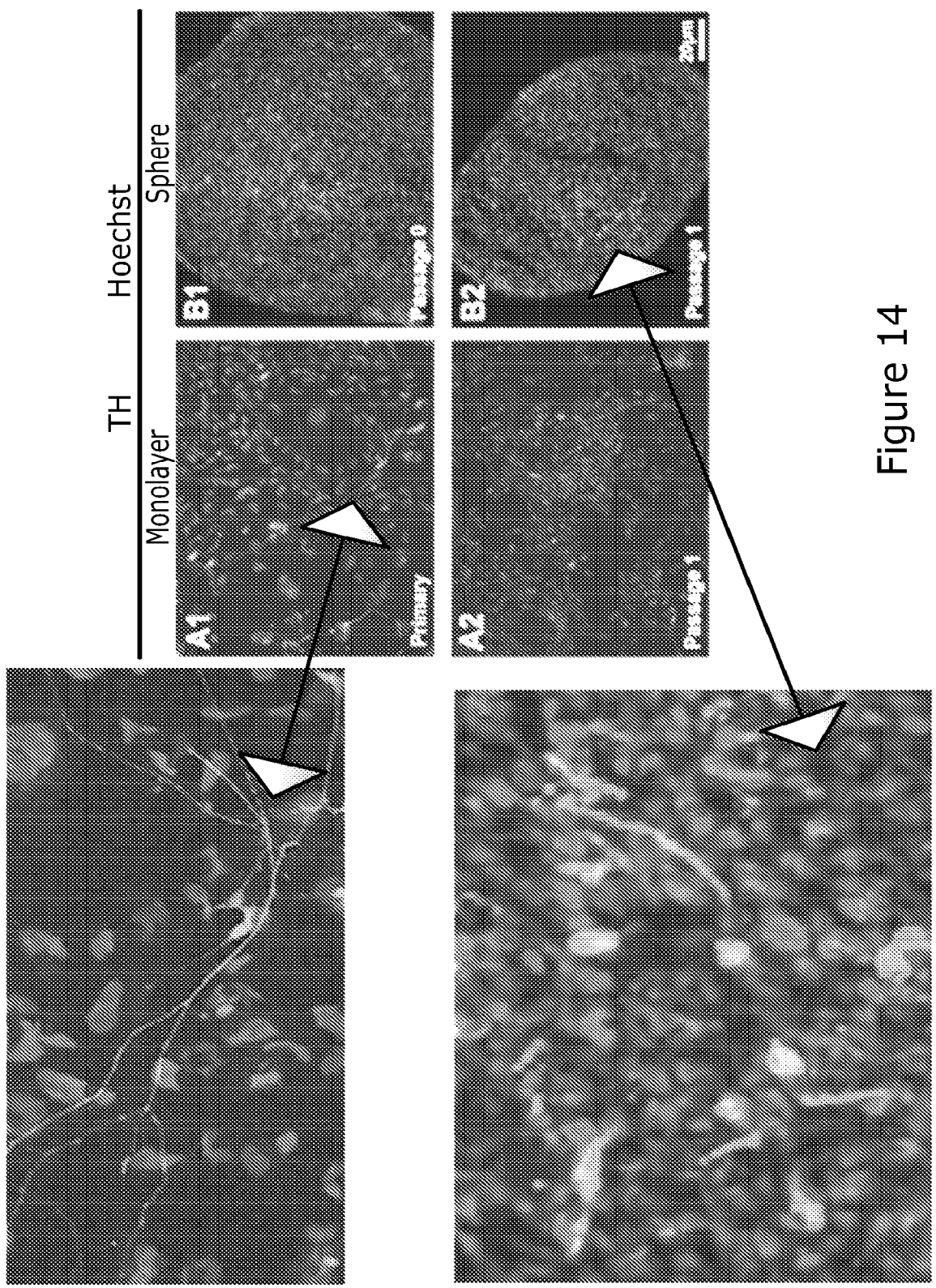
FIG. 14 shows micrographs demonstrating the expansion of primary human foetal ventral mesencephalon culture cell numbers to provide sufficient cells for testing LIF therapeutic nanoparticles. Primary=primary cultures; Passage 0=first subculture; Passage 1=second subculture.
Figure 15:
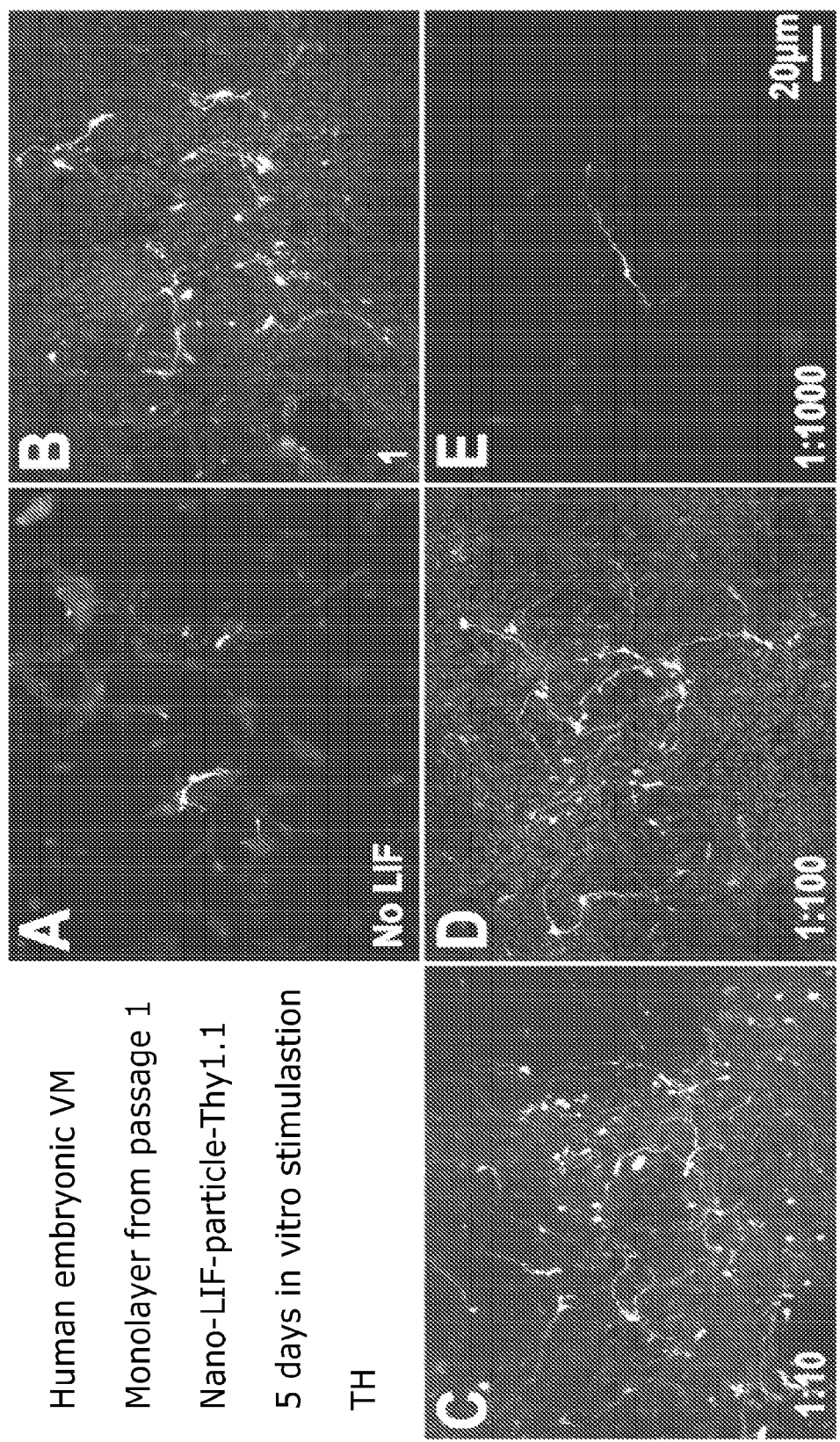
FIG. 15 shows micrographs with the amplified cells of FIG. 14 used to test the effect of LIF nanoparticles at increasing concentrations (dose) on dopaminergic cell maturation and overall cell survival.
Figure 16:
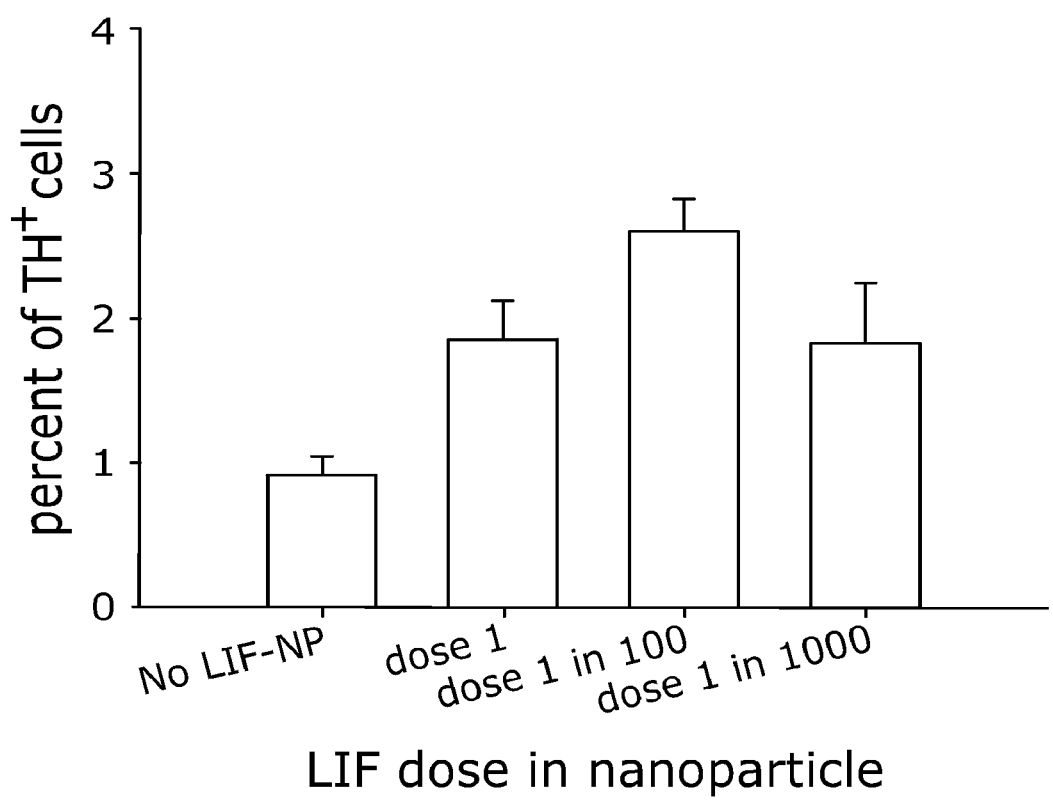
FIG. 16 shows a graph providing quantification of the results of FIG. 15.

2.2 Human Foetal Ventral Mesencephalon LIF-nanoparticle Therapy Enhances Human Dopaminergic Neuron Derivation After establishing culture conditions for expansion of primary human foetal VM cells, these cells were used to test therapeutic efficacy of the LIF-nano device (see FIG. 14). Cultures were stained for tyrosine hydroxylase (TH) after 5 days in culture in the presence or absence of LIF nanoparticles targeted to Thy-1. Three sets of experiments were completed. A dose of 1/100 LIF-nanoparticles targeted to Thy-1 resulted in both (i) 3-fold increase in overall cell numbers and (ii) a percentage fold increase of 2.5% TH+ cells within this overall cell population. Thus, there was a greater than 5-fold increase of dopaminergic cells as a result of LIF-nano therapy (see FIGS. 15 and 16).

EXAMPLE 3

3.1 Treatment of Human Foetal Ventral Mesencephalon (hfVM) with LIF-nanoparticle Therapy, or XAV939-Nanoparticle Therapy, Enhances Human Dopaminergic Neuron Derivation and Increases hfVM Cell Survival Both in Vitro and in Vivo.

Figure 17:
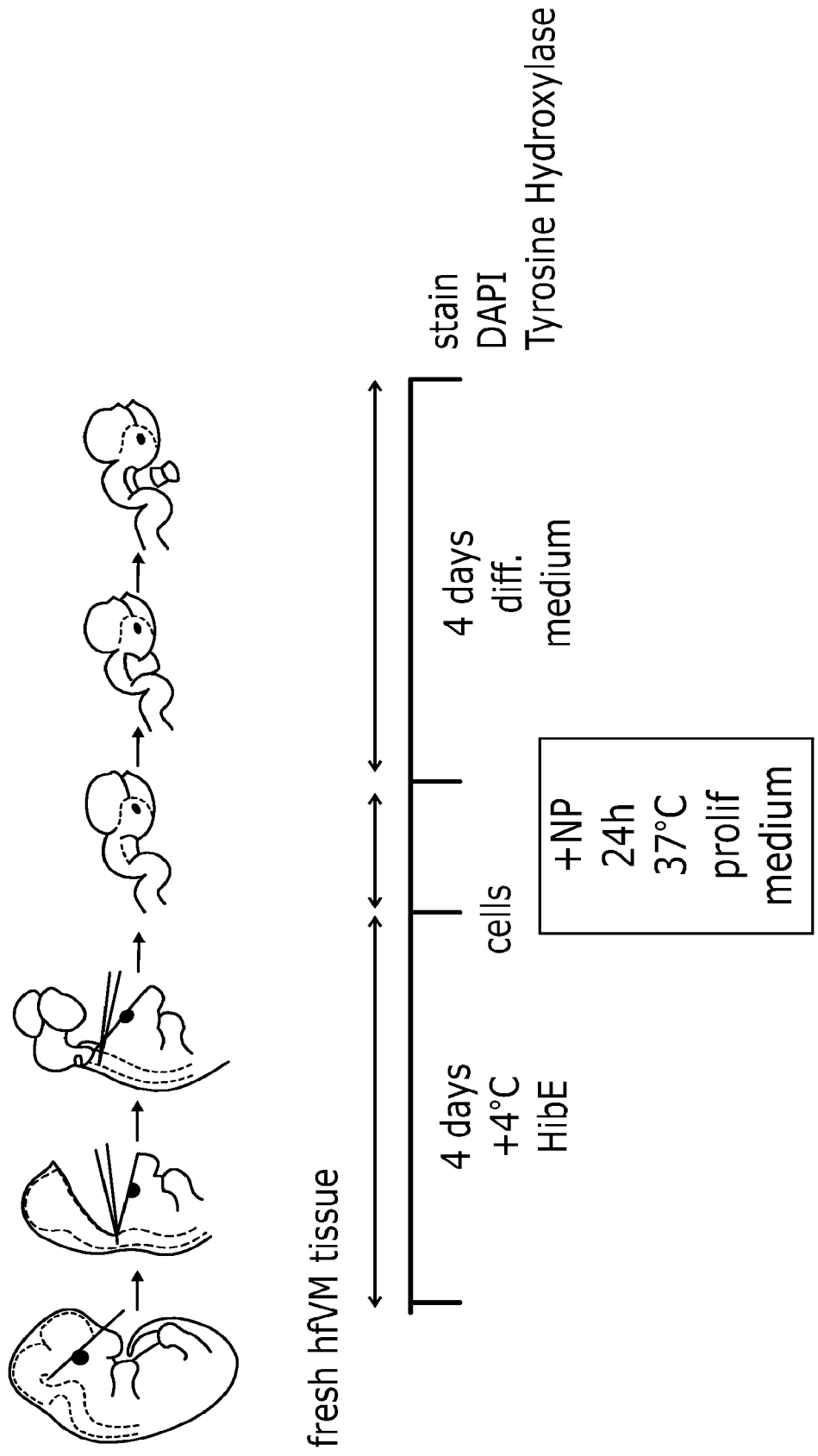
FIG. 17 shows the protocol for testing the effect of LIF-nanoparticle treatment targeted to Thy-1 on human foetal VM cell grafts in vitro.
Figure 18:
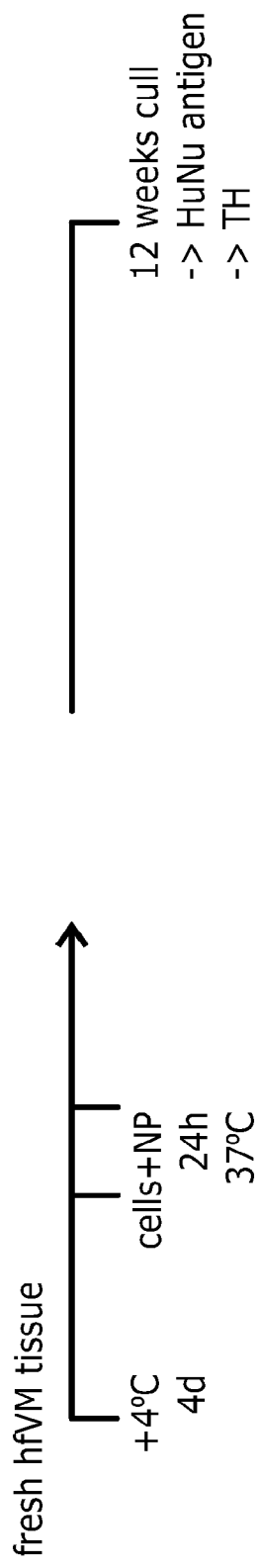
FIG. 18 shows a schematic of a protocol to measure the effect of nanotherapy in vitro by incubating hfVM cells for 24 h at 37° C. together with Thy-1 targeted particles loaded with various cargos prior to transplantation into the striatum of a nude rat. β
Figure 19:
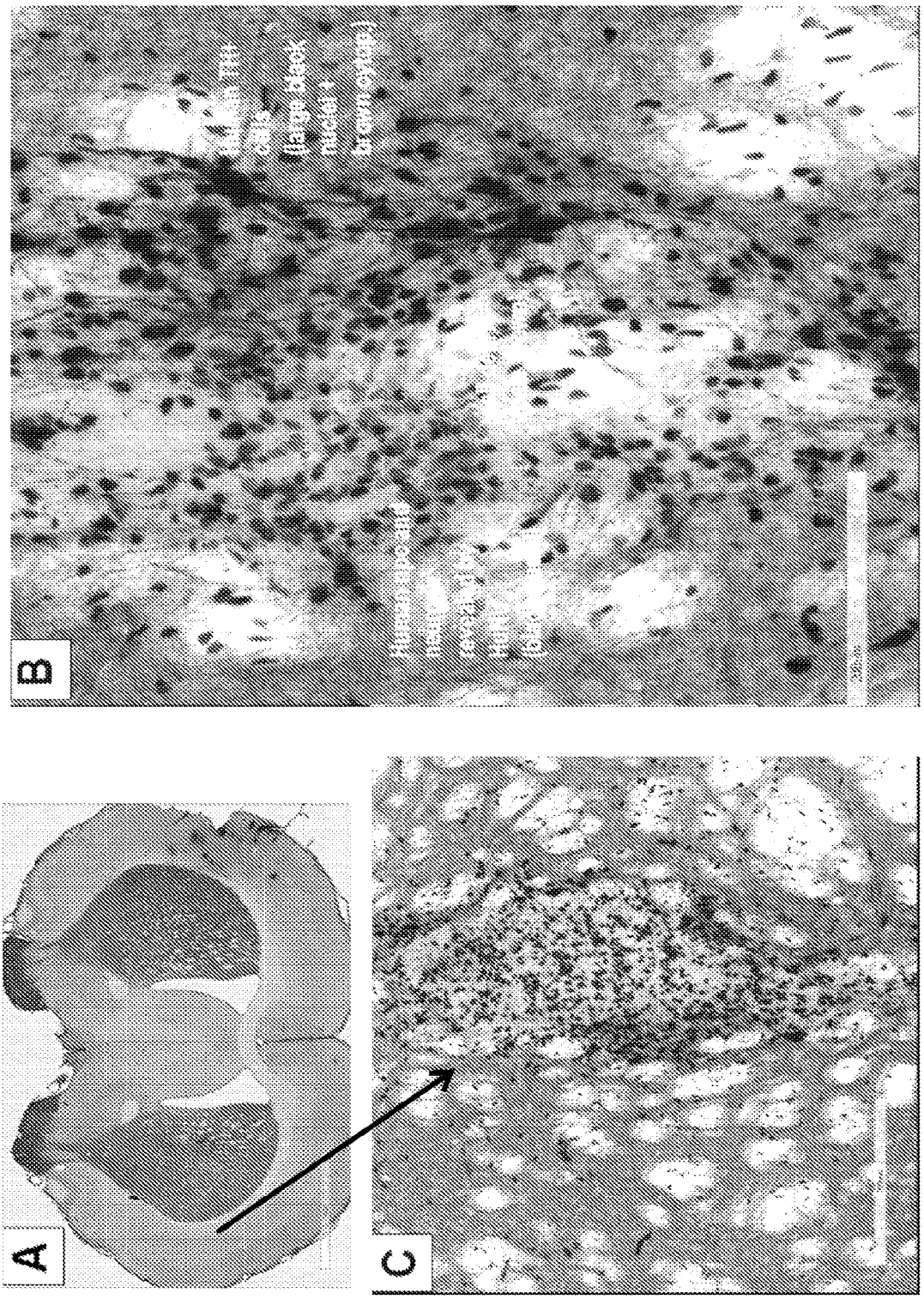
FIG. 19 shows photographs and micrographs of sections of striatum of a nude rat brain that comprises LIF-nano treated hfVM cells. A: low power section showing graft stained for HuNu and TH positive cells, enlarged in B. Further enlargement in C shows large numbers of HuNu staining cells plus some TH+ cells both within the graft site and spreading out from this site.
Figure 20:
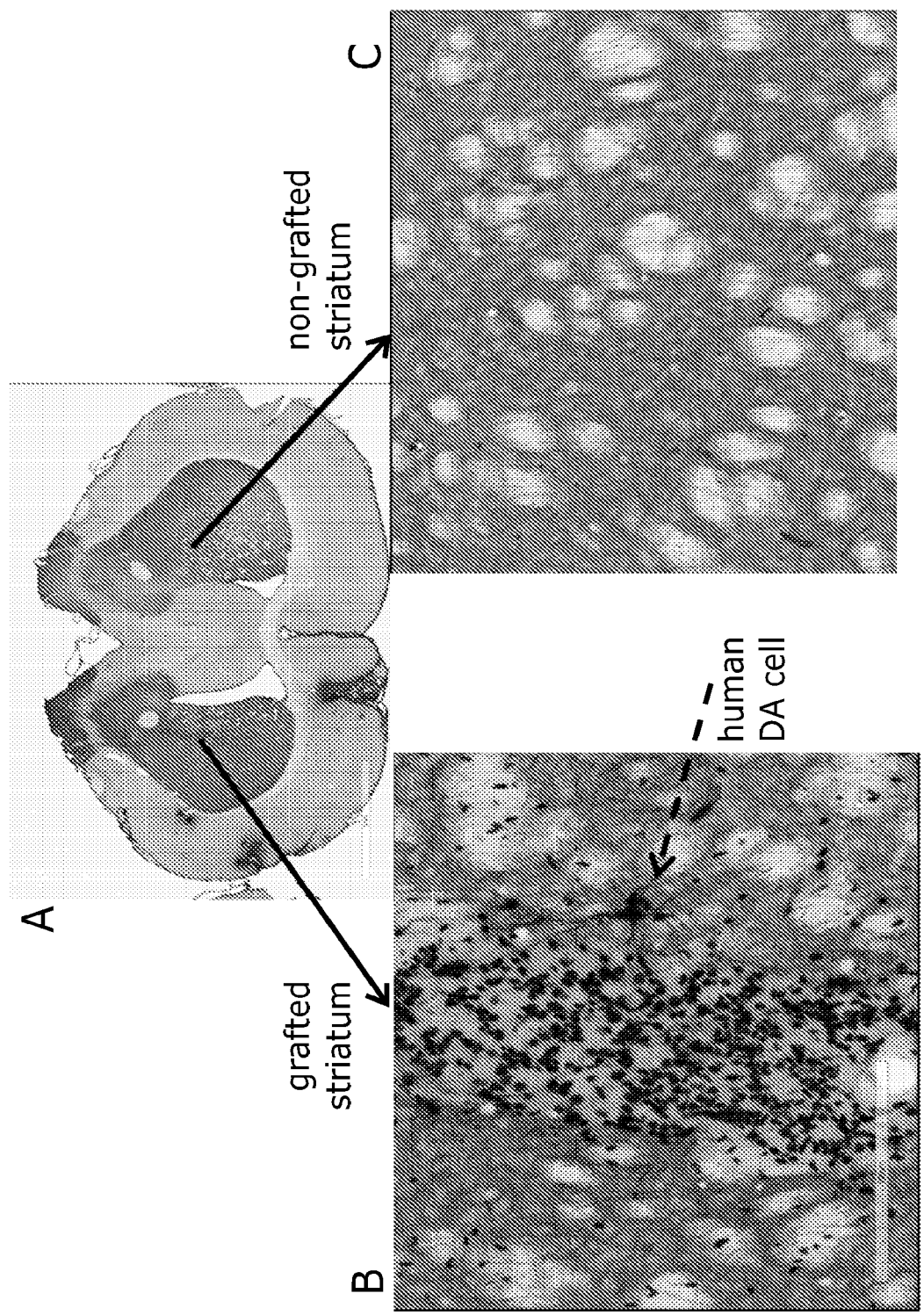
FIG. 20 shows photographs and micrographs of sections of striatum of a nude rat brain following transplantation of XAV939-Nano treated hfVM cells. A: low power section showing striatum (brown) with grafted hfVM cells (black nuclei) on left "grafted striatum"—shown in higher power in B. B also shows human dopaminergic cell within the graft site (DA cell). Ungrafted striatal tissue (C) acts as endogenous control for specificity of HuNu staining of hfVM: no stained nuclei are present.
Figure 21:
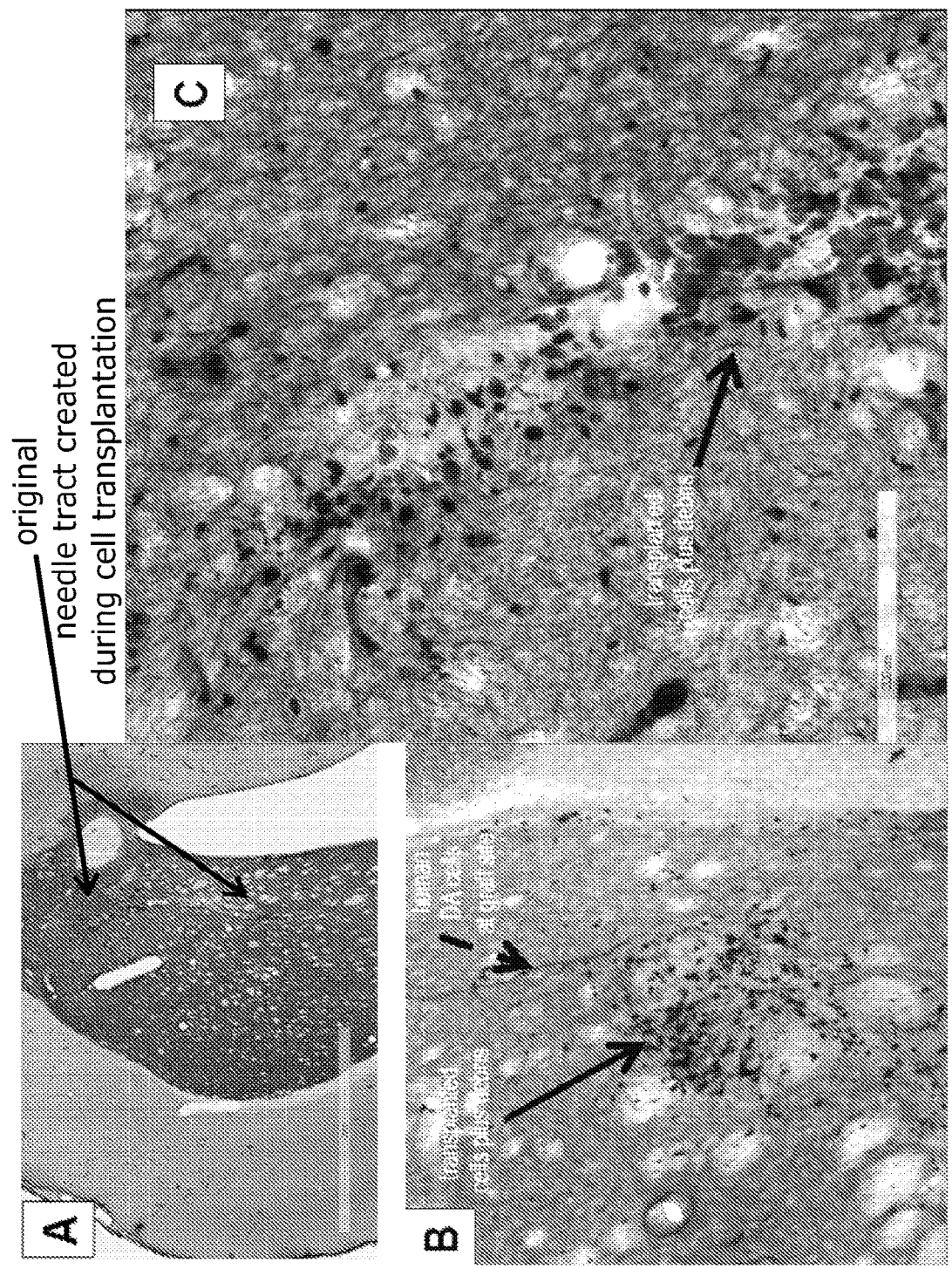
FIG. 21 shows photographs and micrographs of sections of striatum of a nude rat brain following transplantation of Retinoic Acid (RA)-Nano treated hfVM cells. A: low power section showing striatum with grafted hfVM cells (black nuclei) where the injection needle tract (solid arrow) is marked by the presence of the HuNu stained nuclei. B shows a different section of the same recipient as in A, at higher power, showing surviving cells plus some cell debris (solid arrow): the dashed arrow indicates human dopaminergic TH+ cells. C shows a further higher power of the grafted cells in situ plus cell debris.
Figure 22:
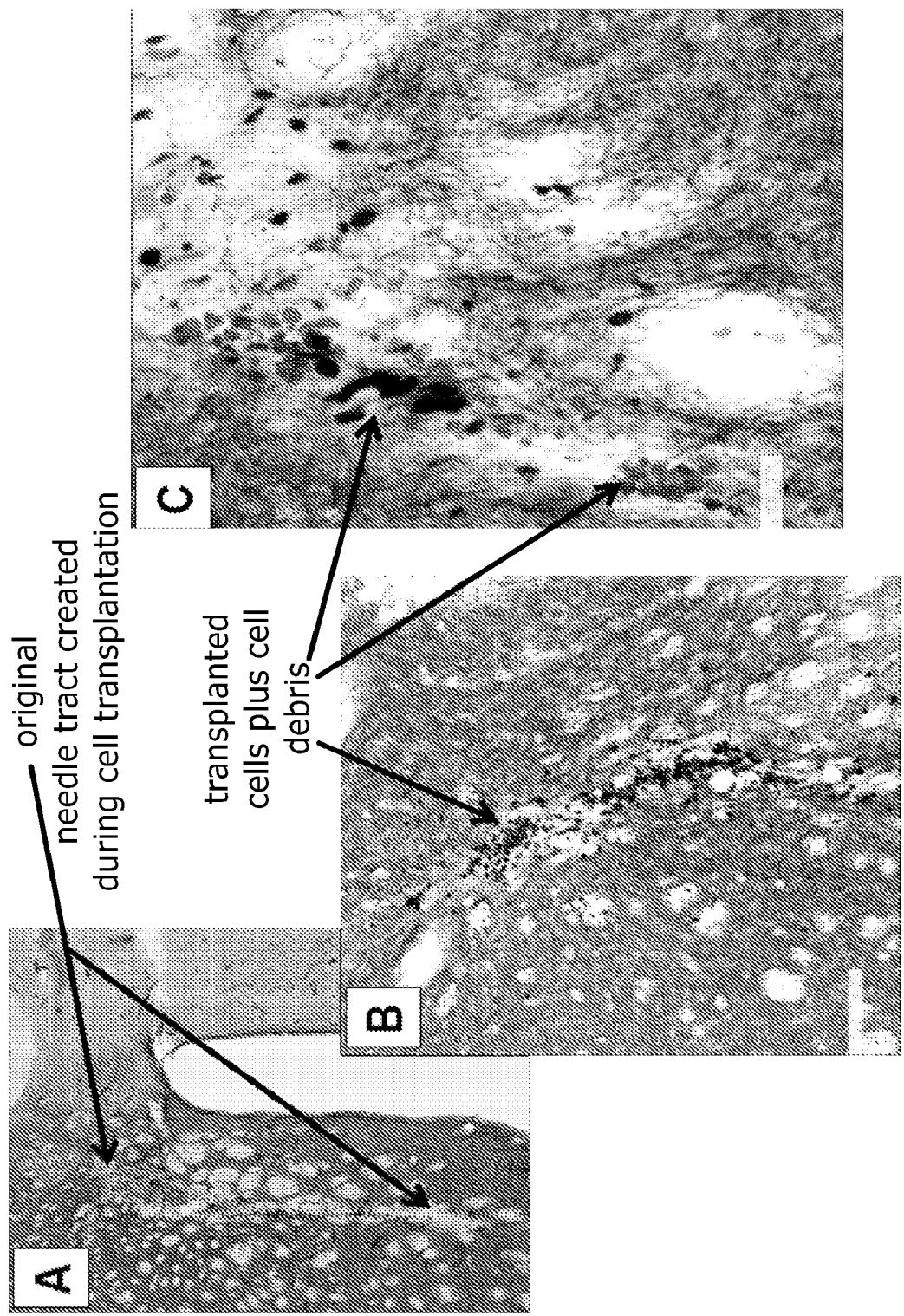
FIG. 22 shows photographs and micrographs of sections of striatum of a nude rat brain following transplantation of control Empty-Nano (i.e. nanoparticles targeted to Thy-1 but without any cargo) treated hfVM cells. A: low power section showing striatum (brown) with grafted hfVM cells (black nuclei) where the injection needle tract (solid arrow) is marked by the presence of the HuNu stained nuclei. B and C show higher magnifications of the grafted cells, where cell debris (pale clumps) is also visible.

To measure the effect of nanotherapy in vivo: hfVM cells were prepared as for the in vitro experiments as outlined in FIG. 17, primary human fetal mesencephalon tissue was stored at 4° C. for upto 4 days in Hibernate E storage medium. The cells were then seeded on coverslips and cultured 4d in differentiation medium after which cells were stained by DAPI to enumerate nuclei and for tyrosine hydroxylase to identify and enumerate differentiated dopaminergic cells. Pooled tissue was then prepared for cell transplantation following the clinical TransEuro Protocol. The protocol summarised in FIG. 18 follows that of the TransEuro clinical trial assessing hfVM cell grafts as cell therapy in patients with Parkinson's disease: http://www.transeuro.org.uk. The harvested cells were divided into four aliquots in proliferation medium and treated with nanoparticles targeted to Thy-1 and carrying a cargo of (i) no cargo; (ii) LIF; (iii) XAV939; or (iv) retinoic acid for upto 24 h. The cells were then transplanted in to the striatum of nude rats aged between 12-16 weeks following the protocol in FIG. 22 using standard techniques. At 3 months the rats were perfused with BrdU according to standard protocols and then culled when the brain was harvested and sectioned for immune-cytochemical analysis.

Human nuclear antigen specific antibody (HuNu) stained transplanted human cells: tyrosine hydroxylase staining revealed human dopaminergic (DA) cells within the grafts (FIGS. 19, 20, 21 and 22). Beta III tubulin stained neurons, and BrdU identified any dividing cells post infusion and pre-cull. Numbers and localisation of cells were identified following image capture (Imagescope Aperio). The results show highly significant increased survival and distribution of transplant-derived neurons and DA cells in the striatum of rats receiving grafts pretreated with LIF-nano, or with XAV939-nano, when compared to the empty-nano controls. In particular the results quite clearly show the surprising and beneficial effects of nanoparticle devices of the invention (see FIGS. 19(C) and 20(B)) on cell survival and differentiation in the brain compared to control (see FIG. 22(C)).

Figure 23:
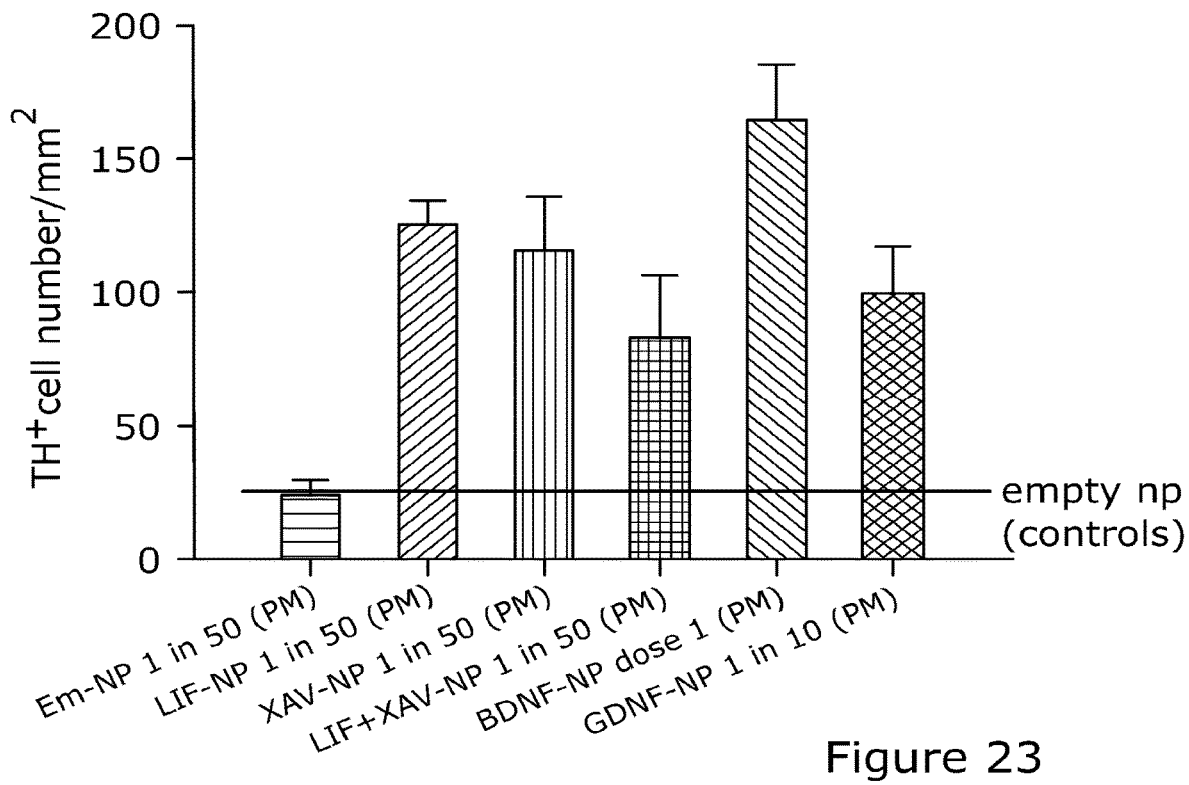
FIG. 23 is graph showing survival benefit of nanotherapeutics for TH positive dopaminergic cells according to the protocol of FIG. 17. EM-NP represents empty nanoparticle control.
Figure 24:
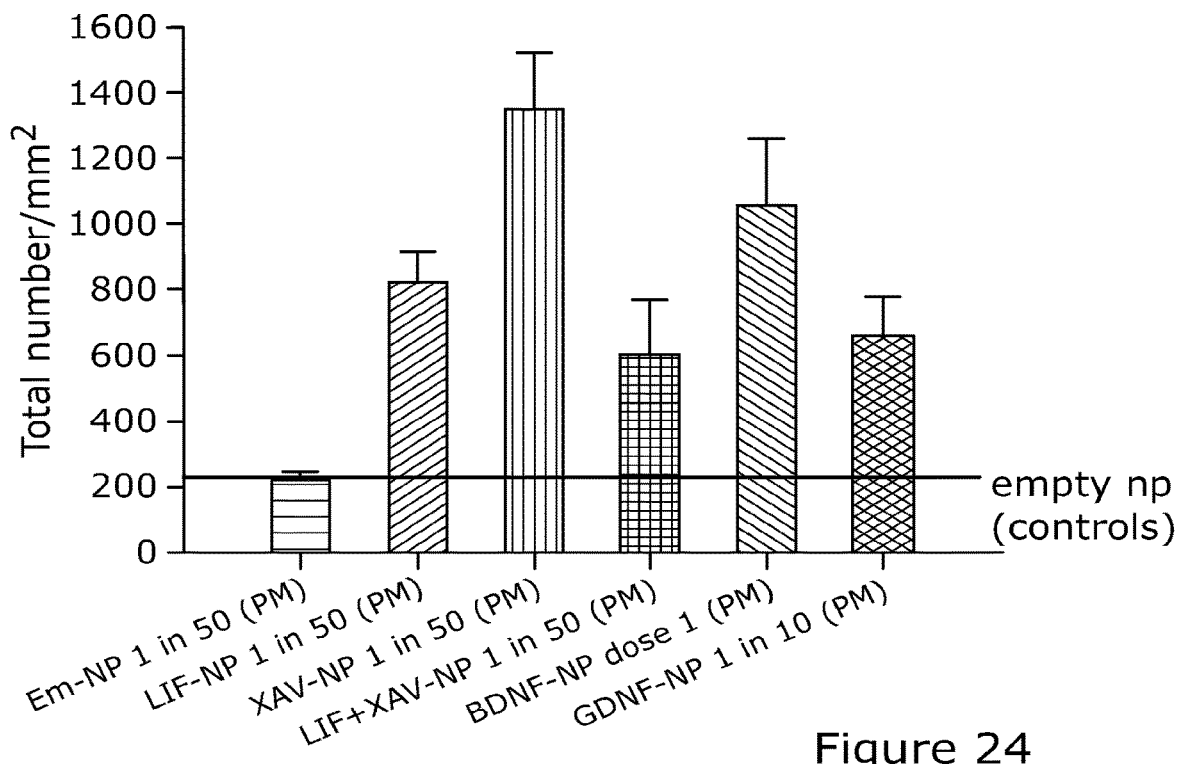
FIG. 24 is graph showing total cell numbers survival benefit of nanotherapeutics counting all DAPI positive cells according to the protocol of FIG. 17.
Figure 25:
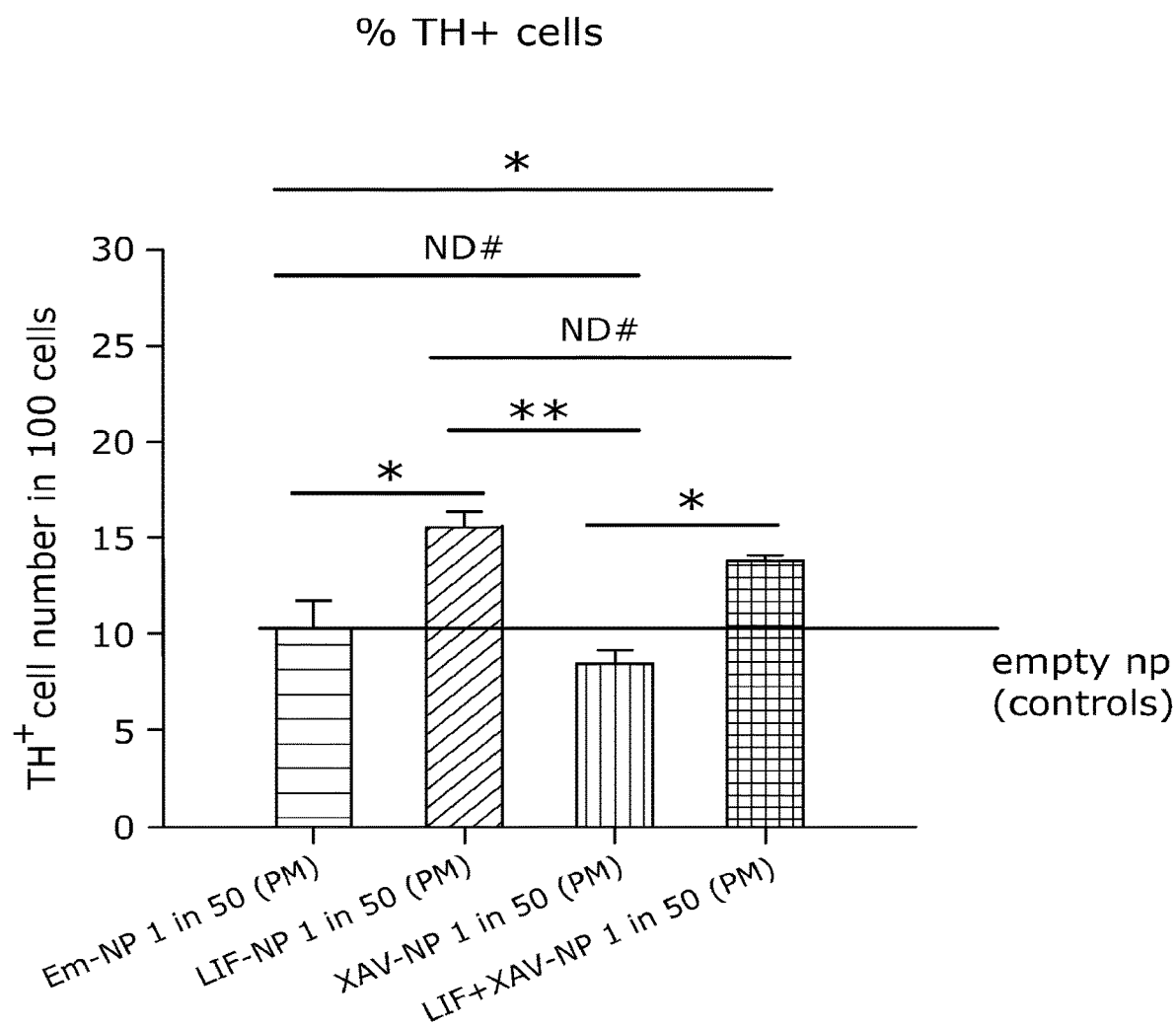
FIG. 25 is graph showing preferential survival benefit on dopaminergic cells expressed as percentage for each treatment according to the protocol of FIG. 17.

In vitro experiments paralleled the above in vivo study, but instead of transplantation, the cells were seeded onto coverslips in differentiation medium and grown for 4 days, fixed, and stained for DA cells and total neurons. Here six groups of nanoparticles were tested namely empty-nano; LIF-nano; XAV939-nano; LIF+XAV939-nano; BDNF-nano; and GDNF-nano; and the results are shown in FIGS. 23, 24 and 25. All cargos promoted cell survival with increased numbers of TH+ cells compared to the empty nanoparticle control group (Em-NP).

EXAMPLE 5

5.1 Preparation of Surface Targeted Nanoparticles Containing hLIF, mLIF or XAV939

Human LIF (Santa Cruz cat. SC-4377), mouse LIF (Santa Cruz cat. SC-4378), or XAV939 (Sigma Aldrich cat. X3004) was encapsulated in avidin-coated PLGA nanoparticles using a modified water/oil/water double emulsion technique.

Briefly, 50 µg of cytokine was dissolved in 200 µL PBS or 1 mg of XAV939 dissolved in DMSO at a concentration of 10 mg/ml (100 ul) was added dropwise with vortexing to 100 mg PGLA (50/50 monomer ratio, Durect Corp. cat. B0610-2) in 2 ml dichloromethane. The resulting emulsion was added to 4 ml of aqueous surfactant solution containing 2.5 mg/ml polyvinyl alcohol (PVA) (Sigma-Aldrich cat. 363138) and 2.5 mg/ml avidin-palmitate bioconjugate (see 5.2 below), and sonicated to create an emulsion containing nano-sized droplets of polymer/solvent, encapsulated cytokine and surfactant. Solvent was removed by magnetic stirring at room temperature; hardened nanoparticles were then washed 3× in DI water and lyophilized for long-term storage.

Targeted nanoparticles were formed by reacting the avidin-coated NPs in PBS with 4 µl biotin-antibody (0.5 mg/ml) per mg NP for 15 minutes and used immediately. Nanoparticle size and morphology are analyzed via scanning electron microscopy and dynamic light scattering in 1× PBS (Brookhaven Instruments, ZetaPALS). Drug or cytokine release was measured by incubating particles in PBS at 37° C. and measuring cytokine or drug concentrations in supernatant fractions by ELISA or UV Spectroscopy. Total encapsulation was approximated as the amount of LIF or XAV939 released over a seven day period and percent encapsulation efficiency calculated as total encapsulation divided by maximum theoretical encapsulation. Capture of biotinylated ligands was quantified using biotin-R-phycoerythrin as a model protein. NPs were suspended at 1.0 mg/ml in 1× PBS, and 200 ul added to eppendorfs containing varying concentrations of biotin-R-PE. NPs were reacted for 15-30 minutes at room temperature, centrifuged for 10 minutes at 12 k RPM, and the remaining biotin-R-PE in the supernatant quantified by fluorescence at excitation/emission 533/575 nm.

5.2 Preparation of the Avidin-palmitate Bioconjugate for Use in Surface Modification of Biodegradable Nanoparticles Stable avidin-lipid conjugates were formed using a zero-length crosslinking agent to create a covalent bond between the lipid carboxyl end groups and free amines on the avidin protein. Fatty acid (Palmitic acid, Sigma) was first reacted in 0.1× PBS with 1-ethyl-3-[3-dimethylaminopropyl] carbodiimide (EDC) and N-hydroxylsulfosuccinimide (sulfo-NHS) (Invitrogen) to convert the terminal carboxyl group to an amine-reactive sulfo-NHS ester. Avidin (Sigma) at 5 mg/ml was then reacted with 10-fold molar excess of the NHS-functionalized fatty acid in 0.1× PBS and the solution was gently mixed at 37° C. for 2 hours. Reactants were then dialyzed against 1.0× PBS at 37° C. for 24 hours to remove excess reactants and/or hydrolyzed esters.

The above protocol may be adapted for encapsulation of the other compounds described herein.

Although particular embodiments of the invention have been disclosed herein in detail, this has been done by way of example and for the purposes of illustration only. The aforementioned embodiments are not intended to be limiting with respect to the scope of the appended claims, which follow. It is contemplated by the inventors that various substitutions, alterations, and modifications may be made to the invention without departing from the spirit and scope of the invention as defined by the claims.

REFERENCES

Akiyama et al (1997) In vivo effect of recombinant human LIF in primates. Jpn J Cancer Res 88: 578-583

Barker R A. (2012) Stem Cells and Neurodegenerative disease—Where is it all going? Regen.Med (submitted).

Bauer S and Patterson P H (2006) Leukemia inhibitory factor promotes neural stem cell self-renewal in the adult brain. J Neurosci 26:12089-99.

Butzkueven H, Zhang J G, Soilu-Hanninen et al (2002) LIF receptor signaling limits immune-mediated demyelination by enhancing oligodendrocyte survival. Nat Med 8(6):613-9.

Deverman B E and Patterson P H (2012) Exogenous leukemia inhibitory factor stimulates oligodendrocyte progenitor cell proliferation and enhances hippocampal remyelination. J Neurosci 32:2100-2109.

Fancy S P, Harrington E P, Yuen T J, Silbereis J C, Zhao C, Baranzini S E, Bruce C C, Otero J J, Huang E J, Nusse R, Franklin R J, Rowitch D H (2011) Axin2 as regulatory and therapeutic target in newborn brain injury and remyelination Nat Neurosci. 2011 Jun. 26; 14(8):1009-16

Gao, Thompson L, Zhou Q, Putheti P, Fahmy T M, Strom T B, and Metcalfe S (2009) Treg versus Th17 lymphocyte lineages are cross-regulated by LIF versus IL-6. Cell Cycle 8:9, 1444-1450.

Gillespie L N, Clark G M, Bartlett P F and Marzella P L (2001) LIF is more potent than BDNF in promoting neurite outgrowth of mammalian auditory neurons in vitro. Neuroreport, 12 2: 275-279.
Liu J, Zang D. (2009) Response of neural precursor cells in the brain of Parkinson's disease mouse model after LIF administration. Neurol Res. (7):681-6.
Jang et al (2010). A selective TrkB agonist with potent neurotrophic activities by 7,8-dihydroxyflavone. PNAS 107; 2687-2692
Huang S M, Mishina Y M, Liu S, Cheung A, Stegmeier F, Michaud G A, Charlat O, Wiellette E, Zhang Y, Wiessner S, Hild M, Shi X, Wilson C J, Mickanin C, Myer V, Fazal A, Tomlinson R, Serluca F, Shao W, Cheng H, Shultz M, Rau C, Schirle M, Schlegl J, Ghidelli S, Fawell S, Lu C, Curtis D, Kirschner M W, Lengauer C, Finan P M, Tallarico J A, Bouwmeester T, Porter J A, Bauer A, Cong F (2009) Tankyrase inhibition stabilizes axin and antagonizes Wnt signaling Nature. 2009 Oct. 1; 461(7264):614-20
Niwa et al (2009) A parallel circuit of LIF signalling pathways maintains pluripotency of mouse ES cells. Nature July 2; 460(7251):118-22
Park J, Gao W, Whiston R, Strom T B, Metcalfe S and Fahmy T M (2011) Modulation of CD4+ T lymphocyte lineage outcomes with targeted nanoparticle-mediated cytokine delivery. Mol Pharm. 8(1):143-52.
Pitman et al (2004) LIF receptor signalling modulates neural stem cell renewal Mol Cell Neurol 27:255-266.
V. Prima, M. Tennant, O. S. Gorbatyuk, N. Muzyczka, P. J. Scarpace and S. Zolotukhin (2004) Differential Modulation of Energy Balance by Leptin, Ciliary Neurotrophic Factor, and Leukemia Inhibitory Factor Gene Delivery: Microarray Deoxyribonucleic Acid-Chip Analysis of Gene Expression Endocrinology 145 (4): 2035
Reif A E, Allen J M (1964) The AKR thymic antigen and its distribution in leukaemias and nervous tissues J Exp Med. 1964 Sep. 1; 120:413-33
Reynolds A D, Stone D K, Hutter J A L, Benner E J, Mosley R L and Gendelman H E (2010) Regulatory T cells attenuate Th17 cell-mediated nigrostriatal dopaminergic neurodegeneration in a model of Parkinson's Disease. J Immunology. (184):2261-2271.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method of reducing apoptosis of dopaminergic cells in a subject comprising administering to the subject a pharmaceutical composition comprising a plurality of biodegradable nanoparticles, wherein the nanoparticles comprise:
an antibody, or a fragment or derivative thereof, that is able to bind selectively to Thy-1 or GDNF receptor α1 (GDNFR-α1) of a neural precursor cell; and
leukaemia inhibitory factor (LIF).

2. The method of claim 1, wherein the neural precursor cell comprises a neural stem cell and/or a neural progenitor cell.

3. The method of claim 1, wherein the antibody, or fragment or derivative thereof, is further able to bind selectively to one or more of the group consisting of: a pluripotent stem cell; a totipotent stem cell; an embryonic stem cell (ESC); an induced pluripotent stem cell (iPSC); induced neural cells (iN); induced dopaminergic cells (iDA); induced oligodendrocytes (iOD); a T lymphocyte; an ectodermal cell; a precursor cell having commitment to a neurectodermal lineage; a neural cell; and a neuronal cell.

4. The method of claim 1, wherein the subject is an animal.

5. The method of claim 4, wherein the animal is a mammal.

6. The method of claim 4, wherein the animal is selected from the group consisting of: sheep; cattle; rodents; rabbits; pigs; cats; dogs; and primates.

7. The method of claim 6, wherein the primate is a human.

8. The method of claim 1, wherein the antibody, or fragment or derivative thereof is selected from a monoclonal antibody; a polyclonal antibody; an antigen-binding antibody fragment; $F_{ab}$; $scF_v$; Bis-$scF_v$; $V_L$; V-NAR; VhH; an aptamer, and an affinity binding protein.

9. The method of claim 1, wherein the nanoparticles are capable of degrading over a period of time in order to effect timed release of the LIF.

10. The method of claim 9, wherein up to 50% by weight of the LIF comprised within the nanoparticles is released in 1-5 days following administering to the subject the pharmaceutical composition comprising the plurality of biodegradable nanoparticles.

11. The method of claim 9, wherein the period of time is selected from the group consisting of: 1, 2, 3, 4, 5, 6, 7, 8, 9, 10, 12 days; 1, 2, 3, 4, 5 or 6 weeks; and up to six months.

12. The method of claim 1, wherein the nanoparticles comprise a biodegradable polymer layer that encapsulates the LIF, the polymer comprising poly(lactic)-co-glycolic acid (PLGA) and/or PLA or a suitable biocompatible equivalent.

13. The method of claim 12, wherein the nanoparticles comprise at most about 500 ng of LIF per mg of polymer.

14. The method of claim 1, wherein the nanoparticles have a diameter of at least about 50 nm and at most about 300 nm.

15. The method of claim 1, wherein the nanoparticles have a diameter of at least about 100 nm and at most about 200 nm.

16. The method of claim 1, wherein the nanoparticles further comprise one or more compounds selected from: brain-derived neurotrophic factor (BDNF) or an agonist thereof; epidermal growth factor (EGF) or an agonist thereof; glial cell-derived neurotrophic factor (GDNF) or an agonist thereof; retinoic acid and derivatives thereof; ciliary neurotrophic factor (CTNF) or an agonist thereof; and Wnt5A.

17. A method of increasing a population of dopaminergic neurons comprising:
administering to a population of cells comprising a neural precursor cell a composition comprising a plurality of biodegradable nanoparticles, wherein the nanoparticles comprise:
an antibody, or a fragment or derivative thereof, that is able to bind selectively to Thy-1 or GDNF receptor α1 (GDNFR-α1) of a neural precursor cell; and
leukaemia inhibitory factor (LIF).

18. The method of claim 17, further comprising administering the cells to a subject subsequent to administering the composition to the population of cells.

* * * * *

UNITED STATES PATENT AND TRADEMARK OFFICE
CERTIFICATE OF CORRECTION

PATENT NO. : 10,835,611 B2
APPLICATION NO. : 15/990259
DATED : November 17, 2020
INVENTOR(S) : Susan Marie Metcalfe and Tarek Fahmy It is certified that error appears in the above-identified patent and that said Letters Patent is hereby corrected as shown below:

In the Claims

In Claim 8, Column 24, Line 18, after "Bis-scF$_v$;" insert --V$_H$--.

Signed and Sealed this
Twenty-fourth Day of August, 2021

Drew Hirshfeld
*Performing the Functions and Duties of the*
*Under Secretary of Commerce for Intellectual Property and*
*Director of the United States Patent and Trademark Office*